United States Patent
Chen et al.

(10) Patent No.: US 11,612,618 B2
(45) Date of Patent: Mar. 28, 2023

(54) COMPOSITIONS FOR USE IN THE TREATMENT AND PREVENTION OF CARDIOVASCULAR DISORDERS RESULTING FROM CEREBROVASCULAR INJURY

(71) Applicant: Henry Ford Health System, Detroit, MI (US)

(72) Inventors: Jieli Chen, Troy, MI (US); Michael Chopp, Southfield, MI (US)

(73) Assignee: Henry Ford Health System, Detroit, MI (US)

( * ) Notice: Subject to any disclaimer, the term of this patent is extended or adjusted under 35 U.S.C. 154(b) by 0 days.

(21) Appl. No.: 16/763,290

(22) PCT Filed: Nov. 14, 2018

(86) PCT No.: PCT/US2018/061017
§ 371 (c)(1),
(2) Date: May 12, 2020

(87) PCT Pub. No.: WO2019/099493
PCT Pub. Date: May 23, 2019

(65) Prior Publication Data
US 2020/0297750 A1    Sep. 24, 2020

Related U.S. Application Data

(60) Provisional application No. 62/586,102, filed on Nov. 14, 2017.

(51) Int. Cl.
| | | |
|---|---|---|
| *A61K 31/7105* | (2006.01) | |
| *A61P 9/04* | (2006.01) | |
| *A61K 9/00* | (2006.01) | |
| *A61K 9/127* | (2006.01) | |

(52) U.S. Cl.
CPC ........ *A61K 31/7105* (2013.01); *A61K 9/0019* (2013.01); *A61K 9/127* (2013.01); *A61P 9/04* (2018.01)

(58) Field of Classification Search
None
See application file for complete search history.

(56) References Cited

U.S. PATENT DOCUMENTS

| 9,301,969 B2 | 4/2016 | Roh et al. |
|---|---|---|
| 2013/0017223 A1 | 1/2013 | Hope et al. |
| 2013/0156801 A1 | 6/2013 | Bond et al. |
| 2013/0287772 A1* | 10/2013 | Halbert ............... A61P 17/00 435/6.12 |
| 2016/0082049 A1* | 3/2016 | Chen ................ A61K 35/51 536/24.5 |
| 2016/0346334 A1 | 12/2016 | Trujillo |

OTHER PUBLICATIONS

Van Empel et al (Curr Hypertens Rep, Sep. 21, 2012) (Year: 2012).*
Zernecke et al (Science Signaling, vol. 2, Issue 100 ra81, Dec. 8, 2009) (Year: 2009).*
Flammer et al. (European Heart Journal, 2012, 33, 2963-2969). (Year: 2012).*
Bejot et al., "Stroke in diabetic patients," Diabetes Metab, Oct. 2010, vol. 36, Suppl. 3, pp. S84-S87.
Chen et al, "MiR-126 Affects Brain-Heart Interaction after Cerebral Ischemic Stroke," Translational Stroke Research, vol. 8, No. 4, Jan. 19, 2017, p. 374-385.
Chen et al, "MiR-126 Contributes to Human Umbilical Cord Blood Cell-Induced Neurorestorative Effects After Stroke in Type-2 Diabetic Mice : Neurorestoration of HUCBC in Diabetic Stroke," Stem Cells, vol. 34, No. 1, Jan. 1, 2016, p. 102-113.
Chen et al., "Abstract WMP43: Neurorestorative Therapy of Stroke in T2DM Mice With Exosomes Derived From Brain Endothelial Cells," Stroke, Feb. 21, 2017, vol. 48:AWMP 43, 5 pages.
Chronic Heart Failure: National Clinical Guideline for Diagnosis and Management in Primary and Secondary Care (2010) NICE Clinical Guidelines No. 108, 46 pages.
Duda et al., "A protocol for phenotypic detection and enumeration of circulating endothelial cells and circulating progenitor cells in human blood," Nat. Protoc., Apr. 5, 2007, vol. 2, No. 4, pp. 805-810.
Fryar et al., "Prevalence of Uncontrolled Risk Factors for Cardiovascular Disease: United States 1999-2010 NCHS Data Brief No. 103," Hyattsville MD: National Center for Health Statistics Centers for Disease Control and Prevention US Dept of Health and Human Services, 8 pages.
Ha, et al. "Exosomes as therapeutic drug carriers and delivery vehicles across biological membranes: current perspectives and future challenges," Acta Pharmaceutica Sinica B, Jul. 2016, vol. 6, Issue 4, p. 287-296.
Hu et al., "MicroRNAs 125a and 455 Repress Lipoprotein-Supported Steroidogenesis by Targeting Scavenger Receptor Class B Type I in Steroidogenic Cells," Mol Cell Biol., Dec. 2012, vol. 32, No. 24, pp. 5035-5045.
International Search Report and Written Opinion for PCT/US2018/061017, dated Jan. 1, 2018, 12 pages.
Komaki et al., "Exosomes of human placenta-derived mesenchymal stem cells stimulate angiogenesis," Stem Cell Res Ther., 2017, vol. 8, p. 219.
Lener et al., "Applying extracellular vesicles based therapeutics in clinical trials," J Extracell Vesicles, 2015, vol. 4, pp. 1-31.
Lewis et al., "Conserved seed pairing, often flanked by adenosines, indicates that thousands of human genes are microRNA targets," Cell, Jan. 14, 2005, vol. 120, No. 1, pp. 15-20.

(Continued)

*Primary Examiner* — Celeste A Roney
(74) *Attorney, Agent, or Firm* — Honigman LLP; Fernando Alberdi; Jonathan P. O'Brien

(57) ABSTRACT

Provided herein are methods for the prevention and treatment of cardiovascular diseases and disorders in a subject diagnosed as having suffered a cerebrovascular injury by administering agents that contain or induce the expression of microRNA-126.

10 Claims, 28 Drawing Sheets
Specification includes a Sequence Listing.

(56) References Cited

OTHER PUBLICATIONS

Li et al., "Exosomes Derived From Human Umbilical Cord Mesenchymal Stem Cells Alleviate Liver Fibrosis," Stem Cells Dev., Sep. 24, 2012, vol. 22, No. 6, pp. 845-854.

Qiao et al., "Human mesenchymal stem cells isolated from the umbilical cord," Cell Biol Int., Aug. 2, 2007, vol. 32, No. 1, pp. 8-15.

Remington's Pharmaceutical Sciences (17th Ed., Mack Pub. Co. 1985), Table of Contents, 5 pages.

Saunderson et al. "Induction of Exosome Release in Primary B Cells Stimulated via CD40 and the IL-4 Receptor," J Immunol, Jun. 15, 2008, vol. 15180, No. 12, pp. 8146-8152.

Sisakian, "Cardiomyopathies: Evolution of pathogenesis concepts and potential for new therapies," World J Cardiol, Jun. 26, 2014, vol. 6, No. 6, pp. 478-494.

Szatanek et al., "Isolation of extracellular vesicles: Determining the correct approach," Int J Mol Med., Apr. 22, 2015, vol. 36, No. 1, pp. 11-17.

Théry et al., "Isolation and characterization of exosomes from cell culture supernatants and biological fluids," Curr Protoc Cell Biol, Apr. 1, 2006, Chapter 3: Unit 3.22, 29 pages.

Trivedi et al., "Modification of tumor cell exosome content by transfection with wt-p53 and microRNA-125b expressing plasmid DNA and its effect on macrophage polarization," Oncogenesis, Aug. 2016, vol. 5, No. 8, e250, pp. 1-12.

Tuttolomondo, "Relationship between Diabetes and Ischemic Stroke: Analysis of Diabetes-Related Risk Factors for Stroke and of Specific Patterns of Stroke Associated with Diabetes Mellitus", J Diabetes Metab, vol. 6, No. 5, Jan. 1, 2015, 8 pages.

Willis et al., "Toward Exosome-Based Therapeutics: Isolation, Heterogeneity, and Fit-for-Purpose Potency", Front Cardiovasc Med., Oct. 9, 2017, vol. 4, Article 63, pp. 1-13.

Witkowski et al., "Micro-RNA-126 reduces the blood thrombogenicity in diabetes mellitus via targeting of tissue factor," Arterioscler. Thromb. Vasc. Biol., Jun. 2016, pp. 1263-1271.

Witwer et al., "Standardization of sample collection, isolation and analysis methods in extracellular vesicle research", J Extracell Vesicles, May 27, 2013, vol. 2, Issue 1, pp. 1-25.

Yu et al., "Exosomes as miRNA Carriers: Formation-Function-Future," Int J Mol Sci., Dec. 2, 2016, vol. 17, No. 12, pp. 1-12.

* cited by examiner

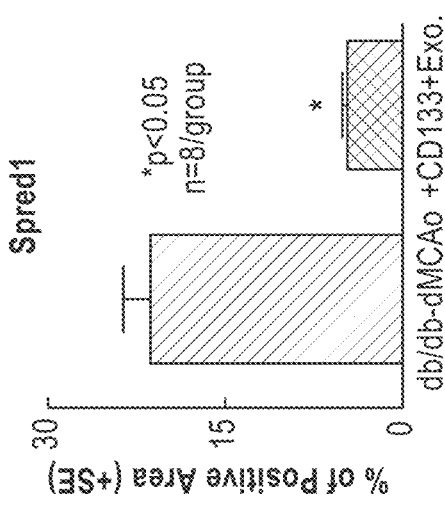
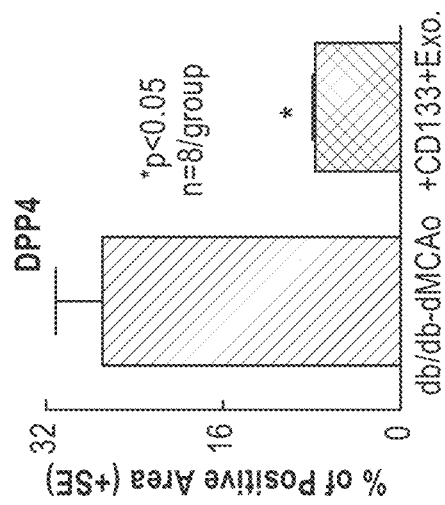
FIG. 13C
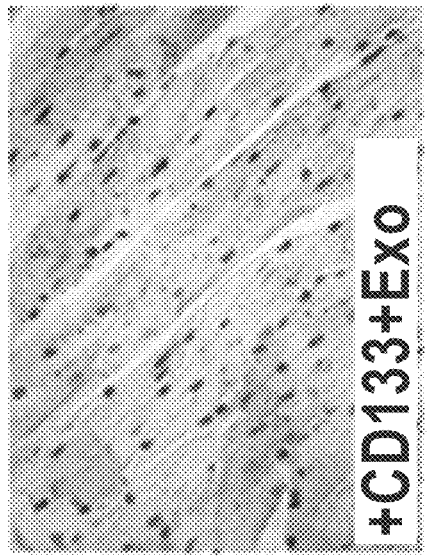
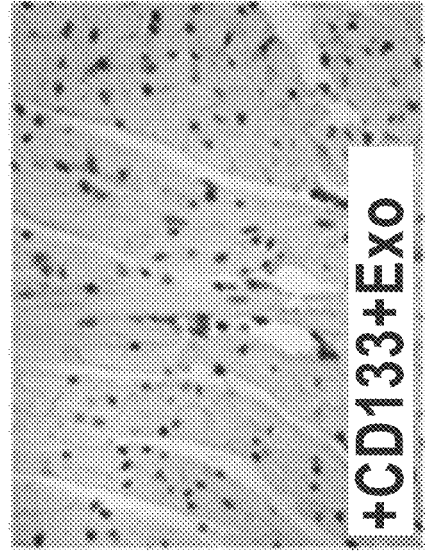
FIG. 13D
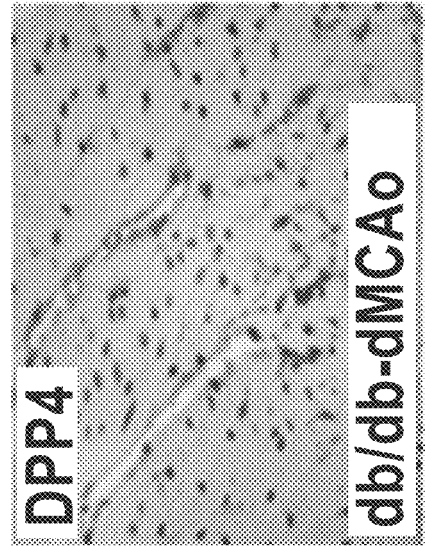

COMPOSITIONS FOR USE IN THE TREATMENT AND PREVENTION OF CARDIOVASCULAR DISORDERS RESULTING FROM CEREBROVASCULAR INJURY

CROSS-REFERENCE TO RELATED APPLICATIONS

This application is a U.S. National Phase Application, filed under 35 U.S.C. § 371, of International Application No. PCT/US2018/061017 filed on Nov. 14, 2018, which claims priority to, and the benefit of, U.S. Provisional Application No. 62/586,102, filed Nov. 14, 2017, the contents of each of which are incorporated herein by reference their its entireties.

GOVERNMENT SUPPORT

This invention was made with government support under Grant Numbers R01HL143432, R01NS083078 and R01NS099030 awarded by the National Institutes of Health. The government has certain rights in the invention.

SEQUENCE LISTING

The instant application contains a Sequence Listing which has been submitted in ASCII format via EFS-Web and is hereby incorporated by reference in its entirety. Said ASCII copy, created on May 10, 2020, is named "NEUX-006_N01US_SeqList.txt" and is about 2.9 KB in size.

TECHNICAL FIELD

Without limitation, some embodiments comprise methods, systems, and/or compositions relating to microRNAs and/or cell based therapies and the use of the same in the research, diagnosis, or treatment of injury or disease.

BACKGROUND

Stroke is a prominent cause of mortality and long-term disability and is accompanied by unusually high social and medical costs. The major causes of death in stroke-related moralities are a consequence of neurological damage and/or cardiovascular complications. Co-morbidity of stroke with hypertension, diabetes, or cardiac abnormalities aggravates stroke outcome, disability, risk of recurrent stroke, and mortality. However, cardiac dysfunction is encountered frequently among stroke patients, even in the absence of primary heart disease. Post-stroke neurological deficits increase the risk of cardiovascular diseases roughly by three times, and the ischemic brain transmits indirect cell death signals to the heart. Necropsy analyses of patients who suffered a fatal cerebral stroke indicate a high prevalence of coronary atherosclerosis and myocardial infarction. Patients can develop myocardial injuries after stroke even when patients do not have pre-existing cardiac diseases. However, it is unclear how cerebral ischemic stroke regulates cardiac function, what are the direct effects of stroke on cardiac function, and what are the underlying molecular mechanisms.

MicroRNAs (miRNAs) are small non-coding RNA molecules that regulate several gene expressions, pathways, and complex biological networks at the cellular level acting either exclusively or together with other miRNAs. MiRNAs regulate both transcriptional and post-transcriptional gene expression as well as regulate several circuits involved in tissue repair, inflammation, hypoxia-response, and angiogenesis. MicroRNA-126 (miR-126) is endothelial cell (EC) specific and plays a key role in regulating EC function, controlling angiogenesis, and maintaining vascular integrity. MiR-126 facilitates vascular re-modeling, decreases fibrosis in multiple organs, and has been reported to be beneficial in the treatment of atherosclerosis and re-stenosis. MiR-126 expression in serum is positively correlated with left ventricular ejection fraction (LVEF). To date, there have been few effective modalities in the treatment of cardiovascular disease and/or disorder subsequent to stroke, including in subjects with a glucose metabolism disorder. The present disclosure provides experimental support regarding the treatment of cardiovascular disease or disorder subsequent to stroke, using a novel composition.

SUMMARY OF THE INVENTION

The present disclosure provides a method for the treatment or prevention of a cardiovascular disorder or disease in a subject who has suffered cerebrovascular injury, the method comprising administering a therapeutically effective amount of a miR-126 containing agent or an agent that induces expression of miR-126 to the subject in need thereof. The present disclosure provides a method for the combination of treatment and prevention of a cardiovascular disorder or disease in a subject who has suffered cerebrovascular injury, the method comprising administering a therapeutically effective amount of a miR-126 containing agent or an agent that induces expression of miR-126 to the subject in need thereof.

The present disclosure provides a miR-126 containing agent or an agent that induces expression of miR-126 for use in the treatment or prevention of a cardiovascular disorder or disease in a subject who has suffered cerebrovascular injury, wherein the miR-126 containing agent or the agent that induces expression of miR-126 is for administration to the subject in at least one therapeutically effective amount. The present disclosure provides a miR-126 containing agent or an agent that induces expression of miR-126 for use in the combination of treatment and prevention of a cardiovascular disorder or disease in a subject who has suffered cerebrovascular injury, wherein the miR-126 containing agent or the agent that induces expression of miR-126 is for administration to the subject in at least one therapeutically effective amount.

The present disclosure provides a use of a miR-126 containing agent or an agent that induces expression of miR-126 for the manufacture of a medicament for the treatment or prevention of a cardiovascular disorder or disease in a subject who has suffered cerebrovascular injury, wherein the miR-126 containing agent or the agent that induces expression of miR-126 is for administration to the subject in at least one therapeutically effective amount. The present disclosure provides a use of a miR-126 containing agent or an agent that induces expression of miR-126 for the manufacture of a medicament for the combination of treatment and prevention of a cardiovascular disorder or disease in a subject who has suffered cerebrovascular injury, wherein the miR-126 containing agent or the agent that induces expression of miR-126 is for administration to the subject in at least one therapeutically effective amount.

The present disclosure provides a method for the treatment or prevention of a cardiovascular disorder or disease in a subject who has suffered an ischemic stroke, the method comprising administering a therapeutically effective amount of an miR-126 containing agent or an agent that induces expression of miR-126 to the subject in thereof. The present disclosure provides a method for the combination of treatment and prevention of a cardiovascular disorder or disease in a subject who has suffered an ischemic stroke, the method comprising administering a therapeutically effective amount of an miR-126 containing agent or an agent that induces expression of miR-126 to the subject in thereof.

The present disclosure provides a miR-126 containing agent or an agent that induces expression of miR-126 for use in the treatment or prevention of a cardiovascular disorder or disease in a subject who has suffered an ischemic stroke, wherein the miR-126 containing agent or the agent that induces expression of miR-126 is for administration to the subject in at least one therapeutically affective amount. The present disclosure provides a miR-126 containing agent or an agent that induces expression of miR-126 for use in the combination of treatment and prevention of a cardiovascular disorder or disease in a subject who has suffered an ischemic stroke, wherein the miR-126 containing agent or the agent that induces expression of miR-126 is for administration to the subject in at least one therapeutically affective amount.

The present disclosure provides a use of a miR-126 containing agent or an agent that induces expression of miR-126 for the manufacture of a medicament for the treatment or prevention of a cardiovascular disorder or disease in a subject who has suffered an ischemic stroke, wherein the miR-126 containing agent or the agent that induces expression of miR-126 is for administration to the subject in at least one therapeutically affective amount. The present disclosure provides a use of a miR-126 containing agent or an agent that induces expression of miR-126 for the manufacture of a medicament for the combination of treatment and prevention of a cardiovascular disorder or disease in a subject who has suffered an ischemic stroke, wherein the miR-126 containing agent or the agent that induces expression of miR-126 is for administration to the subject in at least one therapeutically affective amount.

The present disclosure provides a method for the treatment or prevention of a cardiovascular disorder or disease in a subject with a glucose metabolism disorder who has suffered a stroke by administering a therapeutically effective amount of an miR-126 containing agent to subject in need thereof. The present disclosure provides a method for the combination of treatment and prevention of a cardiovascular disorder or disease in a subject with a glucose metabolism disorder who has suffered a stroke by administering a therapeutically effective amount of an miR-126 containing agent to subject in need thereof.

The present disclosure provides a miR-126 containing agent or an agent that induces expression of miR-126 for use in the treatment or prevention of a cardiovascular disorder or disease in a subject with a glucose metabolism disorder who has suffered a stroke, wherein the miR-126 containing agent or the agent that induces expression of miR-126 is for administration to the subject in at least one therapeutically affective amount. The present disclosure provides a miR-126 containing agent or an agent that induces expression of miR-126 for use in the combination of treatment and prevention of a cardiovascular disorder or disease in a subject with a glucose metabolism disorder who has suffered a stroke, wherein the miR-126 containing agent or the agent that induces expression of miR-126 is for administration to the subject in at least one therapeutically affective amount.

The present disclosure provides a use of a miR-126 containing agent or an agent that induces expression of miR-126 for the manufacture of a medicament for the treatment or prevention of a cardiovascular disorder or disease in a subject with a glucose metabolism disorder who has suffered a stroke, wherein the miR-126 containing agent or the agent that induces expression of miR-126 is for administration to the subject in at least one therapeutically affective amount. The present disclosure provides a use of a miR-126 containing agent or an agent that induces expression of miR-126 for the manufacture of a medicament for the combination of treatment and prevention of a cardiovascular disorder or disease in a subject with a glucose metabolism disorder who has suffered a stroke, wherein the miR-126 containing agent or the agent that induces expression of miR-126 is for administration to the subject in at least one therapeutically affective amount.

The present disclosure provides a method for the treatment or prevention of a cardiovascular disorder or disease in a subject with a glucose metabolism disorder who has suffered an ischemic stroke by administering a therapeutically effective amount of an miR-126 containing agent to the subject in need thereof. The present disclosure provides a method for the combination of treatment and prevention of a cardiovascular disorder or disease in a subject with a glucose metabolism disorder who has suffered an ischemic stroke by administering a therapeutically effective amount of an miR-126 containing agent to the subject in need thereof.

The present disclosure provides a miR-126 containing agent or an agent that induces expression of miR-126 for use in the treatment or prevention of a cardiovascular disorder or disease in a subject with a glucose metabolism disorder who has suffered an ischemic stroke, wherein the miR-126 containing agent or the agent that induces expression of miR-126 is for administration to the subject in at least one therapeutically affective amount. The present disclosure provides a miR-126 containing agent or an agent that induces expression of miR-126 for use in the combination of treatment and prevention of a cardiovascular disorder or disease in a subject with a glucose metabolism disorder who has suffered an ischemic stroke, wherein the miR-126 containing agent or the agent that induces expression of miR-126 is for administration to the subject in at least one therapeutically affective amount.

The present disclosure provides a use of a miR-126 containing agent or an agent that induces expression of miR-126 for the manufacture of a medicament for the treatment or prevention of a cardiovascular disorder or disease in a subject with a glucose metabolism disorder who has suffered an ischemic stroke, wherein the miR-126 containing agent or the agent that induces expression of miR-126 is for administration to the subject in at least one therapeutically affective amount. The present disclosure provides a use of a miR-126 containing agent or an agent that induces expression of miR-126 for the manufacture of a medicament for the combination of treatment and prevention of a cardiovascular disorder or disease in a subject with a glucose metabolism disorder who has suffered an ischemic stroke, wherein the miR-126 containing agent or the agent that induces expression of miR-126 is for administration to the subject in at least one therapeutically affective amount.

In all methods, agents and uses of the present disclosure, a cardiovascular disorder or disease can be a condition selected from the group consisting of cardiomyocyte hypertrophy, myocardial fibrosis, cardiovascular-related cognitive decline, fibrosis, myocardial infarction, rheumatic heart disease, inflammatory heart disease, hypertensive heart disease, congenital heart disease, cardiac arrhythmias, aneurysm, angina, atherosclerosis, cardiomyopathy, carditis, congenital heart disease, coronary heart disease, coronary artery disease, heart failure, peripheral arterial disease, valvular heart disease, peripheral artery disease, thromboembolic disease, and venous thrombosis.

In all methods, agents and uses of the present disclosure, a cerebrovascular injury can be a stroke.

In all methods, agents and uses of the present disclosure, a stroke can be an ischemic stroke.

In all methods, agents and uses of the present disclosure, a stroke can be a hemorrhagic stroke.

In all methods, agents and uses of the present disclosure, a cardiovascular disorder or disease can be heart failure or cardiomyopathy.

In all methods, agents and uses of the present disclosure, heart failure can be systolic heart failure.

In all methods, agents and uses of the present disclosure, heart failure can be denoted by a left ventricle ejection fraction (LVEF) of less than 40%.

In all methods, agents and uses of the present disclosure, a subject can be a human.

In all methods, agents and uses of the present disclosure, a therapeutically effective amount of a miR-126 containing agent can range from about 0.0001 μg/kg to 1.0 mg/kg the subject's body weight.

In all methods, agents and uses of the present disclosure, a miR-126 containing agent can be an exosome containing miR-126 miRNA or a microvesicle containing miR-126 miRNA.

In all methods, agents and uses of the present disclosure, an exosome containing miR-126 miRNA or a microvesicle containing miR-126 miRNA can be derived or isolated from stem cells, endothelial cells, mesenchymal stromal cells, umbilical cord cells, cerebral endothelial cells, brain microvascular endothelial cells, Primary Human Brain Microvascular Endothelial Cells (ACBRI 376), endothelial progenitor cells, AC-133/CD-133+ cells and the like, Schwann cells, hematopoietic cells, reticulocytes, monocyte-derived dendritic cells (MDDCs), monocytes, macrophages, B lymphocytes, antigen-presenting cells, glial cells, astrocytes, neurons, oligodendrocytes, spindle neurons, microglia, mastocytes, CD4+ lymphocytes, T lymphocytes, or platelets.

In all methods, agents and uses of the present disclosure, an exosome containing miR-126 miRNA or a microvesicle containing miR-126 miRNA can be derived or isolated from endothelial cells or CD133+ cells In all methods, agents and uses of the present disclosure, a CD133+ cell can be a hematopoietic progenitor cell, a hematopoietic stem cell, or a CD133+ human umbilical cord blood cell (HUCBC).

In all methods, agents and uses of the present disclosure, a CD133+ cell can be selected from a population of CD133+/KDR+ cells.

In all methods, agents and uses of the present disclosure, a therapeutically effective amount of the miR-126 containing agent can comprise from about $1 \times 10^7$ to about $1 \times 10^{17}$ exosomes or microvesicles. A therapeutically effective amount of miR-126 containing agent can comprise from about $1 \times 10^{12}$ to about $1 \times 10^{15}$ exosomes.

In all methods, of the present disclosure, a miR-126 containing agent can be administered by intravenous injection, intra-arterial injection, subcutaneous injection, intramuscular injection, intra-arterial injection, intradermal injection, intraperiotoneally, stereotactically, orally, intranasally, mucosally, topically, intrarectally, intravaginally, and intrathecally.

In all agents and uses of the present disclosure, a miR-126 containing agent is for administration by intravenous injection, intra-arterial injection, subcutaneous injection, intramuscular injection, intra-arterial injection, intradermal injection, intraperiotoneally, stereotactically, orally, intranasally, mucosally, topically, intrarectally, intravaginally, and intrathecally.

In all methods, agents and uses of the present disclosure, a glucose metabolism disorder can be Diabetes Mellitus; Experimental Diabetes Mellitus; Type 1 Diabetes Mellitus; Wolfram Syndrome; Type 2 Diabetes Mellitus; Lipoatrophic Diabetes Mellitus; Gestational Diabetes; Diabetic Ketoacidosis; Donohue Syndrome; Latent Autoimmune Diabetes in Adults; Prediabetic State; Glycosuria; Renal Glycosuria; Hyperglycemia; Glucose Intolerance; Hyperinsulinism; Congenital Hyperinsulinism; Nesidioblastosis; Insulin Resistance; Metabolic Syndrome X; Hypoglycemia; and Insulin Coma; Congenital Autoimmune Diabetes Mellitus, Insulin-Resistant Diabetes Mellitus with Acanthosis Nigricans; Neonatal Diabetes Mellitus with Congenital Hypothyroidism; Permanent Neonatal Diabetes Mellitus; Permanent Neonatal Diabetes with Neurologic Features, Transient Neonatal Diabetes Mellitus 1, Transient Neonatal Diabetes Mellitus 2, and Transient Neonatal Diabetes Mellitus 3.

Any of the above aspects can be combined with any other aspect.

Unless otherwise defined, all technical and scientific terms used herein have the same meaning as commonly understood by one of ordinary skill in the art to which this disclosure belongs. In the Specification, the singular forms also include the plural unless the context clearly dictates otherwise; as examples, the terms "a," "an," and "the" are understood to be singular or plural and the term "or" is understood to be inclusive. By way of example, "an element" means one or more element. Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps. Unless otherwise clear from the context, all numerical values provided herein are modified by the term "about."

Although methods and materials similar or equivalent to those described herein can be used in the practice or testing of the present disclosure, suitable methods and materials are described below. All publications, patent applications, patents, and other references mentioned herein are incorporated by reference in their entirety. The references cited herein are not admitted to be prior art to the claimed invention. In the case of conflict, the present Specification, including definitions, will control. In addition, the materials, methods, and examples are illustrative only and are not intended to be limiting. Other features and advantages of the disclosure will be apparent from the following detailed description and claim.

BRIEF DESCRIPTION OF THE DRAWINGS

Some embodiments will now be described, by way of example only and without waiver or disclaimer of other embodiments, with reference to the accompanying drawings, in which:

FIG. 2A depicts histologic immunostaining of ED1 (quantified in the bar graph on the right of the panels). FIG. 2B. depicts histologic immunostaining of TGF-β (quantified in the bar graph on the right of the panels). FIG. 2C depicts histologic immunostaining of NOX2 (quantified in the bar graph on the right of the panels) FIG. 2D shows the results of a western blot assay.

As shown in FIG. 3B, target mRNA is increased in stroke mice, with Western blot shown to the right. In FIG. 3C, MCP-1 immunostaining and quantitative data are shown.

FIG. 4A, FIG. 4B, FIG. 4C and FIG. 4D depict the reduction in miR-126 expression and cardiac function in knockout stroke mice, and the effect of stroke on cardiac function in knockout mice. As show in FIG. 4A, miR-126 knockout mice have decreased miR-126 expression. FIG. 4B compares echocardiographs from knockout and wild-type (WT) mice, with cardiac function on the right. As shown in FIG. 4C brain tissue and brain lesion volume is not significantly increased in knockout mice. As shown in FIG. 4D, Picro Sirius Red (PSR) staining reveals increased myocyte cross-sectional area (MCSA) and interstitial collagen fraction (ICF). Quantification of values shown in bar graphs on the right.

As shown in FIG. 5A, NOX2 immunostaining is increased in knockout stroke mice. As shown in FIG. 5B, TGF-β immunostaining is increased in knockout mice. FIG. 5C shows miR-126 expression in heart and serum. As shown in FIG. 5D, miR-126 targets VCAM-1 and MCP-1 expression is increased in knockout mice.

FIG. 6A confirms the cell population as primarily cardiomyocyte using sarcomeric a-actinin. FIG. 6B confirms the decrease in expression in knockdown cardiomyocytes. As shown in FIG. 6C, MCP-1, VCAM-1 and TGF-β, and NOX2 gene expression is increased in miR-126 knockdown cells. FIG. 6D shows the increase in cardiomyocyte surface area (hypertrophy) in knockdown cells. FIG. 6E depicts the decreased miR-126 in endothelial cell exosome obtained from knockout mice. As shown in FIG. 6F and FIG. 6G, addition of endothelial cell exosomes decreased cardiomyocyte size (hypertrophy).

As shown in FIG. 9A, the effects of the miR-126 inhibitor and promoter is confirmed in endothelial cell exosomes (EC-Exo). FIG. 9B shows the result of an object test after stroke/T2DM mice were intravenously treated with either control, miR-126-inhibited exosomes, or miR-126-overexpressed exosomes. FIG. 9C shows the results of a cognitive odor test following intravenous treatment.

FIG. 11A, FIG. 11B, FIG. 11C and FIG. 11D depict motor and cognitive results. As shown in FIG. 11E and FIG. 11F, cardiac function improved in stroke/T2DM mice treated with CD133+ exosomes. FIG. 11G and FIG. 11H depict echocardiographs in control and CD133+ treated mice, showing a decrease in left ventricular diastolic dysfunction (LVDD) in the later. FIG. 11I and FIG. 11J correlate cognitive function with cardiac function.

FIG. 12A, FIG. 12B and FIG. 12C show decreased immunostaining and ICF in CD133+ exosome treated mice compared to controls.

FIG. 13A, FIG. 13B, FIG. 13C, FIG. 13D and FIG. 13E depicts increased miR-126 expression in stroke/T2DM mice following treatment with CD133+ exosomes. FIG. 13A shows the change in miRNA expression following treatment with CD133+ exosomes. As shown in FIG. 13B, the mRNA of miR-126 targets is decreased following treatment. FIG. 13C, FIG. 13D and FIG. 13E depict protein levels of another miRNA target following CD133+ exosome treatment.

DETAILED DESCRIPTION

Figure 1A:
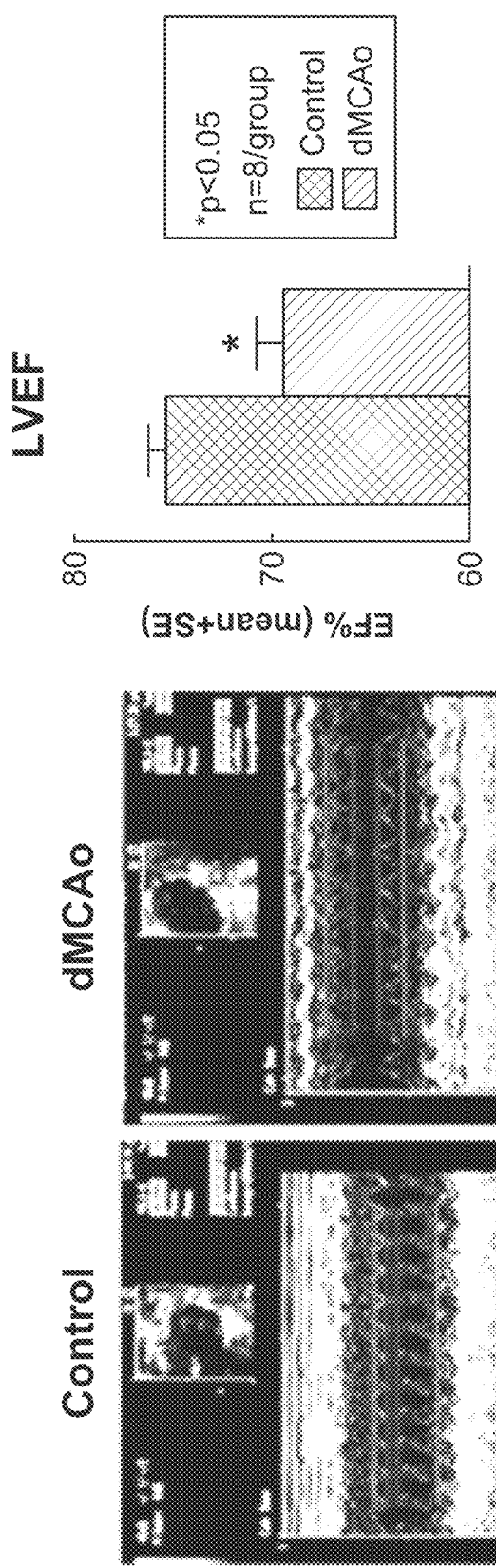
FIG. 1A depicts various experimental results of induced stroke in mice. Echocardiograph measurements of left ventricle ejection fraction (LVEF) in conscious control and dMCAo mice at 28-days post stroke are shown on the left and a bar graph quantifying values is shown on the right.

Throughout this specification, unless specifically stated otherwise or the context requires otherwise, reference to a single step, composition of matter, group of steps or group of compositions of matter shall be taken to encompass one and a plurality (i.e., one or more) of those steps, compositions of matter, groups of steps or group of compositions of matter.

Each example and embodiment of the disclosure is to be applied mutatis mutandis to each and every other example or embodiment unless specifically stated otherwise.

Those skilled in the art will appreciate that the present disclosure is susceptible to variations and modifications other than those specifically described. It is to be understood that the disclosure includes all such variations and modifications. The disclosure also includes all of the steps, features, compositions and compounds referred to or indicated in this specification, individually or collectively, and any and all combinations or any two or more of said steps or features.

The present disclosure is not to be limited in scope by the specific examples described herein, which are intended for the purpose of exemplification only. Functionally-equivalent compositions and methods are clearly within the scope of the disclosure.

The present disclosure is performed without undue experimentation using, unless otherwise indicated, conventional techniques of molecular biology, microbiology, virology, recombinant DNA technology, solid phase and liquid nucleic acid synthesis, peptide synthesis in solution, solid phase peptide synthesis, immunology, cell culture, formulation and medical treatments in cardiology. Such procedures are described, for example, in Sambrook, Fritsch & Maniatis, Molecular Cloning: A Laboratory Manual, Cold Spring Harbor Laboratories, New York, Second Edition (1989), whole of Vols I, II, and III; DNA Cloning: A Practical Approach, Vols. I and II (D. N. Glover, ed., 1985), IRL Press, Oxford, whole of text; Oligonucleotide Synthesis: A Practical Approach (M. J. Gait, ed, 1984) IRL Press, Oxford, whole of text, and particularly the papers therein by Gait, pp 1-22; Atkinson et al, pp 35-81; Sproat et al, pp 83-115; and Wu et al, pp 135-151; 4. Nucleic Acid Hybridization: A Practical Approach (B. D. Hames & S. J. Higgins, eds., 1985) IRL Press, Oxford, whole of text; Immobilized Cells and Enzymes: A Practical Approach (1986) IRL Press, Oxford, whole of text; Perbal, B., A Practical Guide to Molecular Cloning (1984); Methods In Enzymology (S. Colowick and N. Kaplan, eds., Academic Press, Inc.), whole of series; J. F. Ramalho Ortigao, "The Chemistry of Peptide Synthesis" In: Knowledge database of Access to Virtual Laboratory website (Interactiva, Germany); Sakakibara, D., Teichman, J., Lien, E. Land Fenichel, R. L. (1976). Biochem. Biophys. Res. Commun. 73 336-342; Merrifield, R. B. (1963). J. Am. Chem. Soc. 85, 2149-2154; Barany, G. and Merrifield, R. B. (1979) in The Peptides (Gross, E. and Meienhofer, 3. eds.), vol. 2, pp. 1-284, Academic Press, New York. 12. Wiinsch, E., ed. (1974) Synthese von Peptiden in Houben-Weyls Metoden der Organischen Chemie (Muler, E., ed.), vol. 15, 4th edn., Parts 1 and 2, Thieme, Stuttgart; Bodanszky, M. (1984) Principles of Peptide Synthesis, Springer-Verlag, Heidelberg; Bodanszky, M. & Bodanszky, A. (1984) The Practice of Peptide Synthesis, Springer-Verlag, Heidelberg; Bodanszky, M. (1985) Int. J. Peptide Protein Res. 25, 449-474; Handbook of Experimental Immunology, Vols. I-IV (D. M. Weir and C. C. Blackwell, eds., 1986, Blackwell Scientific Publications); Textbook of Interventional Cardiology, 7th Edition, Authors: Eric J. Topol & Paul S. Teirstein; and Animal Cell Culture: Practical Approach, Third Edition (John R. W. Masters, ed., 2000), ISBN 0199637970, whole of text; each of these references are incorporated herein by reference in their entireties.

Throughout this specification, unless the context requires otherwise, the word "comprise", or variations such as "comprises" or "comprising", will be understood to imply the inclusion of a stated step or element or integer or group of steps or elements or integers but not the exclusion of any other step or element or integer or group of elements or integers.

As used herein the term "derived from" shall be taken to indicate that a specified biological product, component or active agent may be obtained from a particular source albeit not necessarily directly from that source. For example, in the context of exosomes and/or microvesicles "derived" from a mammalian cell, this term refers to exosomes and/or microvesicles that are produced by exosome and/or microvesicle producing mammalian cells, for example, stem cells, endothelial cells, mesenchymal stromal cells, umbilical cord cells, cerebral endothelial cells, brain microvascular endothelial cells, Primary Human Brain Microvascular Endothelial Cells (ACBRI 376), endothelial progenitor cells, AC133/CD133+ cells and the like, Schwann cells, CD133+ cells, hematopoietic progenitor cells, hematopoietic stem cells, CD133+ human umbilical cord blood cell (HUCBC), CD133+/KDR+ cells, hematopoietic cells, reticulocytes, monocyte-derived dendritic cells (MDDCs), monocytes, macrophages, B lymphocytes, antigen-presenting cells, glial cells, astrocytes, neurons, oligodendrocytes, spindle neurons, microglia, mastocytes, CD4+ lymphocytes, T lymphocytes, or platelets or in vitro cell cultures of any of the foregoing. In the foregoing examples, the exemplary exosomes and/or microvesicles can be isolated from these exemplified cells, or may be cultured from mammalian tissue, for example, mammalian tissue or mammalian cultured cells.

As used herein, the term "miR-126 containing agent" includes: isolated miR-126 micro RNA; extracellular vesicles; exosomes; microvesicles (also known as ectosomes, shedding vesicles, microparticles, plasma membrane-derived vesicles, and exovesicles); matrix-bound nanovesicles (MBVs), apoptotic bodies; epididimosomes; exosome-like vesicles; argosomes; dexosomes; microparticles; promininosomes; texosomes; prostasomes; dex; tex; archeosomes; oncosomes; exosome-derived contents harvested or isolated from stem cells, endothelial cells, mesenchymal stromal cells, umbilical cord cells, endothelial cells, cerebral endothelial cells, brain microvascular endothelial cells, Primary Human Brain Microvascular Endothelial Cells (ACBRI 376), endothelial progenitor cells, AC-133/CD-133+ cells and the like, Schwann cells, hematopoietic cells, reticulocytes, monocyte-derived dendritic cells (MDDCs), monocytes, macrophages, B lymphocytes, antigen-presenting cells, glial cells, astrocytes, neurons, oligodendrocytes, spindle neurons, microglia, mastocytes, hemangioblast cells, lymphoid progenitor cells, myeloid progenitor cells, vascular stem cells, endothelial progenitor cells, pericytes, hematopoietic stem cells, endothelial progenitor cells, human umbilical cord blood cells (HUCBCs), CD133+/KDR+ cells, and/or any cell with an endomembrane system. MiR-126 containing agents may also include cells that are capable of synthesizing miR-126, for example, stem cells, endothelial cells, mesenchymal stromal cells, umbilical cord cells, endothelial cells hemangioblast cells, lymphoid progenitor cells, myeloid progenitor cells, vascular stem cells, endothelial progenitor cells, pericytes, hematopoietic stem cells, endothelial progenitor cells, human umbilical cord blood cells (HUCBCs), CD133+/KDR+ cells, and/or any cell with an endomembrane system. Further, as used herein, the term "miR-126 containing agent" can refer to all of the aforementioned agents, and compositions, including pharmaceutically acceptable compositions comprising miR-126 miRNA in combination with one or more acceptable carriers, vehicles, adjuvants, additives, and/or excipients.

As used herein, the term "effective amount" or "therapeutically effective amount" means the amount of miR-126 containing agent sufficient to effectuate a desired physiological outcome in an individual in need of the agent. The effective amount can vary among individuals depending on the health and physical condition of the individual to be treated, the taxonomic group of the individuals to be treated, the formulation of the composition, assessment of the individual's medical condition, and other relevant factors.

The term "benefit" is used in the broadest sense and refers to any desirable effect and specifically includes clinical benefit as defined herein. Clinical benefit can be measured by assessing various endpoints, e.g., inhibition, to some extent, of disease progression, including slowing down and complete arrest; reduction in the number of disease episodes and/or symptoms; reduction in lesion size; inhibition (i.e., reduction, slowing down or complete stopping) of disease cell infiltration into adjacent peripheral organs and/or tissues; inhibition (i.e. reduction, slowing down or complete stopping) of disease spread; decrease of auto-immune response, which may, but does not have to, result in the regression or ablation of the disease lesion; relief, to some extent, of one or more symptoms associated with the disorder; increase in the length of disease-free presentation following treatment, e.g., progression-free survival; increased overall survival; higher response rate; and/or decreased mortality at a given point of time following treatment.

"About" means within plus or minus (±) 10% of a value. For example, if it is stated, "a marker may be increased by about 50%", it is implied that the marker may be increased between 45%-55%, inclusive of the endpoints and all integers or fractions thereof between the stated range.

"Administering" means providing an agent to an animal, and includes, but is not limited to, administering by a medical professional and self-administering. In some embodiments, without limitation, the methods described herein can be administered intravenously; intraarterially; intradermally; subcutaneously; intramuscularly; intraperitoneally; stereotactically; orally; intranasally; mucosally; topically; intrarectally; intravaginally; intravitreally; intrastriatally; intrathecally; or by intravenous injection. The foregoing administration routes can be accomplished via implantable microbead (e.g., microspheres, sol-gel, hydrogels); injection; continuous infusion; localized perfusion; catheter; lavage. Methods for administering a formulation of a miR-126 containing agent can adapted from Remington's Pharmaceutical Sciences (17th Ed., Mack Pub. Co. 1985), the disclosure of which is incorporated herein by reference in its entirety.

"Amelioration" refers to a lessening of at least one indicator, sign, or symptom of an associated disease, disorder, or condition. The severity of indicators can be determined by subjective or objective measures, which are known to those skilled in the art.

"Cardiovascular disease" or "cardiovascular disorder" (used synonymously herein) refers to a group of conditions that exert a deleterious effect on the heart, blood vessels (arteries, capillaries, and veins), circulation, and/or one or more in combination, as they relate to the cardiovascular system. Examples of cardiovascular diseases or disorders include, but are not limited to, aneurysm, angina, aortic aneurysm, arrhythmia, atherosclerosis, cardiomyopathy, carditis, cerebrovascular disease, congenital heart disease, coronary heart disease, coronary artery disease, diabetic dyslipidemia, heart failure, hypertension, hypertensive heart disease, myocyte hypertrophy, myocardial fibrosis, cardiovascular-related cognitive decline; inflammation, fibrosis, myocardial infarction, rheumatic heart disease, inflammatory heart disease, hypertensive heart disease, congenital heart disease, cardiac arrhythmias, aneurysm, dyslipidemia, hyperlipidemia, hypercholesterolemia, hypertriglyceridemia, metabolic syndrome, myocardial infarction, peripheral arterial disease, rheumatic heart disease, valvular heart disease, peripheral artery disease, thromboembolic disease, and venous thrombosis.

"Diabetes mellitus" or "diabetes" or is a syndrome characterized by disordered metabolism and abnormally high blood sugar (hyperglycemia) resulting from insufficient levels of insulin or reduced insulin sensitivity. The characteristic symptoms are excessive urine production (polyuria) due to high blood glucose levels, excessive thirst and increased fluid intake (polydipsia) attempting to compensate for increased urination, blurred vision due to high blood glucose effects on the eye's optics, unexplained weight loss, and lethargy. Included within the definition are diabetes mellitus type 1 and diabetes mellitus type 2.

The term "distal middle cerebral artery occlusion (dMCAo)" refers to either a transient or permanent occlusion of the distal middle cerebral artery.

"Dosage unit" means a form in which a pharmaceutical agent is provided, e.g. pill, tablet, or other dosage unit known in the art. In certain embodiments, a dosage unit is a vial containing lyophilized antisense oligonucleotide. In certain embodiments, a dosage unit is a vial containing reconstituted antisense oligonucleotide. As used herein, the terms "dose" and "amount" are used interchangeably. Further, "Dose" or "Amount" can mean a specified quantity of a pharmaceutical agent provided in a single administration, or in a specified time period. In certain embodiments, a dose or amount can be administered in one, two, or more boluses, tablets, or injections. For example, in certain embodiments where subcutaneous administration is desired, the desired dose or amount requires a volume not easily accommodated by a single injection, therefore, two or more injections can be used to achieve the desired dose or amount. In certain embodiments, the pharmaceutical agent is administered by infusion over an extended period of time or continuously. Doses or amounts can be stated as the amount of pharmaceutical agent per hour, day, week, or month. Doses or amounts can be expressed as $\mu g/kg$, $mg/kg$, $g/kg$, $mg/m^2$ of surface area of the patient, or number of exosomes. For example, in one embodiment, a dose or amount may include administration of about $1\times10^7$ to about $1\times10^{17}$ exosomes administered per dose or amount, one or more times per day, or one or more times per week, or one or more times per month.

The term "ejection fraction (EF)" refers to the amount of blood pumped out of the heart with each beat, and is expressed as a percentage. As used herein, "left ventricle ejection fraction (LVEF)" refers to the percentage of blood pumped out of the left ventricle. Methods for determining LVEF in a human patient can include, but are not limited to, echocardiogram; cardiac catheterization; nuclear medicine scan, computerized tomography (CT); and/or magnetic resonance imaging (MRI) which are known in the art.

"Glucose" is a monosaccharide used by cells as a source of energy and metabolic intermediate. "Plasma glucose" refers to glucose present in the plasma.

"Glucose metabolism disorder" refers to a groups of conditions related to glucose processing and/or metabolism, characterized by an alteration or disturbance in metabolic function. "Metabolic" and "metabolism" are terms well known in the art and generally include the whole range of biochemical processes that occur within a living organism. Examples of glucose metabolism disorders include, but are not limited to, Diabetes Mellitus; Experimental Diabetes Mellitus; Type 1 Diabetes Mellitus; Wolfram Syndrome; Type 2 Diabetes Mellitus; Lipoatrophic Diabetes Mellitus; Gestational Diabetes; Diabetic Ketoacidosis; Donohue Syndrome; Latent Autoimmune Diabetes in Adults; Prediabetic State; Glycosuria; Renal Glycosuria; Hyperglycemia; Glucose Intolerance; Hyperinsulinism; Congenital Hyperinsulinism; Nesidioblastosis; Insulin Resistance; Metabolic Syndrome X; Hypoglycemia; and Insulin Coma; Congenital Autoimmune Diabetes Mellitus, Insulin-Resistant Diabetes Mellitus with Acanthosis Nigricans; Neonatal Diabetes Mellitus with Congenital Hypothyroidism; Permanent Neonatal Diabetes Mellitus; Permanent Neonatal Diabetes with Neurologic Features, Transient Neonatal Diabetes Mellitus 1, Transient Neonatal Diabetes Mellitus 2, and Transient Neonatal Diabetes Mellitus 3.

"Identifying" or "selecting a subject having a metabolic or cardiovascular disease" means identifying or selecting a subject having been diagnosed with a metabolic disease, a cardiovascular disease, or a metabolic syndrome; or, identifying or selecting a subject having any one or more symptoms of a metabolic disease, cardiovascular disease, or metabolic syndrome including, but not limited to, hypercholesterolemia, hyperglycemia, hyperlipidemia, hypertriglyceridemia, hypertension increased insulin resistance, decreased insulin sensitivity, above normal body weight, and/or above normal body fat content or any combination thereof. Such identification may be accomplished by any method, including but not limited to, standard clinical tests or assessments, such as measuring serum or circulating (plasma) cholesterol, measuring serum or circulating (plasma) blood-glucose, measuring serum or circulating (plasma) triglycerides, measuring blood-pressure, measuring body fat content, measuring body weight, and the like.

"Improved cardiovascular outcome" means a reduction in the occurrence and/or severity of adverse cardiovascular events, or symptoms, or the risk thereof. Examples of adverse cardiovascular events include, without limitation, death, myocardial infarction whether the first one or reinfarction, stroke, cardiogenic shock, pulmonary edema, heart failure readmissions (for example, hospitalization for heart failure, defined as the unexpected presentation to an acute care facility requiring overnight stay with symptoms and physical examination findings consistent with heart failure, reduced tolerance to exercise, and treatment with intravenous vasodilators, inotropes, mechanical fluid removal, or hemodynamic support), lowering of left ventricular ejection fraction (LVEF), ventricular arrhythmias, cardiac arrest, and atrial dysrhythmia (for example, atrial fibrillation).

"Individual" or "subject" or "mammal" means a human or non-human mammal selected for treatment or therapy.

"Intravenous administration" means administration into a vein.

"Left Ventricular Diastolic Dysfunction (LVDD)" is a precursor diabetic cardiomyopathy in subjects with Type 2 or Type 1 diabetes.

"Mammal" or "mammalian" refers to a human or non-human mammal, including, but not limited to, mice, rats, rabbits, dogs, cats, pigs, and non-human primates, including, but not limited to, monkeys and chimpanzees.

"Nucleic acid" refers to molecules composed of monomeric nucleotides. A nucleic acid includes ribonucleic acids (RNA), deoxyribonucleic acids (DNA), single-stranded nucleic acids, double-stranded nucleic acids, small interfering ribonucleic acids (siRNA), and microRNAs (miRNA). A nucleic acid can also comprise a combination of these elements in a single molecule.

"Parenteral administration" means administration by a manner other than through the digestive tract. Parenteral administration includes topical administration, subcutaneous administration, intravenous administration, intramuscular administration, intraarterial administration, intraperitoneal administration, or intracranial administration, e.g. intrathecal or intracerebroventricular administration. Administration can be continuous, or chronic, or short or intermittent.

"Patient" or "Subject" are used interchangeably and for the purposes of the present invention includes humans and other animals, particularly mammals, and other organisms. Thus the methods are applicable to both human therapy and veterinary applications. More specifically, the patient is a mammal, and in some embodiments, the patient or subject is human.

"Pharmaceutical composition" means a mixture of substances suitable for administering to an individual. For example, a pharmaceutical composition can comprise one or more active agents and a sterile aqueous solution.

"Pharmaceutically acceptable carrier" means a medium or diluent that does not interfere with the structure or function of the oligonucleotide. Certain, of such carries enable pharmaceutical compositions to be formulated as, for example, tablets, pills, dragees, capsules, liquids, gels, syrups, slurries, suspension and lozenges for the oral ingestion by a subject. Certain of such carriers enable pharmaceutical compositions to be formulated for injection or infusion. For example, a pharmaceutically acceptable carrier can be a sterile aqueous solution.

"Pharmaceutically acceptable salts" means physiologically and pharmaceutically acceptable salts of antisense compounds, i.e., salts that retain the desired biological activity of the parent oligonucleotide and do not impart undesired toxicological effects thereto.

"Pharmaceutically effective amount" for purposes herein is thus determined by such considerations as are known in the art, and may also include "therapeutically effective amounts" (also used synonymously) which is broadly used herein to mean an amount of any miR-126 containing agent, that when administered to a patient, ameliorates, diminishes, improves or prevents a symptom of cardiovascular disorder or disease in a patient who has suffered a stroke, and who may or may not have a glucose metabolism disorder. The amount of the miR-126 containing agent described herein, or their internal components which constitutes a "therapeutically effective amount," will vary depending on the agent density, the disease state and its severity, the age of the patient to be treated, and the like.

Accordingly, a "therapeutically effective amount" refers to an amount effective, at dosages and for periods of time necessary, to achieve the desired therapeutic result to thereby influence the therapeutic course of a particular disease state. A therapeutically effective amount of a miR-126 containing agent may vary according to factors such as the disease state, age, sex, and weight of the individual, and the ability of the agent to elicit a desired response in the individual. Dosage regimens may be adjusted to provide the optimum therapeutic response. A therapeutically effective amount is also one in which any toxic or detrimental effects of the agent are outweighed by the therapeutically beneficial effects. In another embodiment, the active agent is formulated in the composition in a prophylactically effective amount.

"Prevent" refers to delaying or forestalling the onset or development of a cardiovascular disease, disorder, or condition for a period of time from minutes to indefinitely. Prevent also means reducing risk of developing a cardiovascular disease, disorder, or condition. "Prevent" or "preventing" or "prevention" shall be taken to mean administering an amount of miR-126 containing agent, or soluble factors derived therefrom and stopping or hindering or delaying the development or progression of a cardiovascular disease, disorder or symptom following a cerebrovascular injury, for example, a stroke. "Prevent" or "preventing" or "prevention" refers to prevention or delay of the onset of the cardiovascular disorder or disease, and/or a decrease in the level of discomfort, general malaise, or persistence of cardiovascular disorder and/or disease symptoms in a subject relative to the symptoms that would develop and/or persist in the absence of the methods of the invention. The prevention can be complete, e.g., the total absence of cardiovascular disorder or disease symptoms. The prevention can also be partial, such that the occurrence of cardiovascular disorder or disease symptoms in a subject is less than that which would have occurred without the present invention.

"Shortening fraction (SF)" is a term that refers to an alternate method of measuring left ventricle function when only the ventricular diameters are known.

"Stroke" shall be taken to mean loss of brain function(s), usually rapidly developing, that is due to a disturbance in blood flow to the brain or brainstem. The disturbance can be ischemia (lack of blood) caused by, e.g., thrombosis or embolism, or can be due to a hemorrhage. In one example, the loss of brain function is accompanied by neuronal cell death. In one example, the stroke is caused by a disturbance or loss of blood from to the cerebrum or a region thereof. In one example, a stroke is a neurological deficit of cerebrovascular cause that persists beyond 24 hours or is interrupted by death within 24 hours (as defined by the World Health Organization). Persistence of symptoms beyond 24 hours separates stroke from Transient Ischemic Attack (TIA), in which symptoms persist for less than 24 hours. Symptoms of stroke include hemiplegia (paralysis of one side of the body); hemiparesis (weakness on one side of the body); muscle weakness of the face; numbness; reduction in sensation; altered sense of smell, sense of taste, hearing, or vision; loss of smell, taste, hearing, or vision; drooping of an eyelid (ptosis); detectable weakness of an ocular muscle; decreased gag reflex; decreased ability to swallow; decreased pupil reactivity to light; decreased sensation of the face; decreased balance; nystagmus; altered breathing rate; altered heart rate; weakness in sternocleidomastoid muscle with decreased ability or inability to turn the head to one side; weakness in the tongue; aphasia (inability to speak or understand language); apraxia (altered voluntary movements); a visual field defect; a memory deficit; hemineglect or hemispatial neglect (deficit in attention to the space on the side of the visual field opposite the lesion); disorganized thinking; confusion; development of hypersexual gestures; anosognosia (persistent denial of the existence of a deficit); difficulty walking; altered movement coordination; vertigo; disequilibrium; loss of consciousness; headache; and/or vomiting. The term "stroke" as used herein is meant to include ischemic stroke and brain hemorrhage stroke, including ICH (intracerebral hemorrhage) and SAH (Subarachnoid Hemorrhage).

"Treat" or "treatment" or "treating" shall be understood to mean administering an amount of miR-126 containing agent, or soluble factors derived therefrom and reducing the severity of a cardiovascular disorder or disease to a subject that has suffered a cerebrovascular injury, for example a stroke.

"Type 2 diabetes" (also known as "type 2 diabetes mellitus" or "diabetes mellitus, type 2", and formerly called "diabetes mellitus type 2", "non-insulin-dependent diabetes (NIDDM)", "obesity related diabetes", or "adult-onset diabetes") is a metabolic disorder that is primarily characterized by insulin resistance, relative insulin deficiency, and hyperglycemia.

As used herein, the term "normal or healthy individual" shall be taken to mean a subject who has not suffered a stroke.

"Prophylactically effective amount" refers to an amount effective, at dosages and for periods of time necessary, to achieve the desired prophylactic result. Typically, since a prophylactic dose or amount is used in subjects prior to or at an earlier stage of disease, the prophylactically effective amount will be less than the therapeutically effective amount.

As used herein, the term "suffer" as in "suffered a stroke" or "suffer a stroke" means a subject or patient who has deprived blood supply to the brain, or has compressed brain tissue, owing to an obstruction of blood vessels, arterial stenosis, or ruptured blood vessels, and consequently or coincidentally has a one or more of the cardiovascular diseases or disorders enumerated above or is likely to develop one or more of the cardiovascular diseases or disorders enumerated above.

As used herein, miR-126 can include miR-126 microRNAs (miRNAs or miRs), for example, a mammalian miR-126. miRNAs are generally considered as short RNAs (20-24 nt) that can be involved the regulation of gene expression via their effect on mRNA stability and translation of the target mRNA. In some embodiments, an illustrative miR-126 is human miR-126 (full name "microRNA 126"), as provided in NCBI accession no. NR_029695.1 (>NR_029695.1 *Homo sapiens* microRNA 126 (hsa-miR-126) (miR-126)) CGCTGGCGACGGGACATTAT-TACTTTTGGTACGCGCTGTGACACTTCAAA CTCGTACCGTGAGTAATAATGCGCCGTCCACGGCA (SEQ ID NO: 2). (Chen et al., MiR-126 Affects Brain-Heart Interaction (2017) Transl. Stroke Res. 2017 August; 8(4): 374-385, the disclosure of which is incorporated herein by reference in its entirety). MiR-126 and/or an analog thereof can be synthesized and transcribed in vitro using a DNA template, or transcribed in vivo from an engineered miRNA precursor.

miRNAs are sometimes transcribed as longer primary mRNA transcripts called a pre-miR. The pre-miR is subsequently processed to yield a mature miR. As used herein, miR-126 can also refer to pre-miR-126, including, but not limited to *Homo sapiens* pre-miR-126. *Homo sapiens* pre-miR-126 can comprise the nucleotide (RNA) sequence: CGCUGGCGACGGGACAUUAUUACUUUUG- GUACGCGCUGUGACACUUCAAACUCG UACCGUG- AGUAAUAAUGCGCCGUCCACGGCA (SEQ ID NO: 3).

The *Homo sapiens* pre-miR-126 RNA sequence can be encoded by a *Homo sapiens* pre-miR-126 DNA sequence, which can comprise the nucleotide (DNA) sequence (SEQ ID NO: 2)
CGCTGGCGACGGGACATTATTACTTTTGGTACGCGCTGTGACACTTCAAAC

TCGTACCGTGAGTAATAATGCGCCGTCCACGGCA.

As used herein, miR-126 can also refer to a mature miR-126. An example of a mature miR-126 is mature *Homo sapiens* miR-126, which can comprise the nucleotide (RNA) sequence: UCGUACCGUGAGUAAUAAUGCG (SEQ ID NO: 1). The mature *Homo sapiens* miR-126 can be encoded by a mature *Homo sapiens* miR-126 DNA sequence, which can comprise the nucleotide (DNA) sequence: TCGTACCGTGAGTAATAATGCG (SEQ ID NO: 4).

As used herein, miR-126 can also refer to miR-126*, the complement of mature miR-126. An example of a miR-126* is *Homo sapiens* miR-126*, which can comprise the nucleotide (RNA) sequence: CAUUAUUACUUUUGGUACGCG (SEQ ID NO: 5). *Homo sapiens* miR-126 can be encoded by the *Homo sapiens* miR-126 DNA sequence, which can comprise the nucleotide (DNA) sequence: CATTATTACTTTTGGTACGCG (SEQ ID NO: 6).

Compositions

In some embodiments, without limitation, the methods described herein can utilize compositions and/or formulations containing a miRNA-126 containing agent such as an extracellular vesicle, for example, an exosome or a microvesicle containing miR-126. In some embodiments, a miR-126 containing agent can include miR-126 RNA, human cells that are operable to synthesize miR-126 microRNA, human cells that are induced to synthesize miR-126 microRNA, particles containing miR-126 for example, exosomes, microvesicles, liposomes, microparticles, nanoparticles, or other common vehicles for delivery of nucleic acid commonly known in the art. In all of these compositions referred to above, miR-126 containing agents contain a miR-126 microRNA containing a nucleotide sequence of SEQ ID NO: 1, or an analog thereof.

In some embodiments, miR-126 containing agents can include particles derived from living cells, for example mammalian cells. In some embodiments, mammalian cells include cells that are known to produce exosomes, and microvesicles, for example, stem cells, endothelial cells, mesenchymal stromal cells, umbilical cord cells, endothelial cells, cerebral endothelial cells, brain microvascular endothelial cells, Primary Human Brain Microvascular Endothelial Cells (ACBRI 376), endothelial progenitor cells, AC-133/CD-133+ cells and the like, Schwann cells, hematopoietic cells, reticulocytes, monocyte-derived dendritic cells (MDDCs), monocytes, macrophages, B lymphocytes, antigen-presenting cells, glial cells, astrocytes, neurons, oligodendrocytes, spindle neurons, microglia, mastocytes, hemangioblast cells, lymphoid progenitor cells, myeloid progenitor cells, vascular stem cells, endothelial progenitor cells, pericytes, hematopoietic stem cells, endothelial progenitor cells, human umbilical cord blood cells (HUCBCs), or CD133+/KDR+ cells.

An illustrative example of a miR-126 containing agent are extracellular vesicles, including, but not limited to exosomes, microvesicles (also known as ectosomes, shedding vesicles, microparticles, plasma membrane-derived vesicles, and exovesicles), and apoptotic bodies. (D. Ha, et al. "Exosomes as therapeutic drug carriers and delivery vehicles across biological membranes: current perspectives and future challenges" (2016) Acta Pharmaceutica Sinica B, Vol 6, Issue 4, p. 287-296, the disclosure of which is incorporated herein by reference in its entirety). miRNA containing agents such as exosomes (size <100 nm), microvesicles (size <1000 nm) and apoptotic bodies (size 1-4 μm), are small extracellular vesicles released from cells, which have been shown to carry nucleic acids including microRNAs (Yu et al. Exosomes as miRNA Carriers: Formation-Function-Future, Int J Mol Sci. 2016 December; 17(12): 2028, the disclosure of which is incorporated herein by reference in its entirety). In various embodiments, methods provided herein for the treatment of a cardiovascular disease or disorder in a subject having suffered a cerebrovascular injury, for example, a stroke, include administering a therapeutically effective dose or amount of an miR-126 containing agent to the subject in need thereof. In some embodiments, the miR-126 containing agent can be administered without the addition of any further excipient, carrier or diluent, or in the form of a composition containing the miR-126 containing agent admixed with one or more excipients, carriers or diluents. In various embodiments, the compositions may include non-pharmaceutical compositions or pharmaceutical compositions approved for administration to a subject, for example a human subject. In all of these examples, the miR-126 containing agent may include naked miR-126 microRNA, a human or non-human cell expressing or capable of expressing miR-126 microRNA, a vesicle containing miR-126 microRNA, or a particle containing miR-126 microRNA, or agents which induce the expression of miR-126 at the target tissue.

As used herein, in some embodiments, miR-126 containing agents can include miR-126 microRNA. In some of these embodiments, methods for isolating miR-126 microRNA are known in the art. In one example, miR-126 can be produced using general, known molecular biology techniques taking advantage of the nucleotide sequence of miR-126 as shown in SEQ ID NO: 1. For example, a cDNA molecule encoding the complementary sequence of miR-126 microRNA can be cloned into a plasmid and serve as a template for polymerase chain reactions (PCR) for the synthesis of miR-126 which can then be reverse transcribed to RNA. Other methods for isolating miR-126 from biological fluids are also known, for example, Lekchnov, E. A., Anal Biochem. (2016), "Protocol for miRNA isolation from biofluids", 499:78-84.

Alternatively, miR-126 can be synthesized from the nucleotide sequence of miR-126 as provided in SEQ ID NO: 1.

In other embodiments, miR-126 containing agents also include natural and synthetic nucleic acid vectors (for example, plasmids, cosmids, YACs, and viral vectors) that contain a miR-126 nucleic acid sequence (for example, a polynucleotide containing the nucleotide sequence of SEQ ID NO: 1) and which also contain expression sequences such as promoters, termination signals and other transcription and translation signals operable to express the miR-126 microRNA in its intended cells and tissues.

In various embodiments, miR-126 microRNA molecules may be encoded in a target tissue, for example, the vascular endothelium or cells of the heart tissue, e.g. cardiomyocytes by a nucleic acid molecule comprised in a vector. The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques, which are described in Sambrook et al., 1989 and Ausubel et al., 1996, both incorporated herein by reference. In addition to encoding a miR-126 microRNA, a vector may encode a targeting molecule. A targeting molecule is one that directs the desired nucleic acid to a particular organ, tissue, cell, or other location in a subject's body.

The term "expression vector" refers to a vector containing a nucleic acid sequence coding for at least part of a gene product capable of being transcribed. Expression vectors can contain a variety of "control sequences," which refer to nucleic acid sequences necessary for the transcription of an operably linked coding sequence in a particular host organism. In addition to control sequences that govern transcription and translation, vectors and expression vectors may contain nucleic acid sequences that serve other functions as well and are described. There are a number of ways in which expression vectors may be introduced into cells. In certain embodiments of the invention, the expression vector comprises a virus or engineered vector derived from a viral genome. The ability of certain viruses to enter cells via receptor-mediated endocytosis, to integrate into host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986). The first viruses used as gene vectors were DNA viruses including the papovaviruses (simian virus 40, bovine papilloma virus, and polyoma) (Ridgeway, 1988; Baichwal and Sugden, 1986) and adenoviruses (Ridgeway, 1988; Baichwal and Sugden, 1986). These have a relatively low capacity for foreign DNA sequences and have a restricted host spectrum. They can accommodate up to 8 kb of foreign genetic material but can be readily introduced in a variety of cell lines and laboratory animals (Nicolas and Rubenstein, 1988; Temin, 1986). The retroviruses are a group of single-stranded RNA viruses characterized by an ability to convert their RNA to double-stranded DNA in infected cells; they can also be used as vectors. Other viral vectors may be employed as expression constructs in the present invention. Vectors derived from viruses such as vaccinia virus (Ridgeway, 1988; Baichwal and Sugden, 1986; Coupar et al., 1988) adeno-associated virus (AAV) (Ridgeway, 1988; Baichwal and Sugden, 1986; Hermonat and Muzycska, 1984) and herpesviruses may be employed. They offer several attractive features for various mammalian cells (Friedmann, 1989; Ridgeway, 1988; Baichwal and Sugden, 1986; Coupar et al., 1988; Horwich et al., 1990).

Other suitable methods for nucleic acid delivery to effect expression of compositions of the present invention are believed to include virtually any method by which a nucleic acid (e.g., RNA, or DNA, including viral and nonviral vectors) can be introduced into an organelle, a cell, a tissue or an organism, as described herein or as would be known to one of ordinary skill in the art. Such methods include, but are not limited to, direct delivery of RNA such as by injection (U.S. Pat. Nos. 5,994,624; 5,981,274; 5,945,100; 5,780,448; 5,736,524; 5,702,932; 5,656,610; 5,589,466 and 5,580,859, each incorporated herein by reference), including microinjection (Harlan and Weintraub, 1985; U.S. Pat. No. 5,789,215, incorporated herein by reference); by electroporation (U.S. Pat. No. 5,384,253, incorporated herein by reference); by calcium phosphate precipitation (Graham and Van Der Eb, 1973; Chen and Okayama, 1987; Rippe et al., 1990); by using DEAE-dextran followed by polyethylene glycol (Gopal, 1985); by direct sonic loading (Fechheimer et al., 1987); by liposome mediated transfection (Nicolau and Sene, 1982; Fraley et al., 1979; Nicolau et al., 1987; Wong et al., 1980; Kaneda et al., 1989; Kato et al., 1991); by microprojectile bombardment (PCT Application Nos. WO 94/09699 and 95/06128; U.S. Pat. Nos. 5,610,042; 5,322,783; 5,563,055; 5,550,318; 5,538,877 and 5,538,880, and each incorporated herein by reference); by agitation with silicon carbide fibers (Kaeppler et al., 1990; U.S. Pat. Nos. 5,302,523 and 5,464,765, each incorporated herein by reference); by *Agrobacterium*-mediated transformation (U.S. Pat. Nos. 5,591,616 and 5,563,055, each incorporated herein by reference); or by PEG-mediated transformation of protoplasts (Omirulleh et al., 1993; U.S. Pat. Nos. 4,684,611 and 4,952,500, each incorporated herein by reference); by desiccation/inhibition-mediated DNA uptake (Potrykus et al., 1985). Through the application of techniques such as these, organelle(s), cell(s), tissue(s) or organism(s) may be stably or transiently transformed.

In other embodiments, an illustrative miR-126 containing agent can include a cell (e.g. a eukaryotic cell, for example, a human cell) that synthesizes and expresses miR-126. In some embodiments, cells can be administered that naturally produce miR-126, for example, human or non-human: stem cells, endothelial cells, stem cells, mesenchymal stromal cells, umbilical cord cells, endothelial cells, cerebral endothelial cells, brain microvascular endothelial cells, Primary Human Brain Microvascular Endothelial Cells (ACBRI 376), endothelial progenitor cells, AC-133/CD-133+ cells and the like, Schwann cells, hematopoietic cells, reticulocytes, monocyte-derived dendritic cells (MDDCs), monocytes, macrophages, B lymphocytes, antigen-presenting cells, glial cells, astrocytes, neurons, oligodendrocytes, spindle neurons, microglia, or mastocytes. In other embodiments, stem cells, endothelial cells, stem cells, mesenchymal stromal cells, umbilical cord cells, endothelial cells, cerebral endothelial cells, brain microvascular endothelial cells, Primary Human Brain Microvascular Endothelial Cells (ACBRI 376), endothelial progenitor cells, AC-133/CD-133+ cells and the like, Schwann cells, hematopoietic cells, reticulocytes, monocyte-derived dendritic cells (MDDCs), monocytes, macrophages, B lymphocytes, antigen-presenting cells, glial cells, astrocytes, neurons, oligodendrocytes, spindle neurons, microglia, or mastocytes cells may be transfected with purified miR-126 based on the nucleotide sequence of miR-126 as shown in SEQ ID NO:1. In an exemplary method, cells that may or may not naturally produce miR-126 can be transfected or transformed to produce miR-126, either constitutively or induced by adding an agent to a cell culture to induce production of miR-126 microRNA. For example, MicroRNA-126 (miR-126-3p) may be synthesized using the nucleotide sequence 5'-UCGUACCGUGAGUAAUAAUGCG-3' (SEQ ID NO: 1). Human umbilical vein endothelial cells (HUVECs) may transfected and assayed using quantitative real-time polymerase chain reaction (qRT-PCR). HUVECs may be cultured and transfected with miR-126-3p according to the manufacturer's instructions using the siPORT NeoFX Transfection Agent (Applied Biosystems Inc.). Briefly, HUVECs may be grown in DMEM with 10% Fetal Bovine Serum (CellGro) to 80% confluence at 37° C. and 5% $CO_2$. Adherent cells are washed and trypsinized. Trypsin can be inactivated by re-suspending the cells in DMEM with 10% FBS (Invitrogen). The SiPORT NeoFX transfection agent is diluted in Opti-MEM I medium (Life Technologies) and incubated for 10 minutes at room temperature. miR-126-3p can be diluted into 50 µL Opti-MEM I medium at a concentration of 30 nM. Diluted microRNA and diluted siPORT NeoFX Transfection agent is mixed and incubated for another 10 minutes at room temperature to allow transfection complexes to form and subsequently dispensed into wells of a clean 6-well culture plate. The HUVEC suspension is overlaid onto the transfection complexes and gently mixed to equilibrate. Transfected cells are incubated at 37° C. and 5% $CO_2$ for 24 hours. Cells other than HUVEC, for example, stem cells, endothelial cells, stem cells, mesenchymal stromal cells, umbilical cord cells, endothelial cells, cerebral endothelial cells, brain microvascular endothelial cells, Primary Human Brain Microvascular Endothelial Cells (ACBRI 376), endothelial progenitor cells, AC-133/CD-133+ cells and the like, Schwann cells, hematopoietic cells, reticulocytes, monocyte-derived dendritic cells (MDDCs), monocytes, macrophages, B lymphocytes, antigen-presenting cells, glial cells, astrocytes, neurons, oligodendrocytes, spindle neurons, microglia, or mastocytes may be used and transfected with miR-126 RNA as described above for HUVEC cells.

A miR-126 containing agent can be derived or isolated in a variety of ways. In some embodiments, an illustrative miR-126 containing agent may include exosomes and/or microvesicles containing miR-126. An exemplary exosome isolation method can be adapted from Thery C. In some non-limiting embodiments, a miR-126 containing agent can be loaded into an extracellular vesicle, e.g., an exosome. Moreover, miR-126 can be obtained for use in a miR-126 containing agent by either overexpression of miR-126 miRNA, or direct transfection and/or transformation of a host cell. For example, mammalian cells can be modified to engineer expression of miR-126 miRNA. Additionally, in some illustrative embodiments, mammalian cells can be transfected or transformed with nucleic acid vectors, introducing nucleic acids encoding miR-126. An illustrative example of miR-126 transfection includes, but is not limited to, obtaining pre-miRNA-126; plating cells on a suitable cell culture dish at 50% confluence; transfecting the pre-miR-126 using Lipofectamine (or any other suitable transfection agent); confirming transfection using quantitative-PCR; washing the cells twice with PBS; and extracting the miR-126 using conventional, commercially available techniques, such as the mirVana miRNA isolation kit with phenol (Thermo Fisher Scientific) (Hu et al., MicroRNAs 125a and 455 Repress Lipoprotein-Supported Steroidogenesis by Targeting Scavenger Receptor Class B Type I in Steroidogenic Cells, Mol Cell Biol. 2012 December; 32(24): 5035-5045, the disclosure of which is incorporated herein by reference in its entirety).

Exosomes and/or microvesicles can be transfected with miR-126 miRNA using common techniques known to those with ordinary skill in the art, and/or by using commercially available kits (e.g., Exo-fect Exosome Transfection Kit, System Biosciences). Furthermore, cells can be reprogrammed to express a miR-126 containing agent. An exemplary miRNA reprogramming method is illustrated by Trivedi et al., "Modification of tumor cell exosome content by transfection with wt-p53 and microRNA-125b expressing plasmid DNA and its effect on macrophage polarization", Oncogenesis. 2016 August; 5(8): e250, the disclosure of which is incorporated herein by reference in its entirety. In a non-limiting embodiment, a plasmid containing pre-miR-126 miRNA is isolated and purified. Next, hyaluronic acid-poly(ethylene imine) and hyaluronic acid (HA)-poly (ethylene glycol) (PEG) (HA-PEI/HA-PEG) blend nanoparticles are then obtained by combining 50 mg of maleimide-PEG-amine to 1-Ethyl-3-(3-dimethylaminopropyl)-carbodimide (EDC)/N-hydroxysuccinimide (NHS) activated HA, and dissolving the HA-PEI and HA-PEG solutions in PBS. Cells such as stem cells, endothelial cells, mesenchymal stromal cells, umbilical cord cells, endothelial cells, cerebral endothelial cells, brain microvascular endothelial cells, Primary Human Brain Microvascular Endothelial Cells (ACBRI 376), endothelial progenitor cells, AC-133/CD-133+ cells and the like, Schwann cells, hematopoietic cells, reticulocytes, monocyte-derived dendritic cells (MDDCs), monocytes, macrophages, B lymphocytes, antigen-presenting cells, glial cells, astrocytes, neurons, oligodendrocytes, spindle neurons, microglia, mastocytes, hemangioblast cells, lymphoid progenitor cells, myeloid progenitor cells, vascular stem cells, endothelial progenitor cells, pericytes, hematopoietic stem cells, endothelial progenitor cells, human umbilical cord blood cells (HUCBCs), CD133+/KDR+ cells, or any cell with an endomembrane system, can be plated and treated with a suitable amount of plasmid containing miR-126 (e.g., 1-20 µg) encapsulated in the nanoparticles. Finally, exosomes can be isolated using techniques described above, by using commercially available kits, or by taking cell supernatant from, and centrifuging at 2000 g for 30 min to remove cell debris; taking the supernatant and adding it to a commercially available exosome isolation reagent, followed by incubation overnight at 4° C.; further centrifuged at 10,000 g for 1 hour at 4° C.; and aspiration of the supernatant followed by resuspending the exosome pellet in sterile PBS.

Cells can be induced to release and/or secrete an miR-126 containing agent (e.g., exosomes and/or microvesicles) in response to a variety of signals including, but not limited to, cytokines, mitogens, and/or any other method of paracrine/autocrine signaling (see Saunderson et al., "Induction of Exosome Release in Primary B Cells Stimulated via CD40 and the IL-4 Receptor", J Immunol. 2008 Jun. 15; 180(12): 8146-52, the disclosure of which is incorporated herein by reference in its entirety).

In some non-limiting embodiments, cells can be induced to release and/or secrete exosomes and/or microvesicles by modulating intracellular calcium ($Ca^{2+}$) content. An exemplary illustrative technique for stimulating an miR-126 containing agent (e.g., an exosome and/or a microvesicle containing miR-126) is provided by Savina et al., "Exosome release is regulated by a calcium-dependent mechanism in K562 cells", the disclosure of which is incorporated herein by reference in its entirety. After selecting the suitable cell type, for example, but not limited to, stem cells, endothelial cells, mesenchymal stromal cells, umbilical cord cells, endothelial cells, cerebral endothelial cells, brain microvascular endothelial cells, Primary Human Brain Microvascular Endothelial Cells (ACBRI 376), endothelial progenitor cells, AC-133/CD-133+ cells and the like, Schwann cells, hematopoietic cells, reticulocytes, monocyte-derived dendritic cells (MDDCs), monocytes, macrophages, B lymphocytes, antigen-presenting cells, glial cells, astrocytes, neurons, oligodendrocytes, spindle neurons, microglia, mastocytes, hemangioblast cells, lymphoid progenitor cells, myeloid progenitor cells, vascular stem cells, endothelial progenitor cells, pericytes, hematopoietic stem cells, endothelial progenitor cells, human umbilical cord blood cells (HUCBCs), CD133+/KDR+ cells, or any one or more of the abovementioned cells, and/or any cell with an endomembrane system, a compound that influences $Na^+/H^+$ exchange and/or intracellular calcium ($Ca^{2+}$) content (e.g., an ionophore such a monesin), can be applied to stimulate miR-126 containing agent release (e.g. an exosome and/or a microvesicle). Subsequent to miR-126 containing agent stimulation, the exosomes and/or microvesicles can be isolated using any one of the techniques known to those with ordinary skill, and/or enumerated herein.

Some non-limiting embodiments may call for an miR-126 containing agent to be produced by stimulating and/or inducing overproduction of exosomes and/or microvesicles in either stem cells, endothelial cells, mesenchymal stromal cells, umbilical cord cells, endothelial cells, cerebral endothelial cells, brain microvascular endothelial cells, Primary Human Brain Microvascular Endothelial Cells (ACBRI 376), endothelial progenitor cells, AC-133/CD-133+ cells and the like, Schwann cells, hematopoietic cells, reticulocytes, monocyte-derived dendritic cells (MDDCs), monocytes, macrophages, B lymphocytes, antigen-presenting cells, glial cells, astrocytes, neurons, oligodendrocytes, spindle neurons, microglia, mastocytes, hemangioblast cells, lymphoid progenitor cells, myeloid progenitor cells, vascular stem cells, endothelial progenitor cells, pericytes, hematopoietic stem cells, endothelial progenitor cells, human umbilical cord blood cells (HUCBCs), CD133+/KDR+ cells, or any one or more of the abovementioned cells, and/or any cell with an endomembrane system, that has been transformed or transfected to overexpress miR-126 miRNA, using techniques known to those with ordinary skill, and/or enumerated herein, for example as provided in: Amigorena S, Raposo G, ClaytonA: "Isolation and characterization of exosomes from cell culture supernatants and biological fluids". Curr. Protoc. Cell Biol. 2006 April; Chapter 3: Unit 3.22, the disclosure of which is incorporated herein by reference in its entirety. Typically, 100 mL of cultured media is used by pooling from multiple dishes. The media is centrifuged at 300×g for 10 min at 4° C. to remove any intact cells, followed by a 2,000×g spin for 20 min at 4° C. to remove dead cells and finally a 10,000×g spin for 30 min at 4° C. to remove cell debris. The media is then transferred to ultracentrifuge tubes and centrifuged at 100,000×g for at least 60 min at 4° C. in Optima TLX ultracentrifuge with 60 Ti rotor (Beckman Coulter, Mississauga, Canada). The supernatant containing exosome-free media is removed and the pellets containing exosomes plus proteins from media are resuspended in PBS. The suspension is centrifuged at 100,000×g for at least 60 min at 4° C. to collect final exosome pellets. The exosome pellet is then resuspended in an appropriate excipient or diluent in a desired volume to attain a specific concentration of exosomes per mL.

Exosomes may also be isolated using any of the techniques described by Willis et al., Toward Exosome-Based Therapeutics: Isolation, Heterogeneity, and Fit-for-Purpose Potency (2017) Front Cardiovasc Med. 4: 63, the disclosure of which is incorporated herein by reference in its entirety. Such isolation methods include Ultracentrifugation (i.e., 100,000-120,000×g); size-exclusion chromatography; commercially available isolation kits (e.g. ExoQuick and ExoE-LISA); and CD63 capture (exosome) ELISA, (Systems Biosciences, CA, USA).

An exemplary microvesicle isolation method can be adapted from R. Szatanek et al. Isolation of extracellular vesicles: Determining the correct approach (2015) Int J Mol Med. 2015 July; 36(1): 11-17, the disclosure of which is incorporated herein by reference in its entirety. Typically, for differential centrifugation/ultracentrifugation, intact cells, dead cells and cell debris are removed by centrifuging at 300×g for 10 min, 2,000×g for 10 min and 10,000×g for 30 min, respectively. Supernatant is transferred into a new test tube while the generated pellets are being discarded. After the 10,000×g spin, the supernatant is then subjected to a final ultracentrifugation at 100,000×g for 70 min, all centrifugation steps carried out at 4° C.

Exemplary methods for isolating apoptotic bodies from cells and tissues are well known in the art, and are illustratively provided in U.S. Patent Application Publication No. 2016/0290996, Ser. No. 15/037,301, filed on Oct. 6, 2016, the disclosure of which is incorporated herein by reference in its entirety.

In some embodiments, without limitation, the methods described herein can utilize compositions and/or formulations containing exosomes derived from a variety of exosome producing mammalian cells, for example, stem cells, stem cells, endothelial cells, stemcells, mesenchymal stromal cells, umbilical cord cells, endothelial cells, cerebral endothelial cells, brain microvascular endothelial cells, Primary Human Brain Microvascular Endothelial Cells (ACBRI 376), endothelial progenitor cells, AC-133/CD-133+ cells and the like, Schwann cells, hematopoietic cells, reticulocytes, monocyte-derived dendritic cells (MDDCs), monocytes, macrophages, B lymphocytes, antigen-presenting cells, glial cells, astrocytes, neurons, oligodendrocytes, spindle neurons, microglia, or mastocytes. In various embodiments, miR-126 containing compositions of the present disclosure may contain exosomes or exosome constituents, i.e. exosome contents derived from exosomes harvested or isolated from cells such as stem cells, stem cells, endothelial cells, stem cells, mesenchymal stromal cells, umbilical cord cells, endothelial cells, cerebral endothelial cells, brain microvascular endothelial cells, Primary Human Brain Microvascular Endothelial Cells (ACBRI 376), endothelial progenitor cells, AC-133/CD-133+ cells and the like, Schwann cells, hematopoietic cells, reticulocytes, monocyte-derived dendritic cells (MDDCs), monocytes, macrophages, B lymphocytes, antigen-presenting cells, glial cells, astrocytes, neurons, oligodendrocytes, spindle neurons, microglia, or mastocytes.

In some embodiments, without limitation, the methods described herein can utilize compositions and/or formulations containing exosomes and/or microvesicles derived from a variety of exosome and/or microvesicle producing mammalian cells. In various embodiments, compositions of the present disclosure may contain exosomes, and/or microvesicles, or exosome constituents, from stem cells, endothelial cells, mesenchymal stromal cells, umbilical cord cells, endothelial cells, cerebral endothelial cells, brain microvascular endothelial cells, Primary Human Brain Microvascular Endothelial Cells (ACBRI 376), endothelial progenitor cells, AC-133/CD-133+ cells and the like, Schwann cells, hematopoietic cells, reticulocytes, monocyte-derived dendritic cells (MDDCs), monocytes, macrophages, B lymphocytes, antigen-presenting cells, glial cells, astrocytes, neurons, oligodendrocytes, spindle neurons, microglia, mastocytes, hemangioblast cells, lymphoid progenitor cells, myeloid progenitor cells, vascular stem cells, endothelial progenitor cells, pericytes, hematopoietic stem cells, endothelial progenitor cells, human umbilical cord blood cells (HUCBCs), or CD133+/KDR+ cells.

In various embodiments, miR-126 containing agents include cells which are operable to synthesize miR-126, for example, hematopoietic stem cells, endothelial progenitor cells or CD133+/KDR+ human umbilical cord blood cells (HUCBCs). In various embodiments, miR-126 containing agents include exosomes derived or isolated from cells which are operable to synthesize miR-126, for example, hematopoietic stem cells, endothelial progenitor cells or CD133+/KDR+ human umbilical cord blood cells (HUCBCs). In various embodiments, miR-126 containing agents include microvesicles derived or isolated from cells which are operable to synthesize miR-126, for example, hematopoietic stem cells, endothelial progenitor cells or CD133+/KDR+ human umbilical cord blood cells (HUCBCs).

In some embodiments, the miR-126 containing agent useful in the compositions and methods of the present disclosure are exosomes and/or microvesicles derived from hematopoietic stem cells, endothelial progenitor cells or CD133+/KDR+ human umbilical cord blood cells (HUCBCs). Hematopoietic stem cells, endothelial progenitor cells or CD133+/KDR+ human umbilical cord blood cells (HUCBCs) can be obtained via primary cell culture, or through commercial vendors. For example, human umbilical cord-derived mesenchymal stem cells are commercially available from the American Type Culture Collection (ATCC), Manassas, Va., USA.

An exemplary CD133+/KDR+ HUCBCs isolation method can be adapted from Steurer et al., Quantification of circulating endothelial and progenitor cells: comparison of quantitative PCR and four-channel flow cytometry (2008) BMC Res Notes. 1: 71, the disclosure of which is incorporated herein by reference in its entirety. Typically, blood is acquired from patients, or, human umbilical cord blood is obtained from full-term newborns. The blood samples are collected in heparinized tubes and stored at 8° C., for a period not to exceed 12 hours. Next, mononuclear cells may be isolated by Ficoll density gradient centrifugation, and progenitor cells are enriched via a two-step immunomagnetic bead separation protocol—negatively selecting against CD45, and then positively selecting for positive selection for CD133+.

Alternatively, another exemplary CD133+/KDR+ HUCBCs isolation method using flow cytometry detection and enumeration can be adapted from Duda et al., "A protocol for phenotypic detection and enumeration of circulating endothelial cells and circulating progenitor cells in human blood", (2007) Nat. Protoc. 2(4): 805-810, the disclosure of which is incorporated herein by reference in its entirety. Here, blood is obtained and immunostained by first centrifuging the sample at 700 g for 20 min at 4° C. with no brake. Next, plasma is gently removed with a 5 ml pipette, and stored in separate tubes at 0.25 mL aliquots. The lower phase containing blood cells is resuspended using 10 mL of cold 1×PBS containing 0.5% (w/v) BSA and 1.5 mM EDTA, followed by centrifugation at 700 g for 20 min at 4° C. with no brake. Next, the upper phase is removed and discarded, and the remaining cell pellet is resuspended by gentle pipetting or vortexing, and 2.5 mL is transferred into a separate tube and kept on ice. FcR-blocking agent is then added at a concentration of 1 µg mL$^{-1}$, and the samples are incubated on ice for 10 min. Next, 500 µL of the samples are distributed into one isotype control and three sample tubes, and the antibodies of interest are added. Here, 4 µL of IgG-FITC, 5 µL of IgG-PE, 10 µL of IgG-PerCP and 3 µL of IgG-APC can be used for control antibodies, and 5 µL of CD133-FITC antibody (ThermoFisher Scientific, Carlsbad, Calif. USA) and 5 µL Human VEGF R2/KDR/Flk-1 PE-conjugated Antibody (R&D Systems, Minneapolis, Minn., USA) can be used as the experimental antibodies (Note: antibody use may require normal optimization techniques). It is recommended that single color controls are used to set up the compensation matrix during the first run. Subsequently, tubes 1 and 2 can be used to confirm compensation. Cell viability can be assessed using conventional techniques such as monomeric cyanine dyes or DNA intercalator PI (Duda et al.). After addition of antibodies, the samples are vortexed briefly and incubated for 30 min at 4° C. or on ice, and in the dark. 9 mL of ACK lysing buffer is added and the samples are vortexed briefly, and then incubated at room temperature (18-25° C.) for 3 min (do not lyse cells for more than 3-5 min). Flow cytometry is performed by setting the gate on the mononuclear populations, in order to avoid red blood cells, platelets, cell debris and/or neutrophil contamination. Duda et al. recommends the use of Cell Preparation Tubes (CPT) to recover mononuclear cells. Collect 100,000-150,000 events in the mononuclear cell gate.

Formulations

Methods for preparing a formulation of miR-126 containing agents are known, and/or are readily apparent to those skilled in the art. An exemplary formulation method can be adapted from Remington's Pharmaceutical Sciences (17th Ed., Mack Pub. Co. 1985); Remington: Essentials of Pharmaceutics (Pharmaceutical Press, 2012), the disclosure of which is incorporated herein by reference in its entirety. Methods for formulating a nucleic acid, for example, miR-126 and a pharmaceutically acceptable vehicle, carrier, or excipient for the delivery of nucleic acids are provided in U.S. Patent Application Publication No. US 2013/0017223A1, Ser. No. 13/516,335, filed on Dec. 17, 2016, the disclosure of which is incorporated herein by reference in its entirety. Methods for formulating a pharmaceutically acceptable vehicle, carrier, or excipient for the delivery of miRNA are provided in U.S. Pat. No. 9,301,969B2, Ser. No. 13/822,641, filed on Sep. 9, 2011, the disclosure of which is incorporated herein by reference in its entirety. Methods for preparing a formulation of exosomes containing an agent are provided in U.S. Patent Application Publication No. US 2013/0156801A1, Ser. No. 13/327,244, filed on Dec. 15, 2011, the disclosure of which is incorporated herein by reference in its entirety. Furthermore, methods for preparing formulations for the exosome mediated delivery of biotherapeutics are provided in World Intellectual Property Organization Patent Application Publication No. WO 2013/084000 A2, filed on Dec. 7, 2012, the disclosure of which is incorporated herein by reference in its entirety; and U.S. Patent Application Publication No. US 2016/0346334 A1, Ser. No. 15/116,579, filed on Feb. 5, 2015, the disclosure of which is incorporated herein by reference in its entirety.

In some embodiments, without limitation, the methods described herein can utilize formulations containing one or more isolated miR-126 containing agents that are contained within a pharmaceutically acceptable vehicle, carrier, adjuvants, additives and/or excipient that allows for storage and handling of the agents before and during administration. Moreover, in accordance with certain aspects of the present invention, the agents suitable for administration may be provided in a pharmaceutically acceptable vehicle, carrier, or excipient with or without an inert diluent. Further, in addition to the above-described components, the formulation may contain additional lubricants, emulsifiers, suspending-agents, preservatives, or the like. Accordingly, the pharmaceutically acceptable vehicle, carrier, adjuvants, additives and/or excipient must be acceptable in the sense of being compatible with the other ingredients of the formulation and not deleterious to the recipient thereof, i.e., are sterile compositions and contain pharmaceutically acceptable vehicle, carrier, adjuvants, additives that are approved by the US Food and Drug Administration (FDA) for administration to a human subject.

Formulations containing exosomes and/or microvesicles containing miR-126 may be prepared with one or more carriers, excipients, and diluents. Exemplary carriers, excipients and diluents can include one or more of sterile saline, phosphate buffers, Ringer's solution, and/or other physiological solutions that are used in the preparation of cellular therapies for administration in humans. An exemplary method for generating formulations containing exosomes is illustrated by Li et al., "Exosomes Derived From Human Umbilical Cord Mesenchymal Stem Cells Alleviate Liver Fibrosis". Stem Cells Dev. 2013; 22:845-854, and Qiao et al., "Human mesenchymal stem cells isolated from the umbilical cord", Cell Biol Int. 2008 January; 32(1):8-15. Epub 2007 Aug. 19, the disclosures of which are incorporated herein by reference in its entirety.

In certain embodiments, formulations comprising one or more miR-126 containing agents can contain further additives including, but not limited to, pH-adjusting additives, osmolarity adjusters, tonicity adjusters, anti-oxidants, reducing agents, and preservatives. Useful pH-adjusting agents include acids, such as hydrochloric acid, bases or buffers, such as sodium lactate, sodium acetate, sodium phosphate, sodium citrate, sodium borate, or sodium gluconate. Further, the compositions of the invention can contain microbial preservatives. Useful microbial preservatives include methylparaben, propylparaben, and benzyl alcohol. The microbial preservative is typically employed when the formulation is placed in a vial designed for multidose use. Other additives that are well known in the art include, e.g., detackifiers, anti-foaming agents, antioxidants (e.g., ascorbyl palmitate, butyl hydroxy anisole (BHA), butyl hydroxy toluene (BHT) and tocopherols, e.g., .alpha.-tocopherol (vitamin E)), preservatives, chelating agents (e.g., EDTA and/or EGTA), viscomodulators, tonicifiers (e.g., a sugar such as sucrose, lactose, and/or mannitol), flavorants, colorants, odorants, opacifiers, suspending agents, binders, fillers, plasticizers, lubricants, and mixtures thereof. The amounts of such additives can be readily determined by one skilled in the art, according to the particular properties desired. Further, the formulation may comprise different types of carriers suitable for liquid, solid, or aerosol delivery.

In certain non-limiting embodiments, a formulation can be made by suspending an miR-126 containing agent in a physiological buffer with physiological pH, for example, a sterile buffer solution such as phosphate buffer solution (PBS); sterile 0.85% NaCl solution in water; or 0.9% NaCl solution in Phosphate buffer having KCl. Physiological buffers (i.e., a 1×PBS buffer) can be prepared, for example, by mixing 8 g of NaCl; 0.2 g of KCl; 1.44 g of $Na_2HPO_4$; 0.24 g of $KH_2PO_4$; then, adjusting the pH to 7.4 with HCl; adjusting the volume to 1 L with additional distilled $H_2O$; and sterilizing by autoclaving.

Another non-limiting embodiment may call for a formulation containing an miR-126 containing agent to be combined with a biological fluid such as blood, nasal secretions, saliva, urine, breast milk, cerebrospinal fluid, and/or any other natural matrix that represents a minimalist processing step (i.e., a step/storage component that reduces the possibility of influencing an miR-126 containing agent surface characteristic and/or behavior/integrity upon introduction to the subject/patient); an exemplary illustrative technique for formulating an miR-126 containing agent (e.g., an exosome and/or a microvesicle) with one of the aforementioned biofluids is provided by Witwer et al., Standardization of sample collection, isolation and analysis methods in extracellular vesicle research, J Extracell Vesicles. 2013; 2, the disclosure of which is incorporated herein by reference in its entirety.

In some non-limiting embodiments, the potency/quantity of an miR-126 containing agent formulation can be quantified using conventional tools and techniques known to those having ordinary skill in the art, e.g., the electrical resistance nano pulse method, using commercially available tools and components, to determine the yield of an exosome preparation (e.g., qNano; IZON Science Ltd., Oxford, UK) (see Komaki et al., Exosomes of human placenta-derived mesenchymal stem cells stimulate angiogenesis, Stem Cell Res Ther. 2017; 8:219, the disclosure of which is incorporated herein by reference in its entirety. Furthermore, the dosage of an miR-126 may also be confirmed/quantified using the tools available to one having ordinary skill such as tunable resistive pulse sensing, protein quantification (e.g., Protein Assay Rapid Kit, Wako Pure Chemicals, Osaka, Japan), nanoparticle tracking analysis, enzyme-linked immunosorbent assay (ELISA), flow cytometry, dynamic light scattering, cell equivalents, fingerprinting (i.e., quantifying surrogate markers as an indication), and/or using a sample to elicit a response on an in vitro/in vivo surrogate (see Willis et al., Toward Exosome-Based Therapeutics: Isolation, Heterogeneity, and Fit-for-Purpose Potency, Front Cardiovasc Med. 2017; 4:63, the disclosure of which is incorporated herein by reference in its entirety).

Prior to administration, some non-limiting embodiments—depending on the quantity and/or content of the miR-126 containing agent—will require appropriate storage and/or handling, the process and/or conditions of which should be dictated by the said quality/content of the miR-126 containing agent, and good medical practice. For example, in some non-limiting embodiments, an miR-126 containing agent formulation consisting of exosomes, or CD133+/KDR+ HUCBC derived exosomes; or pharmaceutically acceptable compositions containing HUCBC derived exosomes described herein, with any one of the abovementioned carriers, excipients, and diluents, may be stored at −20° C., for a length of time that will not degrade the miR-126 containing agent. Storage formulations that have been successful include buffers that resist pH shifts during freezing/thawing, and are devoid of glycerol and/or dimethyl sulfoxide (see Willis et al., Toward Exosome-Based Therapeutics: Isolation, Heterogeneity, and Fit-for-Purpose Potency, Front Cardiovasc Med. 2017; 4:63, the disclosure of which is incorporated herein by reference in its entirety). Furthermore, in some non-limiting embodiments, the container should be tailored to the miR-126 containing agent, for example, an exosome or a microvesicle, and should consist of a material that supports miR-126 containing agent storage (e.g., cell culture/clinical grade glassware or plastic) (see Lener et al., Applying extracellular vesicles based therapeutics in clinical trials, J Extracell Vesicles. 2015; 4:10.3402/jev.v4.30087, the disclosure of which is incorporated herein by reference in its entirety).

When necessary, proper fluidity can be maintained, for example, by the use of a coating such as lecithin, by the maintenance of the required size in the case of dispersion and by the use of surfactants. Nonaqueous vehicles such a cottonseed oil, sesame oil, olive oil, soybean oil, corn oil, sunflower oil, or peanut oil and esters, such as isopropyl myristate, may also be used as solvent systems for such compositions of an miR-126 containing agent. Furthermore, various additives which enhance the stability, sterility, and/or isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to some embodiments of the present invention, however, any vehicle, diluent, or additive used would have to be compatible with the miR-126 containing agents.

Sterile injectable solutions can be prepared by incorporating an miR-126 containing agent utilized in practicing some embodiments of the present invention in the required amount of the appropriate solvent with various of the other ingredients, as desired.

In some non-limiting embodiments, a formulation can be prepared by combining exosomes and/or microvesicles containing miR-126 isolated from hematopoietic stem cells, endothelial progenitor cells or CD133+/KDR+ human umbilical cord blood cells (HUCBCs). In some illustrative embodiments, a formulation may comprise one or more of HUCBC derived exosomes and/or microvesicles; CD133+/KDR+ HUCBC derived exosomes and/or microvesicles; and a pharmaceutically acceptable carrier, excipient, or diluent. In some embodiments, a formulation containing a miR-126 containing agent can include a composition comprising CD133+/KDR+ HUCBC derived exosomes and/or microvesicles described herein, in addition to any one or more of the abovementioned carriers, excipients, and diluents.

Administration

In various embodiments, methods are provided for the prevention and/or treatment of a cardiovascular disease or disorder in a subject who has suffered a cerebrovascular injury, for example a stroke, comprising administering to the subject in need thereof, a therapeutically effective amount of a miR-126 containing agent or an agent which induces expression of miR-126. The methods contemplate administering a composition that is pharmaceutically acceptable for the treatment of humans. In various embodiments, the administration of the miR-126 containing agent or agent which induces expression of miR-126 can be accomplished using an administration method known to those of ordinary skill in the art.

Dosages for a particular patient can be determined by one of ordinary skill in the art using conventional considerations, (e.g., by means of an appropriate, conventional pharmacological protocol). A physician may, for example, prescribe a relatively low dose or amount at first, subsequently increasing the dose or amount until an appropriate response is obtained. The dose or amount administered to a patient is sufficient to effect a beneficial therapeutic response in the patient over time, or, e.g., to reduce symptoms, or other appropriate activity, depending on the application. The dose or amount is determined by the efficacy of the particular formulation, and the activity, stability or serum half-life of the miR-126 containing agent employed and the condition of the patient, as well as the body weight or surface area of the patient to be treated. The size of the dose or amount is also determined by the existence, nature, and extent of any adverse side-effects that accompany the administration of a particular vector, formulation, or the like in a particular patient.

Therapeutic compositions comprising one or more miR-126 containing agents are optionally tested in one or more appropriate in vitro and/or in vivo animal models of disease, to confirm efficacy, tissue metabolism, and to estimate dosages, according to methods well known in the art. In particular, dosages can be initially determined by activity, stability or other suitable measures of treatment vs. non-treatment (e.g., comparison of treated vs. untreated cells or animal models), in a relevant assay. Formulations are administered at a rate determined by the $EC_{50}$ of the relevant formulation, and/or observation of any side-effects of the miR-126 containing agent at various concentrations, e.g., as applied to the mass and overall health of the patient. Administration can be accomplished via single or divided doses or amounts. Various factors may be used by a skilled practitioner, for example, a clinician, physician, or medical specialist to properly administer the miR-126 containing agent. For example, if using a miR-126 containing agent that can circulate freely in the bloodstream, the composition or formulation may be administered intravenously. The one or more an miR-126 containing agents can be administered in various ways; for example, each miR-126 containing agent can be administered alone or as an active ingredient in combination with pharmaceutically acceptable carriers, diluents, adjuvants and vehicles. The miRNA-126 agents can be administered orally, subcutaneously, or parenterally, including intravenous, intraarterial, intramuscular, intraperitoneal, and intranasal administration as well as intrathecal and infusion techniques, or by local administration or direct administration (stereotactic administration) to the site of disease or pathological condition. Implants containing one or more miR-126 containing agents may also be useful, where short term or long term (for example, hours, days or weeklong administration is desirable).

The subject or patient being treated is a warm-blooded animal and, in particular, mammals, including humans. The pharmaceutically acceptable carriers, diluents, adjuvants and vehicles as well as implant carriers generally refer to inert, non-toxic solid or liquid fillers, diluents or encapsulating material not reacting with the active components of the invention. In some embodiments, a miR-126 containing agent may be altered by use of antibodies to cell surface proteins to specifically target tissues of interest.

In some embodiments, when administering a miR-126 containing agent parenterally, it will generally be formulated in a unit dosage injectable form (for example, in the form of a liquid, for example, a solution, a suspension, or an emulsion). Some pharmaceutical formulations suitable for injection include sterile aqueous solutions or dispersions and sterile powders for reconstitution into sterile injectable solutions or dispersions. The carrier can be a solvent or dispersing medium containing, for example, water, ethanol, polyol (for example, glycerol, propylene glycol, liquid polyethylene glycol, and the like), suitable mixtures thereof, and vegetable oils.

A pharmacological formulation of some embodiments may be administered to the patient in an injectable formulation containing any compatible carrier, such as various vehicle, adjuvants, additives, and diluents; or the inhibitor(s) utilized in some embodiments may be administered parenterally to the patient in the form of slow-release subcutaneous implants or vectored delivery, iontophoretic, polymer matrices, liposomes, and microspheres. The formulation may be as, for example, microspheres, hydrogels, polymeric reservoirs, cholesterol matrices, or polymeric systems. In some embodiments, the system may allow sustained or controlled release of the composition to occur, for example, through control of the diffusion or erosion/degradation rate of the formulation containing the miRNA. In addition, a pump-based hardware delivery system may be used to deliver one or more embodiments.

Examples of systems in which release occurs in bursts includes, e.g., systems in which the miR-126 containing agent is entrapped in liposomes which are encapsulated in a polymer matrix, the liposomes being sensitive to specific stimuli, e.g., temperature, pH, light or a degrading Many other such implants, delivery systems, and modules are well known to those skilled in the art.

In some embodiments, without limitation, a miR-126 containing agent may be administered initially by an infusion or intravenous injection to bring blood levels of miR-126 microRNA to a suitable level. The patient's levels are then maintained by an intravenous dosage form, although other forms of administration, dependent upon the patient's condition and as indicated above, can be used. The quantity to be administered and timing of administration may vary for the patient being treated.

Additionally, in some embodiments, without limitation, a miR-126 containing agent may be administered in situ to bring internal levels to a suitable level. The patient's levels are then maintained as appropriate in accordance with good medical practice by appropriate forms of administration, dependent upon the patient's condition. The quantity to be administered and timing of administration may vary for the patient being treated.

In certain non-limiting embodiments, an miR-126 containing agent (e.g., an exosome or a microvesicle), is administered via intravenous injection, for example, a subject is injected intravenously with a formulation of miR-126 containing agent suspended in a suitable carrier using a needle with a gauge ranging from about 7-gauge to 25-gauge (see Banga (2015) Therapeutic Peptides and Proteins: Formulation, Processing, and Delivery Systems; CRC Press, Boca Raton, Fla.). An illustrative example of intravenously injecting an miR-126 containing agent includes, but is not limited to, uncovering the injection site; determining a suitable vein for injection; applying a tourniquet and waiting for the vein to swell; disinfecting the skin; pulling the skin taut in the longitudinal direction to stabilize the vein; inserting needle at an angle of about 35 degrees; puncturing the skin, and advancing the needle into the vein at a depth suitable for the subject and/or location of the vein; holding the injection means (e.g., syringe) steady; aspirating slightly; loosening the tourniquet; slowly injecting the miR-126 containing agent; checking for pain, swelling, and/or hematoma; withdrawing the injection means; and applying sterile cotton wool onto the opening, and securing the cotton wool with adhesive tape.

In some embodiments, the initial administration may include an infusion of the one or more miR-126 containing agents via intravenous administration over a period of 10 minutes to 120 minutes. Subsequent doses or amounts of the one or more mir-126 containing agents can be accomplished using intravenous injections. Each dose or amount administered may be therapeutically effective doses or amounts or suboptimal doses or amounts repeated if needed.

Any appropriate routes of exosome or microvesicle administration known to those of ordinary skill in the art may comprise embodiments of the invention. Isolated miR-126 containing agents contained within a pharmaceutically acceptable vehicle, carrier, or excipient, or miR-126 containing agents derived from mammalian cells, for example, stem cells, endothelial cells, mesenchymal stromal cells, umbilical cord cells, endothelial cells, cerebral endothelial cells, brain microvascular endothelial cells, Primary Human Brain Microvascular Endothelial Cells (ACBRI 376), endothelial progenitor cells, AC-133/CD-133+ cells and the like, Schwann cells, hematopoietic cells, reticulocytes, monocyte-derived dendritic cells (MDDCs), monocytes, macrophages, B lymphocytes, antigen-presenting cells, glial cells, astrocytes, neurons, oligodendrocytes, spindle neurons, microglia, mastocytes, hemangioblast cells, lymphoid progenitor cells, myeloid progenitor cells, vascular stem cells, endothelial progenitor cells, pericytes, hematopoietic stem cells, endothelial progenitor cells, human umbilical cord blood cells (HUCBCs), or CD133+/KDR+ cells, or their internal components thereof, can be administered and dosed in accordance with good medical practice, taking into account the clinical condition of the individual patient, the site and method of administration, scheduling of administration, patient age, sex, body weight and other factors known to medical practitioners.

In each of these embodiments, the administration is designed to supply the miR-126 containing agent to the tissue that requires miR-126 microRNA to prevent or treat the cardiovascular symptom or injury. In some embodiments, the target tissue includes one or more of: the blood vessels of the subject, the blood vessels of the heart and the heart, including the heart wall layers: the endocardium, myocardium and epicardium. The endocardium is the thin membrane that lines the interior of the heart. The myocardium is the middle layer of the heart. It is the heart muscle and is the thickest layer of the heart. The epicardium is a thin layer on the surface of the heart in which the coronary arteries lie. The pericardium is a thin sac the heart sits in, often filled with a small amount of fluid, which separates the heart from the other structures in the chest such as the lungs. In addition the heart tissue may include the tricuspid valve between the right atrium and the right ventricle; the pulmonary valve between the right ventricle and the pulmonary artery; the mitral valve between the left atrium and the left ventricle; and the aortic valve located between the left ventricle and the aorta.

Methods of Treatment

The inventors have unexpectedly found that when a subject experiences a cerebrovascular injury, for example, a stroke, there is a significant decrease in miR-126 microRNA expression in plasma and in the heart tissue, which leads to an increase in cardiovascular disease and/or disorder (e.g., cardiac dysfunction, cardiomyocyte hypertrophy, fibrosis, inflammation, and oxidative stress). Without wishing to be bound by any particular theory, it is believed that decreased miR-126 expression subsequent to stroke plays a role in cardiac disease or disorders, in both subjects with and without glucose metabolism disorders.

Accordingly, the present disclosure has identified several unexpected findings as illustrated in the examples section below. One such unexpected finding includes the discovery that stroke plays a major role in diminishing the levels of miR-126, and exacerbates cardiovascular disease or disorders in patients who have suffered a stroke, even those without any symptoms of cardiovascular disease and/or disorder prior to the stroke. As an example of one of the foregoing findings, a miR-126 containing agent can regulate cardiomyocyte hypertrophy (a hemodynamic compensation mechanism that occurs in response to the hemodynamic stress observed in subjects suffering from cardiovascular disease or disorders, as known to those with skill in the art). Further, a miR-126 containing agent can significantly improve cardiac function after a cerebrovascular injury, for example, stroke, in subjects with and without glucose metabolism disorders. Moreover, administering a miR-126 containing agent improves cardiac function, in terms of increased LVEF and SF, and decreased LVDD. In some embodiments, the subject to be treated is one in which their heart failure is systolic heart failure. In related embodiments, the systolic heart failure is characterized in that the subject has a LVEF of 40% or less.

The present disclosure addresses the diminishing levels of miR-126 after stroke by administering a therapeutically effective dose or amount of a miR-126 containing agent or agent that induces the expression of miR-126 to increase levels of miR-126 in the heart and/or circulation. The targets of miRNA are recognized via a complementary site on the target mRNA. The miRNA binds to an Argonaute protein, and forms a silencing complex that targets a complementary mRNA through Watson-Crick pairing between the mRNA target region, and the miRNA (see Lewis et al., Conserved seed pairing, often flanked by adenosines, indicates that thousands of human genes are microRNA targets, Cell. 2005 Jan. 14; 120(1):15-20). The expression of some miR-126 targets is increased following stroke (see Witkowski et al., Micro-RNA-126 reduces the blood thrombogenicity in diabetes mellitus via targeting of tissue factor. Arterioscler. Thromb. Vasc. Biol. 2016). Without wishing to be bound by any particular theory, it is believed that increasing levels of miR-126 in circulation and/or the heart enables the endothelial cells of blood vessels, and cardiomyocytes of the heart to decrease detrimental factors involved in stroke-induced cardiac dysfunction in subjects with or without a glucose metabolism disorder. Therefore, cardiovascular disease and disorders that have some association with stroke, glucose metabolism disorders, or in combination, may derive some benefit. These cardiovascular diseases and disorders can be one or more of: cardiomyocyte hypertrophy, myocardial fibrosis, cardiovascular-related cognitive decline, fibrosis, myocardial infarction, rheumatic heart disease, inflammatory heart disease, hypertensive heart disease, congenital heart disease, cardiac arrhythmias, aneurysm, angina, atherosclerosis, cardiomyopathy, carditis, congenital heart disease, coronary heart disease, coronary artery disease, heart failure, peripheral arterial disease, valvular heart disease, peripheral artery disease, thromboembolic disease, and venous thrombosis.

The present invention provides a method for treating and/or preventing cardiovascular disorders or disease in a subject who has suffered a cerebrovascular injury, for example, a stroke, and who may also suffer from a glucose metabolism disorder. Typically, there are two categories of stroke: ischemic and hemorrhagic (see F. H. Kobeissy, editor: Brain Neurotrauma: Molecular, Neuropsychological, and Rehabilitation Aspects (2015), Boca Raton, Fla., CRC Press/Taylor & Francis) Ischemic stroke occurs when the brain's blood supply is restricted due to obstruction of blood vessels or arterial stenosis. Ischemic stroke results in brain cells being deprived of oxygen and energy. There are two main categories of ischemic stroke: thrombotic and embolic stroke. During a thrombotic stroke, a blood clot forms at the occlusion site; alternatively, in embolic stroke, the clot forms at a distant artery and subsequently travels to the occlusion site. A hemorrhagic stroke occurs when weakened blood vessels rupture in the brain. Blood compresses the brain, resulting in symptoms. Hemorrhagic strokes are typically intracerebral or subarachnoid, and most frequently occur as a result of aneurysms, or arteriovenous malformations (AVMs).

Thus, methods of the present disclosure shall be taken to apply mutatis mutandis to methods for preventing a cardiovascular disorder in a subject who has suffered a neurological ischemic event, for example, a stroke. Furthermore, the terms "to treat" or "treatment" according to this invention include the treatment of symptoms of cardiovascular disorder or disease, the prevention or the prophylaxis of the symptoms of cardiovascular disorder or disease, the prevention or prophylaxis causing the symptoms of cardiovascular disorder or disease, as well as the prevention or the prophylaxis of the consequences causing the symptoms.

Symptoms of stroke include general symptoms such as sudden weakness, paralysis, numbness, confusion, trouble speaking or understanding speech, trouble seeing in one or both eyes, problems breathing, dizziness, trouble walking, loss of balance or coordination, and unexplained falls, loss of consciousness, and/or sudden and severe headache. More specifically, stroke symptoms include the following: carotid distribution; hemiparesis or monoparesis; hemisensory numbness or neglect; facial weakness; aphasia; dysarthria; vertigo; amaurosis fugax (fleeting blindness of one eye); vertebrobasilar distribution; dysarthria; dysphagia; diplopia; homonymous hemianopsia; total blindness (cortical blindness); alternating or bilateral weakness; alternating or bilateral numbness; "crossed" weakness or numbness (ipsilateral face and contralateral body); gait ataxia; and limb dysmetria.

In some embodiments, without limitation a subject who has suffered an ischemic stroke is treated with one or more miR-126 containing agents to prevent or treat a cardiovascular disease and/or disorder. In various embodiments, the one or more miR-126 containing agents is administered in therapeutically effective amounts to prevent and/or treat a cardiovascular disease and/or disorder, wherein the cardiovascular disease and/or disorder is selected from: cardiomyocyte hypertrophy, myocardial fibrosis, cardiovascular-related cognitive decline, fibrosis, myocardial infarction, rheumatic heart disease, inflammatory heart disease, hypertensive heart disease, congenital heart disease, cardiac arrhythmias, aneurysm, angina, atherosclerosis, cardiomyopathy, carditis, congenital heart disease, coronary heart disease, coronary artery disease, heart failure, peripheral arterial disease, valvular heart disease, peripheral artery disease, thromboembolic disease, and venous thrombosis.

In some embodiments, without limitation, the methods described herein can be utilized to treat and/or prevent cardiovascular disease or disorders in a subject who has suffered a cerebrovascular injury, for example, a stroke, and who may also have a glucose metabolism disorder. A "glucose metabolism disorder" is condition falling under a subset metabolic diseases characterized by a pathological condition in which blood glucose fails to be maintained in a normal range. Glucose metabolism disorders include: Diabetes Mellitus; Experimental Diabetes Mellitus; Type 1 Diabetes Mellitus; Wolfram Syndrome; Type 2 Diabetes Mellitus; Lipoatrophic Diabetes Mellitus; Gestational Diabetes; Diabetic Ketoacidosis; Donohue Syndrome; Latent Autoimmune Diabetes in Adults; Prediabetic State; Glycosuria; Renal Glycosuria; Hyperglycemia; Glucose Intolerance; Hyperinsulinism; Congenital Hyperinsulinism; Nesidioblastosis; Insulin Resistance; Metabolic Syndrome X; Hypoglycemia; and Insulin Coma. Glucose metabolism disorders, along with stroke, are implicated in cardiovascular disease, and can be prevented or treated using the compositions containing miR-126 microRNA described herein. Furthermore, subjects with a glucose metabolism disorder with one or more risk factors such as hypertension, abnormal cholesterol and/or high triglycerides, obesity, sedentary lifestyle, or tobacco use, are at an increased risk of cardiovascular disease and/or stroke (Bejot et al., Stroke in diabetic patients. Diabetes Metab. 2010 October; 36 Supp13:S84-7).

Type 2 diabetes is generally thought to be the most common glucose metabolism disorder. Typically, a subject with Type 2 diabetes does not produce and/or utilize insulin correctly (a process generally known as insulin resistance). Complications that can arise from Type 2 diabetes include, but are not limited to, hypertension, neuropathy, ketoacidosis, nephropathy, gastroparesis, and stroke. Subjects with Type 2 diabetes are at a 1.5 times higher risk for stroke, compared to normal healthy individuals (American Diabetes Association).

In some embodiments, without limitation, a subject with Type 2 Diabetes Mellitus who has suffered a stroke is treated with one or more miR-126 containing agents to prevent or treat a cardiovascular disease and/or disorder, for example, a cardiovascular disease or disorder selected from: cardiomyocyte hypertrophy, myocardial fibrosis, cardiovascular-related cognitive decline, fibrosis, myocardial infarction, rheumatic heart disease, inflammatory heart disease, hypertensive heart disease, congenital heart disease, cardiac arrhythmias, aneurysm, angina, atherosclerosis, cardiomyopathy, carditis, congenital heart disease, coronary heart disease, coronary artery disease, heart failure, peripheral arterial disease, valvular heart disease, peripheral artery disease, thromboembolic disease, and venous thrombosis.

The amount of miR-126 containing agents in the exemplified compositions, and formulations, whether pharmaceutically acceptable or not, may vary according to factors such as the type of disease, state, age, sex, and weight of the individual. Dosage regimens may be adjusted to provide the optimum therapeutic response. For example, a single bolus of miR-126 containing agents (e.g., a single bolus of exosomes, or compositions containing the contents of said exosomes, or a single bolus of microvesicles, or compositions containing the contents of said microvesicles) may be administered, several divided doses or amounts may be administered over time, or the dose or amount may be proportionally reduced or increased as indicated by the exigencies of the therapeutic situation. It is especially advantageous to formulate parenteral compositions (for example by intravenous, intraperitoneal, intranasal, subcutaneous, or other known routes for delivery of cells or components thereof) in a dosage unit form for ease of administration and uniformity of dosage. Dosage unit form as used herein refers to physically discrete units suited as unitary dosages for the mammalian subjects to be treated; each unit containing a predetermined quantity of active compound (e.g., exosomes or microvesicles with or without a miR-126 containing agent) calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

The composition of the invention can be delivered to the subject at a dose or amount that is effective to treat and/or prevent cardiovascular disease or disorders, for example heart attack, cardiomyopathy, or heart failure. The effective dosage will depend on many factors including the gender, age, weight, and general physical condition of the subject, the severity of the symptoms, the particular compound or composition being administered, the duration of the treatment, the nature of any concurrent treatment, the carrier used, and like factors within the knowledge and expertise of those skilled in the art. As appropriate, a treatment effective amount in any individual case can be determined by one of ordinary skill in the art by reference to the pertinent texts and literature and/or by using routine experimentation (see, e.g., Remington, The Science and Practice of Pharmacy (21st ed. 2005)).

In one embodiment, an miR-126 containing agent comprising miR-126 microRNA is administered to a subject in need thereof (i.e., who has had a stroke), at a dose or amount of about 0.00001 µg/kg to about 10 mg/kg, or about 0.0001 µg/kg to about 1 mg/kg, or about 0.0001 µg/kg to about 900 µg/kg, or about 0.005 µg/kg to about 500 µg/kg, or about 0.01 µg/kg to about 100 µg/kg, or about 0.1 µg/kg to about 50 µg/kg; and, the present invention encompasses every sub-range within the cited ranges and amounts.

In another embodiment, one or more miR-126 containing agents (i.e. exosomes and/or microvesicles derived from mammalian cells) are administered at a dose or amount of about $1 \times 10^5$ to about $1 \times 10^{17}$ mammalian cell derived exosomes and/or microvesicles per kg of body weight of the subject, or $1 \times 10^5$ to about $1 \times 10^{16}$ mammalian cell derived exosomes and/or microvesicles per kg of body weight of the subject, or $1 \times 10^6$ to about $1 \times 10^{15}$ mammalian cell derived exosomes and/or microvesicles per kg of body weight of the subject, or $1 \times 10^7$ to about $1 \times 10^{14}$ mammalian cell derived exosomes and/or microvesicles per kg of body weight of the subject, or $1 \times 10^8$ to about $1 \times 10^{13}$ mammalian cell derived exosomes and/or microvesicles per kg of body weight of the subject, or $1 \times 10^9$ to about $1 \times 10^{12}$ mammalian cell derived exosomes and/or microvesicles per kg of body weight of the subject, or $1 \times 10^1$ to about $1 \times 10^{17}$ mammalian cell derived exosomes and/or microvesicles per kg of body weight of the subject, or $1 \times 10^1$ to about $1 \times 10^{16}$ mammalian cell derived exosomes and/or microvesicles per kg of body weight of the subject, or $1 \times 10^1$ to about $1 \times 10^{15}$ mammalian cell derived exosomes and/or microvesicles per kg of body weight of the subject, or $1 \times 10^1$ to about $1 \times 10^{14}$ mammalian cell derived exosomes and/or microvesicles per kg of body weight of the subject, or $1 \times 10^1$ to about $1 \times 10^{13}$ mammalian cell derived exosomes and/or microvesicles per kg of body weight of the subject, or $1 \times 10^1$ to about $1 \times 10^{12}$ mammalian cell derived exosomes and/or microvesicle per kg of body weight of the subject.

In some embodiments, the miR-126 containing agent comprises mammalian derived exosomes and/or microvesicles, administered at a dose or amount of about $1 \times 10^{10}$ to about $1 \times 10^{19}$, or about $1 \times 10^{11}$ to about $1 \times 10^{18}$, or about $1 \times 10^{12}$ to about $1 \times 10^{17}$, or about $1 \times 10^{13}$ to about $1 \times 10^{16}$, mammalian cell derived exosomes and/or microvesicles per dose or amount, once or multiple times per day, or once or multiple times per week, or once or multiple times per month. In various embodiments, the exemplified doses or amounts of mammalian cell derived exosomes and/or microvesicles per kg weight of the patient are daily doses or amounts or therapeutically effective doses or amounts, either in unit form or in sub-unit forms to be dosed one or more times per day, or one or more times per week, or one or more times per month.

In each of the above referenced mammalian cell derived exosome and/or microvesicle dosages, the mammalian cells that can be used to isolate the exosomes and/or microvesicles can include: cells that are known to produce exosomes, and microvesicles, for example, stem cells, endothelial cells, mesenchymal stromal cells, umbilical cord cells, cerebral endothelial cells, brain microvascular endothelial cells, Primary Human Brain Microvascular Endothelial Cells (ACBRI 376), endothelial progenitor cells, AC-133/CD-133+ cells and the like, Schwann cells, hematopoietic cells, reticulocytes, monocyte-derived dendritic cells (MDDCs), monocytes, macrophages, B lymphocytes, antigen-presenting cells, glial cells, astrocytes, neurons, oligodendrocytes, spindle neurons, microglia, mastocytes, hemangioblast cells, lymphoid progenitor cells, myeloid progenitor cells, vascular stem cells, endothelial progenitor cells, pericytes, hematopoietic stem cells, endothelial progenitor cells, human umbilical cord blood cells (HUCBCs), or CD133+/KDR+ cells.

In one embodiment of the invention, the subject is one that has suffered a stroke, and has developed a cardiovascular disease or disorder, and the composition of the invention is administered to the subject after the development of the cardiovascular disease or disorder in order to ameliorate and/or relieve the symptoms, or the severity of the symptoms of the cardiovascular disease or disorder. In another embodiment, the subject is one that has suffered a stroke, and has not developed a cardiovascular disease or disorder, and the composition of the invention is administered to the subject to prevent the development of cardiovascular disease or disorders or symptoms thereof. In one embodiment, the subject has glucose metabolism disorder and has suffered a stroke, and has subsequently developed a cardiovascular disease or disorder, and the composition of the invention is administered to the subject after the development of the cardiovascular disease or disorder in order to ameliorate and/or relieve the symptoms. In one embodiment, the subject has glucose metabolism disorder and has suffered a stroke, and has not developed a cardiovascular disease or disorder, and the composition of the invention is administered to the subject to prevent cardiovascular disease or disorder. Accordingly, the composition of the invention can be delivered to the subject prior to the event occurring (i.e., a cerebrovascular injury, e.g., a stroke); concurrently with the event; and/or after the event occurs but before the development of cardiovascular disease or disorder symptoms, or after the event occurs and after the development of cardiovascular disease or disorder symptoms.

Heart failure generally describes a number of progressive and chronic conditions characterized by a decrease in the hearts ability to pump blood. Symptoms of heart failure include, but are not limited to shortness of breath; fatigue; lightheadedness; exercise intolerance; coughing (or chronic cough); wheezing; tachycardia; fatigue; loss of appetite; nausea; confusion; and other symptoms. Further, manifestations of heart failure include, but are not limited to aortic regurgitation; hypertrophic cardiomyopathy; aortic stenosis; left ventricular failure; tricuspid stenosis; pulmonary arterial hypertension; tricuspid regurgitation; constrictive pericarditis; mitral regurgitation; aortic regurgitation; systemic arterial hypertension; pulmonary arterial hypertension; mitral regurgitation; abnormal mitral valve prolapse (systolic click); abnormal bicuspid aortic valve (ejection sound); abnormal pulmonic stenosis (ejection sound); tricuspid regurgitation; abnormal patent ductus arteriosis murmur; pericardial friction rub; abnormal peripheral arterial pulses; and other symptoms.

Systolic heart failure, specifically left ventricular systolic dysfunction occurs when the left ventricle fails to contract at normal, optimal levels, and is characterized by decreased LVEF (see Chronic Heart Failure: National Clinical Guideline for Diagnosis and Management in Primary and Secondary Care, (2010) NICE Clinical Guidelines, No. 108). Alternatively, diastolic heart failure occurs when the left ventricle cannot relax and/or flood as normal. Symptoms of systolic heart failure include heart attack; hypertension; murmur and/or arrhythmia; and/or cardiomyopathy. Systolic heart failure can be diagnosed using well known techniques in the art including without limitation, electrocardiograph; LVEF; chest x-ray; echocardiograph; and blood tests distinguishing natriuretic peptides.

In some non-limiting embodiments, the subject is one that has suffered a stroke, and has developed heart failure (acute or chronic heart failure), and the composition of the invention is administered to the subject after the development of heart failure in order to ameliorate and/or relieve the symptoms. In another embodiment, the subject is one that has suffered a stroke, and has not developed heart failure, and the composition of the invention is administered to the subject to prevent the development of heart failure. In one embodiment, the subject has glucose metabolism disorder and has suffered a stroke, and has subsequently developed heart failure, and the composition of the invention is administered to the subject after the development of heart failure in order to ameliorate and/or relieve the symptoms. In one embodiment, the subject has glucose metabolism disorder and has suffered a stroke, and has not developed heart failure, and the composition of the invention is administered to the subject to prevent heart failure. Accordingly, the composition of the invention can be delivered to the subject prior to the event occurring; concurrently with the event; and/or after the event occurs but before the development of heart failure symptoms.

In some non-limiting embodiments, the subject is one that has suffered a stroke, and has developed systolic heart failure, and the composition of the invention is administered to the subject after the development of systolic heart failure in order to ameliorate and/or relieve the symptoms of systolic heart failure. In another embodiment, the subject is one that has suffered a stroke, and has not developed a systolic heart failure, and the composition of the invention is administered to the subject to prevent the development of systolic heart failure. In one embodiment, the subject has glucose metabolism disorder and has suffered a stroke, and has subsequently developed a systolic heart failure, and the composition of the invention is administered to the subject after the development of systolic heart failure in order to ameliorate and/or relieve the symptoms. In one embodiment, the subject has glucose metabolism disorder and has suffered a stroke, and has not developed systolic heart failure, and the composition of the invention is administered to the subject to prevent systolic heart failure. Accordingly, the composition of the invention can be delivered to the subject prior to the event occurring; concurrently with the event; and/or after the event occurs but before the development of systolic heart failure symptoms. Events that are likely to result in the development of systolic heart failure are well known and include, without limitation, high blood pressure; high cholesterol; diabetes; unhealthy diet; sedentary lifestyle; obesity; moderate to high levels of alcohol consumption; tobacco use; increase age; race (i.e., non-Hispanic whites, non-Hispanic blacks, and American Indians, Hispanics, and Asian Americans) (see Fryar et al. Prevalence of Uncontrolled Risk Factors for Cardiovascular Disease: U.S., 1999-2010. NCHS Data Brief, No. 103. Hyattsville, Md.: National Center for Health Statistics, Centers for Disease Control and Prevention, U.S. Dept of Health and Human Services).

Cardiomyopathy is a condition wherein the myocardium suffers structural and functional abnormalities (Sisakian, Cardiomyopathies: Evolution of pathogenesis concepts and potential for new therapies, World J Cardiol. 2014 Jun. 26; 6(6): 478-494). Cardiomyopathy has traditionally been classified as primary or secondary cardiomyopathy. Typically, primary cardiomyopathy results from genetic, non-genetic, and/or acquired causes. Causes of primary cardiomyopathy include congenital conduction defects; mitochondrial disorders; and ion channel mutations. Conditions categorized as primary cardiomyopathy include, but are not limited to hypertrophic cardiomyopathy, and restrictive cardiomyopathy. Secondary cardiomyopathies are conditions wherein systemic and/or multi-organ disease results in myocardial damage, and can be caused by drugs; heavy metals; sarcoidosis; diabetes; hyperthyroidism; hypothyroidism; hyperparathyroidism; Friedreich's ataxia; Duchenne-Becker muscular dystrophy; myotonic dystrophy; Beriberi; scurvy; dermatomyositis; scleroderma; and/or as a consequence of cancer therapy (e.g., radiation) (Sisakian, Cardiomyopathies: Evolution of pathogenesis concepts and potential for new therapies, World J Cardiol. 2014 Jun. 26; 6(6): 478-494). Symptoms of cardiomyopathy include, but are not limited to jerky pulse; prominent "a" wave; double apex beat; late ejection quality systolic murmur over the aortic area that is increased by standing and decreased by squatting; pansystolic murmer at apex; breathlessness with exertion or even at rest; swelling of extremities; bloating; cough upon lying; fatigue; arrhythmia; chest pain; and dizziness. Additionally, histologic findings for cardiomyopathy are typically nonspecific, and include fibrosis, necrosis, and myocyte hypertrophy (Ashley et al., Cardiology Explained, London: Remedica; 2004).

In some non-limiting embodiments, the subject is one that has suffered a stroke, and has developed cardiomyopathy, and the composition of the invention is administered to the subject after the development of cardiomyopathy in order to ameliorate and/or relieve the symptoms. In another embodiment, the subject is one that has suffered a stroke, and has not developed a cardiomyopathy, and the composition of the invention is administered to the subject to prevent the development of cardiomyopathy. In one embodiment, the subject has glucose metabolism disorder and has suffered a stroke, and has subsequently developed a cardiomyopathy, and the composition of the invention is administered to the subject after the development of cardiomyopathy in order to ameliorate and/or relieve the symptoms. In one embodiment, the subject has glucose metabolism disorder and has suffered a stroke, and has not developed cardiomyopathy, and the composition of the invention is administered to the subject to prevent cardiomyopathy. Accordingly, the composition of the invention can be delivered to the subject prior to the event occurring; concurrently with the event; and/or after the event occurs but before the development of cardiomyopathy symptoms. Events that are likely to result in the development of cardiomyopathy are well known and include, without limitation, hypertension; family history of cardiomyopathy, heart failure, or sudden cardiac arrest; coronary heart disease; heart attach; viruses that lead to cardiac inflammation; diabetes; severe obesity; hemochromatosis; sarcoidosis; amyloidosis; alcoholism; and/or drug use (NIH: National Heart, Lung, and Blood Institute, Health Information for the Public, 2017).

In a non-limiting exemplary illustration of the invention, an embodiment as disclosed herein provides methods of treatment of any of the various cardiovascular disease or disorders enumerated above comprising administering an miR-126 containing agent, for example, mammalian cell derived exosomes and/or microvesicles containing miR-126. In one such illustrative non-limiting embodiment, the methods of the present invention comprise administering a miR-126 containing agent, for example, exosomes and/or microvesicles containing miR-126 isolated from stem cells, endothelial cells, stem cells, mesenchymal stromal cells, umbilical cord cells, endothelial cells, cerebral endothelial cells, brain microvascular endothelial cells, Primary Human Brain Microvascular Endothelial Cells (ACBRI 376), endothelial progenitor cells, AC-133/CD-133+ cells and the like, Schwann cells, hematopoietic cells, reticulocytes, monocyte-derived dendritic cells (MDDCs), monocytes, macrophages, B lymphocytes, antigen-presenting cells, glial cells, astrocytes, neurons, oligodendrocytes, spindle neurons, microglia, mastocytes, or in vitro cell cultures of any of the foregoing, in therapeutically effective amounts to a subject that has suffered a stroke, and has developed heart failure and/or cardiomyopathy, and the miR-126 containing agent is administered to the subject after the development of heart failure and/or cardiomyopathy in order to ameliorate and/or relieve the symptoms. In another embodiment, the subject is one that has suffered a stroke, and has not developed heart failure and/or cardiomyopathy, and the miR-126 containing agent is administered to the subject to prevent the development of heart failure and/or cardiomyopathy. In another embodiment, the subject has glucose metabolism disorder and has suffered a stroke, and has subsequently developed heart failure and/or cardiomyopathy, and the miR-126 containing agent is administered to the subject after the development of heart failure and/or cardiomyopathy in order to ameliorate and/or relieve the symptoms and/or manifestations of heart failure and/or cardiomyopathy. In one embodiment, the subject has glucose metabolism disorder and has suffered a stroke, and has not developed heart failure and/or cardiomyopathy, and the miR-126 containing agent is administered to the subject to prevent heart failure and/or cardiomyopathy. Accordingly, in the aforementioned non-limiting embodiments, the miR-126 containing agent can be delivered to the subject prior to the event occurring; concurrently with the event; and/or after the event occurs but before the development of systolic heart failure and/or cardiomyopathy symptoms/manifestations.

In some embodiments, the methods of the present invention comprise administering a miR-126 containing agent, for example, exosomes and/or microvesicles derived from endothelial cells, cerebral endothelial cells, brain microvascular endothelial cells, Primary Human Brain Microvascular Endothelial Cells (ACBRI 376), endothelial progenitor cells, or AC-133/CD-133+ cells, in therapeutically effective amounts to a subject that has suffered a stroke, and has developed heart failure and/or cardiomyopathy, and the miR-126 containing agent is administered to the subject after the development of heart failure and/or cardiomyopathy in order to ameliorate and/or relieve the symptoms. In another embodiment, the subject is one that has suffered a stroke, and has not developed heart failure and/or cardiomyopathy, and the miR-126 containing agent is administered to the subject to prevent the development of heart failure and/or cardiomyopathy. In another embodiment, the subject has glucose metabolism disorder and has suffered a stroke, and has subsequently developed heart failure and/or cardiomyopathy, and the miR-126 containing agent is administered to the subject after the development of heart failure and/or cardiomyopathy in order to ameliorate and/or relieve the symptoms and/or manifestations of heart failure and/or cardiomyopathy. In one embodiment, the subject has glucose metabolism disorder and has suffered a stroke, and has not developed heart failure and/or cardiomyopathy, and the miR-126 containing agent is administered to the subject to prevent heart failure and/or cardiomyopathy. Accordingly, in the aforementioned non-limiting embodiments, the miR-126 containing agent can be delivered to the subject prior to the event occurring; concurrently with the event; and/or after the event occurs but before the development of systolic heart failure and/or cardiomyopathy symptoms/manifestations.

In some embodiments, CD133+/KDR+ HUCBC derived exosomes and/or microvesicles are administered in therapeutically effective amounts to a subject that has suffered a stroke, and has developed heart failure and/or cardiomyopathy, and the miR-126 containing agent is administered to the subject after the development of heart failure and/or cardiomyopathy in order to ameliorate and/or relieve the symptoms. In another embodiment, the subject is one that has suffered a stroke, and has not developed heart failure and/or cardiomyopathy, and the miR-126 containing agent is administered to the subject to prevent the development of heart failure and/or cardiomyopathy. In another embodiment, the subject has glucose metabolism disorder and has suffered a stroke, and has subsequently developed heart failure and/or cardiomyopathy, and the miR-126 containing agent is administered to the subject after the development of heart failure and/or cardiomyopathy in order to ameliorate and/or relieve the symptoms and/or manifestations of heart failure and/or cardiomyopathy. In one embodiment, the subject has glucose metabolism disorder and has suffered a stroke, and has not developed heart failure and/or cardiomyopathy, and the miR-126 containing agent is administered to the subject to prevent heart failure and/or cardiomyopathy. Accordingly, in the aforementioned non-limiting embodiments, the miR-126 containing agent can be delivered to the subject prior to the event occurring; concurrently with the event; and/or after the event occurs but before the development of systolic heart failure and/or cardiomyopathy symptoms/manifestations. In all of these examples referred to above, heart failure includes all forms of heart failure, including acute, chronic, systolic or diastolic and combinations thereof.

While some embodiments have been particularly shown and described with reference to the foregoing preferred and alternative embodiments, it should be understood by those skilled in the art that various alternatives to the embodiments described herein may be employed in practicing the invention without departing from the spirit and scope of the invention as defined in the following claims. It is intended that the following claims define the scope of the invention and that the methods, systems, and compositions within the scope of these claims and their equivalents be covered thereby. This description of some embodiments should be understood to include all novel and non-obvious combinations of elements described herein, and claims may be presented in this or a later application to any novel and non-obvious combination of these elements. The foregoing embodiments are illustrative, and no single feature or element is essential to all possible combinations that may be claimed in this or a later application. Where the claims recite "a" or "a first" element of the equivalent thereof, such claims should be understood to include incorporation of one or more such elements, neither requiring nor excluding two or more such elements.

EXAMPLES

The following examples of some embodiments are provided without limiting the invention to only those embodiments described herein and without disclaiming any embodiments.

Example 1

Example 1 shows the effect of miR-126 miRNA on cardiovascular function subsequent to stroke. The extraluminal permanent distal middle cerebral artery occlusion (dMCAo) technique was implemented on Model Adult (3-4 months) male wild-type (WT) C57/BJ6L mice from Jackson Laboratory. Mice were anesthetized with 3.5% isoflurane in a mixture of $N_2O:O_2$ (2:1) and maintained at 0.5%~1.5% isoflurane using a facemask, and were then subjected to sham control or right extraluminal permanent dMCAo. A midline incision was opened between the orbit and the ear. A small burr hole was produced in the skull. The main branch of the MCA was coagulated with a small heater probe, and the vessel was transected. The same procedures without artery coagulation were performed on sham control mice (n=10/group).

To generate specific conditional EC MiR-126 Knockout (MiR-126EC−/−) Mice, PDGFiCreER:miR-126flox/flox mice were crossbred with miR-126flox/flox mice. Genotyping was performed at 4 weeks after birth. Then, both the PDGFiCreER:miR-126flox/flox and miR-126flox/flox mice were treated with tamoxifen (1 mg/10 g body weight of tamoxifen dissolved in corn oil); 4 doses were administered every other day i.p. tamoxifen treated PDGFiCreER:miR-126flox/flox mice have specific EC miR-126 deletion (called miR-126EC−/−). MiR-126fl/fl mice were employed as knockdown control. MiR-126EC−/− and miR-126fl/fl mice were subjected to dMCAo (n=10/group).

Cardiac function measurements was measured by echocardiography before stroke and at 4 weeks after stroke. Transthoracic Doppler echocardiography was performed on conscious mice using a Doppler echocardiograph (Acuson C516) equipped with a 15-MHz linear transducer (15L-8). Mice were trained for 3 days before echocardiography. Briefly, the mouse was picked up by the nape of the neck and held firmly in the palm of one hand in the supine position. In the inventor's experience, most mice develop bradycardia during the first training session; however, with repeated training the bradycardia disappears and mice remain calm. After training, the left hemithorax was shaved and a pre-warmed ultrasound transmission gel was applied to the chest. LVEF was measured using the formula: LVEF= [(LVAd−LVAs)/LVAs×100], where LVAd is LV diastolic area and LVAs is LV systolic area. All primary measurements were digitized by goal-directed, diagnostically driven software and 3 beats were averaged for each measurement.

Histological and immunohistochemical assessment was performed using mice sacrificed at 28 days after dMCAo. The brain and the heart were isolated and fixed in 4% paraformaldehyde prior to embedding in paraffin. Brain coronal tissue sections (bregma −1 mm to +1 mm) were cut (6 μm thick) and stained with hematoxylin and eosin for calculation of lesion volume. Heart coronal sections (6 μm thick) were cut, and PicroSirius Red (PSR) staining was employed to assess myocyte cross-sectional area (MCSA, identifies cardiomyocyte size) and interstitial collagen fraction (ICF) measurement. ICF is a measurement of cardiac interstitial and perivascular fibrosis, measured by a percent rate of PSR-stained collagen area to total myocardial area. Immunostaining was carried out using antibodies against mouse CD68 (ED1, a marker for monocytes/macrophages; 1:30, Bio-Rad); transforming growth factor (TGF-β; 1:500, Santa Cruz); monocyte chemo-tactic protein-1 (MCP-1; 1:100, Abcam); vascular cell adhesion molecule 1 (VCAM-1, 1:200, Santa Cruz); NADPH oxidase-2 (NOX2; 1:400, BD Bioscience). Negative controls were processed in a similar fashion but without the primary antibody.

Immunostaining quantification was performed using five slides from each heart, each slide containing 3 fields of view, and digitized under a ×20 objective (Olympus BX40) using a 3-CCD color video camera (Sony DXC-970MD) interfaced with an MCID image analysis system (Imaging Research). Image analysis was performed in a blinded fashion. Positive areas of PSR, TGF-13, NOX2, MCP-1 and positive cell number of ED1 in the fields of view were calculated.

Mouse Neonatal Cardiomyocyte Culture was performed using mouse neonatal hearts were enzymatically dissociated into a single cell suspension. Briefly, the hearts were finely cut and broken up into single cells in 0.1% collagenase/dispace (Roche). The cells were cultured in DMEM with 10% fetal bovine serum (FBS) and 1% antibiotic/antimycotic (Invitrogen). Further immunostaining was performed to determine whether the cultured cell were cardiomyocyte, or anti-sarcomeric alpha actinin (cardiomyocyte and skeletal muscle cell marker, EA-53, Abcam).

Primary EC culture and EC-Exosome isolation was performed to determine whether miR-126 derived from endothelial cells affects cardiomyocytes, exosomes derived from brain endothelial cells of miR-126fl/fl (miR-126fl/fl-EC-Exo) and miR-126EC−/− (miR-126EC−/−EC-Exo) mice were used to treat ischemic cardiomyocytes in culture. Briefly, brain ECs were isolated from adult male miR-126fl/fl and miR-126EC−/− mice. Primary brain ECs were cultured up to 3 passages and then cultured in exosome-depleted FBS media (Systembio) for 3 days. After exosomes were isolated, exosome-depleted FBS was used for all further cell cultures. EC-Exo was isolated using ExoQuick-TC, following standard protocol and suspended in PBS. EC-Exo concentration was quantified using the IZON qNano device (Izon, Christchurch, New Zealand). To decrease the heterogeneity of EC-Exo treatment, the inventor's tightly controlled the EC culture conditions, such as EC passage, density, and culture time. Protein concentration was determined for each EC-Exo dose employed.

Oxygen-glucose deprivation (OGD) was performed to induce cardiomyocyte ischemia in vitro. Cardiomyocyte culture media was replaced with glucose and serum-free media and placed in a hypoxia chamber (Forma Anaerobic System, Thermo Fisher Scientific) for 2 hours of OGD at 37° C. The experimental groups include (1) cardiomyocyte control; (2) cardiomyocytes +20 ng/ml miR-126fl/fl-EC-Exo; (3) cardiomyocytes +20 ng/ml miR-126EC−/−EC-Exo for 24 h.

Knockdown of miR-126 in cultured mouse cardiomyocytes was performed using mmu-miR-126-3p inhibitor (miR-126 knockdown), or scrambled negative control inhibitor (Thermo Scientific) using an electroporation transfection method. Briefly, mouse cardiomyocytes were harvested and resuspended in 95 ptl Ingenio electroporation solution (Mirus) and in 5 ptl of 20 ptM miR-126 inhibitor or scrambled control (Dharmacon). The cell suspension was placed in an Ingenio cuvette (Mirus) and electroporated in a Lonza Nucleofector using program Y-01. Then cells were cultured for 2 days and miR-126 expression was measured.

Cardiomyocyte structure changes and cell-size was determined using F-actin staining. Briefly, fixed cells were labeled with anti-F-actin (CytoPainter F-actin Staining Kit-Green Fluorescence, Abcam) and nuclei were labeled with DAPI. For cell surface area measurements, 6 areas were randomly selected from each 10-mm cover-slipped area.

Western blot assay was performed by isolating protein from samples using Trizol (Invitrogen). Protein concentration was measured using the BCA kit (Thermo Fisher Scientific). MCP-1 (1:1000, Abcam), NOX2 (1:1000, BD Bioscience), TGF-13 (1:1000, Santa Cruz), or VCAM-1 (1:500, Santa Cruz) primary antibodies were employed. Anti-13-actin (1:10,000; Abcam) antibody was loaded for control measurements.

Real-Time PCR was performed by isolating the total RNA with TRIzol (Invitrogen) to make cDNA using the M-MLV (Invitrogen) standard protocol. TaqMan real-time PCR was used and ran on a ViiA7 system (Applied Biosystems). Each sample was tested in triplicate, and analysis of relative gene expression data was performed using the 2-ΔΔCT method. The primers for real-time PCR listed in Table 1 were designed using Primer Express software (Applied Biosystems).

TABLE 1

| Gene Name | Sequence | Primer Type | SEQ ID NO |
|---|---|---|---|
| ED1 | GAAGGAAAGAGCTGAAGAGCAG | Forward | 7 |
|  | AGGTTTAGGAGAGGGTTTCCAC | Reverse | 8 |
| MCP-1 | CTGCTACTCATTCACCAGCAAG | Forward | 9 |
|  | CTCTCTCTTGAGCTTGGTGACA | Reverse | 10 |
| NOX2 | GAATTGTACGTGGACAGACTGC | Forward | 11 |
|  | CAAGTCATAGGAGGGTTTCCAG | Reverse | 12 |
| TGF-β | GCAACATGTGGAACTCTACCAG | Forward | 13 |
|  | GTATTCCGTCTCCTTGGTTCAG | Reverse | 14 |
| VCAM-1 | CAGGTGGAGGTCTACTCATTCC | Forward | 15 |
|  | CTCCAGATGGTCAAAGGGATAC | Reverse | 16 |

MiR-126 expression was measured by TaqMan miRNA assay (Life Technology). Briefly, samples (serum, heart, or cultured cells) were lysed in Qiazol reagents and the total RNA was isolated. PCR amplification was performed with the TaqMan miRNA assay kit according to the manufacturer's protocols, with U6 snRNA as an internal control.

Statistical data was expressed as mean±SE. Independent two-sample t-test was used to compare the differences between dMCAo and non-stroke groups. When multiple comparisons were performed, Hochberg's step-up procedure was used to adjust p-values. The pair-wise comparison was set at 0.05.

Figure 1B:
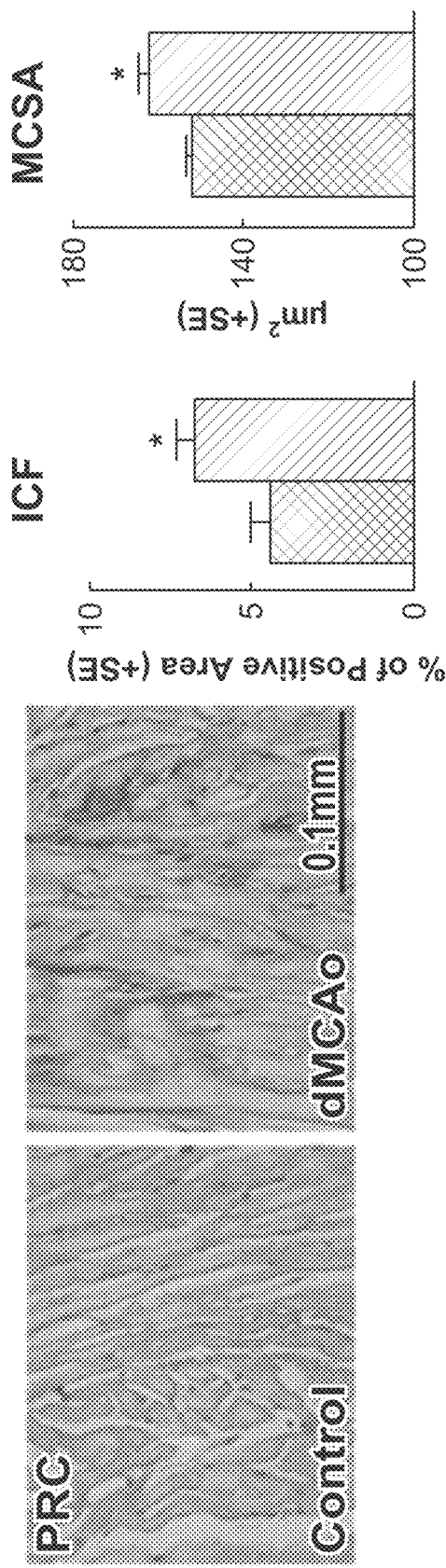
FIG. 1B depicts various experimental results of induced stroke in mice. Picro-Sirius Red staining for myocyte cross-sectional area and interstitial collagen fraction are shown on the left and a bar graph quantifying the values is shown on the right.
Figure 2A:
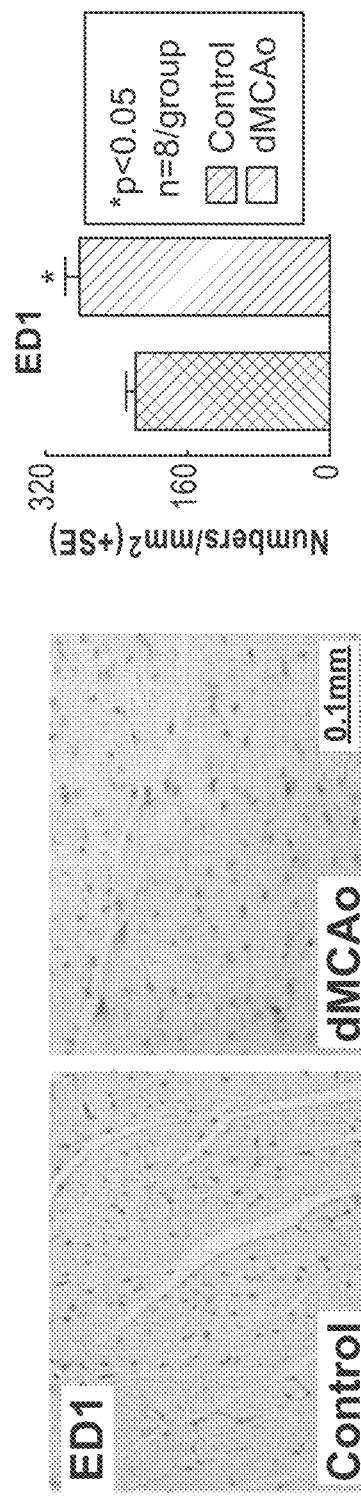
FIG. 2A, FIG. 2B, FIG. 2C and FIG. 2D depict various experimental results illustrating the cardiac inflammation and oxidative stress in stroke-mice compared to control mice.
Figure 2B:
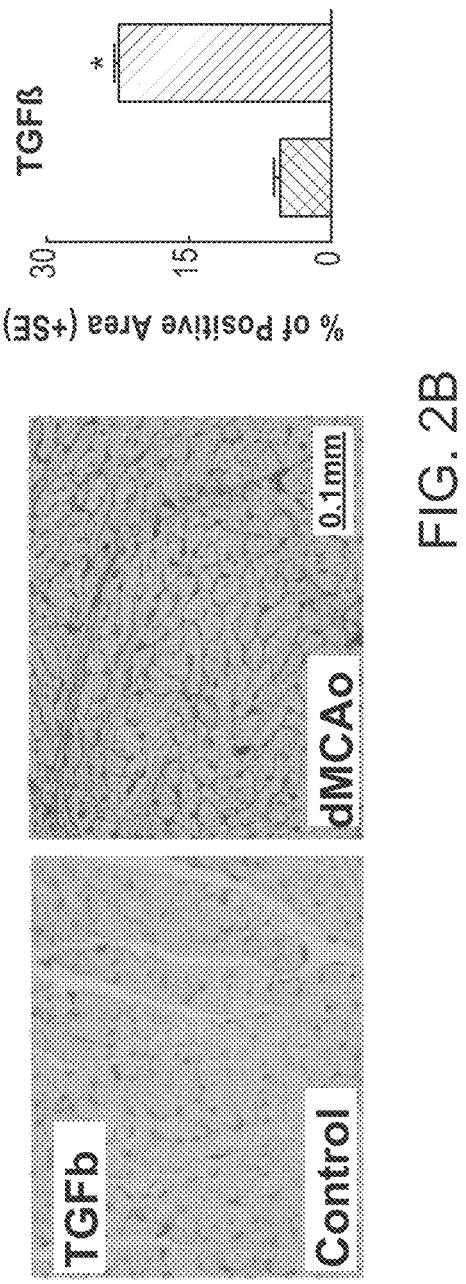
Figure 2C:
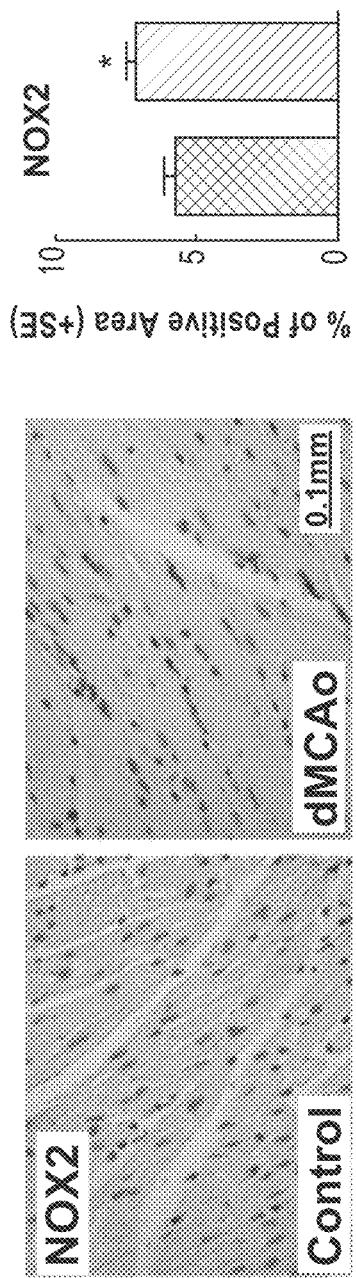
Figure 2D:
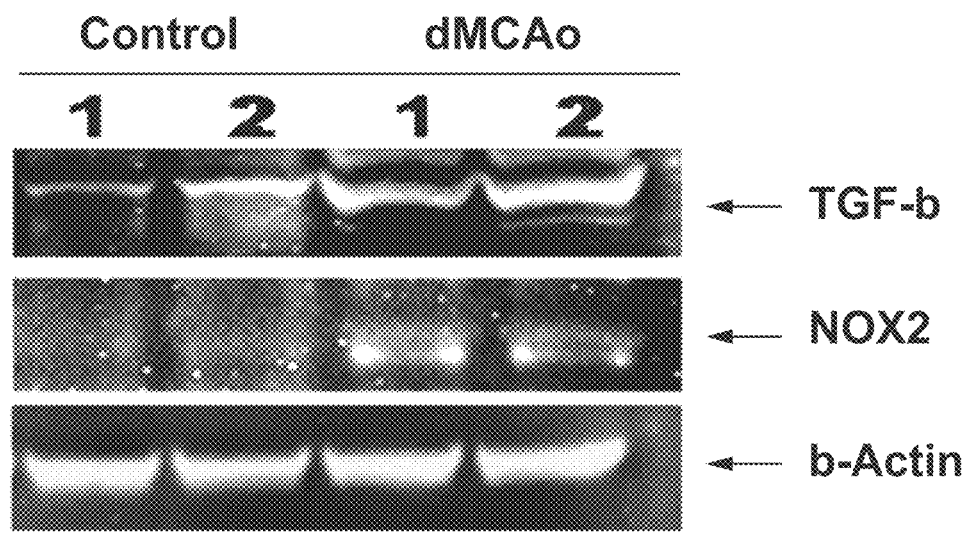

Using the aforementioned techniques, the inventors have demonstrated that cerebral ischemic stroke induces cardiac dysfunction, cardiomyocyte hypertrophy, fibrosis, inflammation, and oxidative stress compared to non-stroke mice. To test whether stroke induces cardiac dysfunction, echocardiography was employed in conscious mice at 28 days after stroke. The ischemic lesion volume in WT-dMCAo mice was 10.79%±0.97%. FIG. 1A and FIG. 1B show that stroke significantly decreased cardiac function identified by decreased LVEF compared to non-stroke mice ($p<0.05$). Cardiac fibrosis was evident both in the perivascular and in the myocardial interstitial area in the dMCAo group. FIG. 1 shows that stroke significantly increased myocyte cross-sectional area and interstitial fibrosis compared to non-stroke mice. These data indicate that stroke initiates myocyte hypertrophy and interstitial fibrosis.

To test the mechanisms of stroke-induced cardiac dysfunction, oxidative stress, inflammatory factor (infiltrating macrophages, ED1), TGF-β and oxidative stress (NOX2) expression were measured in the heart. FIGS. 2A-D shows that stroke significantly increased ED1, TGF-β, and NOX2 expression in the heart compared to WT control mice, as measured by immunostaining and Western blot.

Figure 3A:
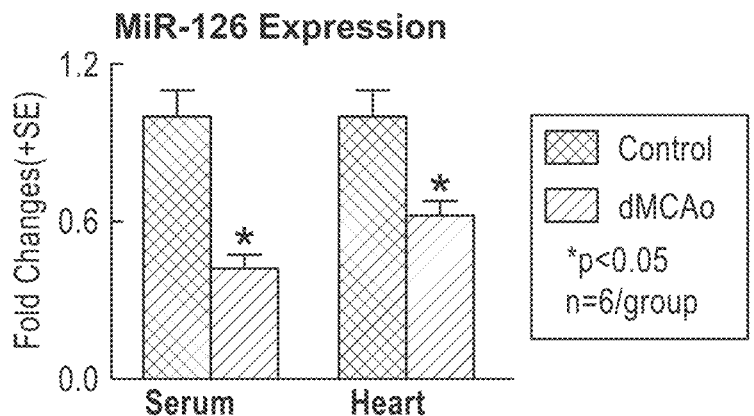
FIG. 3A, FIG. 3B and FIG. 3C depict the expression of miR-126 and its targets following a stroke. As shown in panel FIG. 3A, miR-126 expression is decreased in dMCAo mice.
Figure 3B:
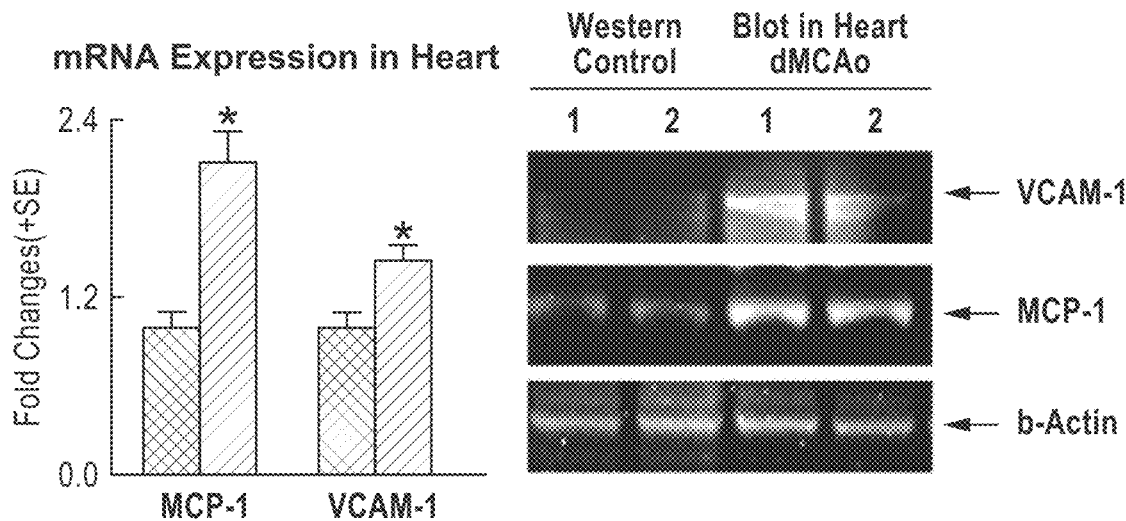
Figure 3C:
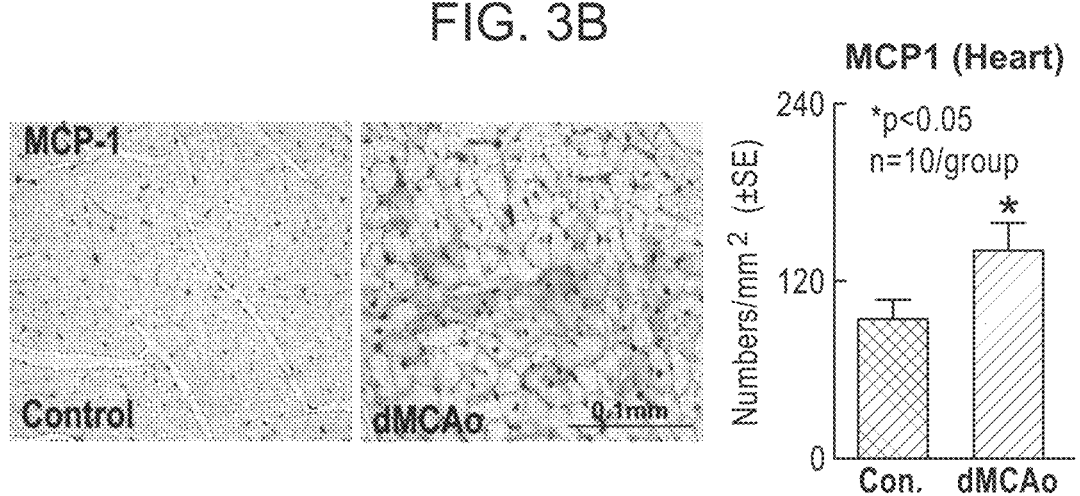

Cerebral ischemic stroke significantly decreases heart and serummiR-126 and increases miR-126 targets MCP-1 and VCAM-1 expression in heart tissue. To test possible mechanisms of stroke-induced cardiac dysfunction, miR-126 expression was measured in blood serum and heart tissue. FIGS. 3A-C shows that dMCAo significantly decreased serum and heart miR-126 expression compared to non-stroke mice. To test whether stroke regulates miR-126 target gene and protein expression, selected specific miR-126 target genes and proteins (MCP-1 and VCAM-1) were measured. FIGS. 3A-C shows that stroke increased heart tissue MCP-1 and VCAM-1 gene and protein expression compared to non-stroke control. The data indicate that stroke decreased miR-126 and increased its targets, MCP-1 and VCAM-1 gene and protein expression in the heart tissue.

Cerebral ischemic stroke in miR-126EC−/− mice results in increased cardiac dysfunction, cardiac hypertrophy, interstitial fibrosis, inflammation and oxidative stress compared to WT miR-126fl/fl stroke mice. To test if miR-126 affects cardiac function, echocardiography was performed in miR-126EC−/− and miR-126fl/fl mice after stroke. FIGS. 4A-D show that stroke in miR-126EC−/− induced a significantly worse cardiac function measured by decreased LVEF compared to miR-126fl/fl stroke (p<0.05), respectively. These data indicate that stroke exacerbates cardiac dysfunction in miR-126EC−/− mice compared with stroke in miR-126fl/fl mice. Differences in the ischemic lesion in the miR-126EC−/− and mrR-126fl/fl mice were tested, and FIGS. 4A-D show that there was no significant difference in lesion volume between miR-126fl/fl stroke and miR-126EC−/− stroke mice. Ischemic lesions in both sets of mice were located in the frontal and parietal cortex and the underlying corpus callosum without damage to the cardiovascular regions of the brain (insular cortex) and hypothalamus. Thus, ischemic lesion size and location are not responsible for the differential cardiac response to stroke in the miR-126EC−/− and miR-126fl/fl mice.

To test whether miR-126 deficiency exacerbates cardiac hypertrophy and fibrosis, MCSA and ICF were measured. FIGS. 4A-D show that stroke in miR-126EC−/− stroke mice significantly increased cardiomyocyte hypertrophy and cardiac fibrosis compared to miR-126fl/fl stroke mice.

FIGS. 5A-D show that stroke in miR-126EC−/− mice significantly increased heart TGF-β and NOX2 expression compared to stroke in miR-126fl/fl mice. MiR-126EC−/− stroke mice also exhibit significantly increased VCAM-1 and MCP-1 gene expression in the heart tissue compared to miR-126fl/fl stroke mice.

To test whether stroke regulates miR-126 expression in miR-126EC−/− mice, miR-126 expression in serum and heart were measured. FIGS. 5A-D show that miR-126EC−/− mice had lower levels of miR-126 expression in serum and heart than miR-126fl/fl mice (p<0.05). Stroke exacerbates the decrease of miR-126 expression in heart in both miR-126EC−/− and miR-126fl/fl mice.

Figure 6A:
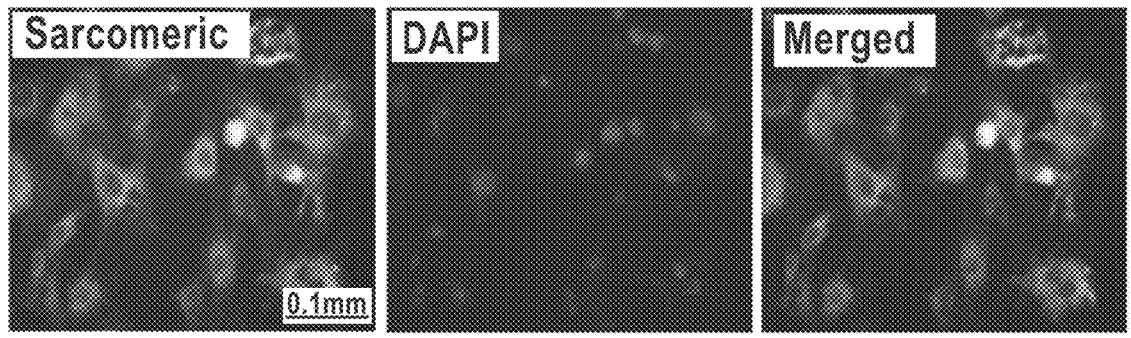
FIG. 6A, FIG. 6B, FIG. 6C, FIG. 6D, FIG. 6E, FIG. 6F and FIG. 6G depict miR-126 regulation of cardiomyocyte MCP-1 and VCAM-1 expression, and hypertrophy in primary cardiomyocyte cell culture.
Figure 6B:
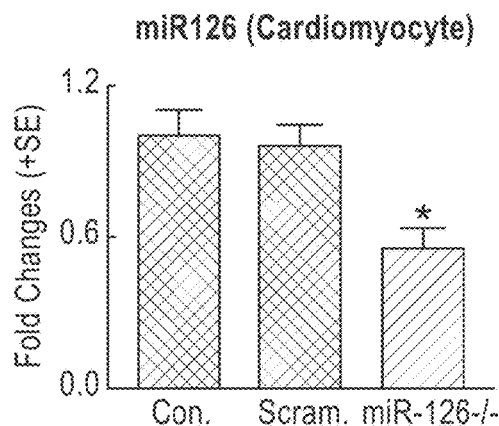
Figure 6C:
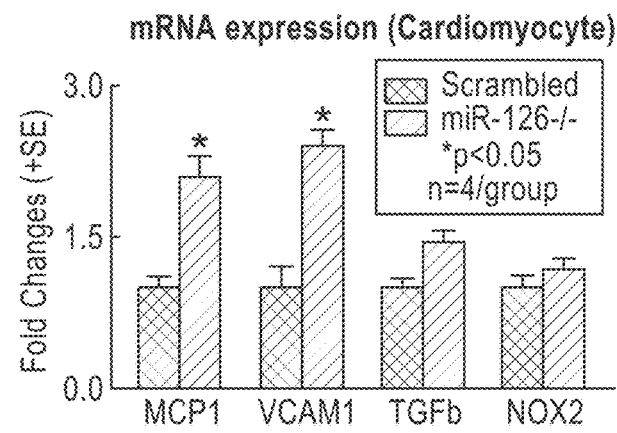
Figure 6D:
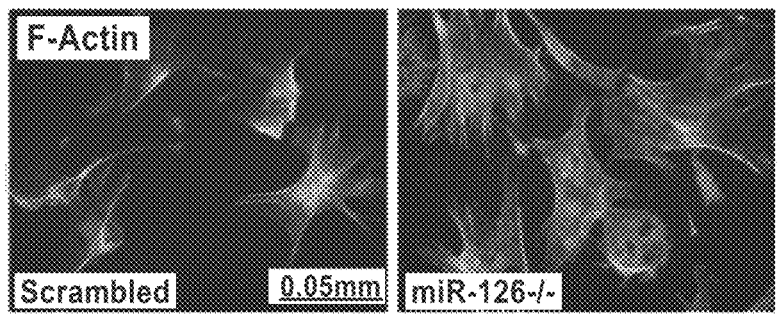
Figure 6D:
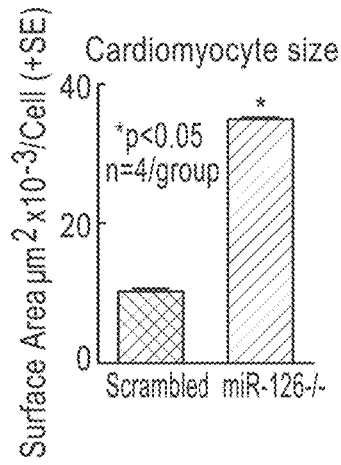
Figure 6E:
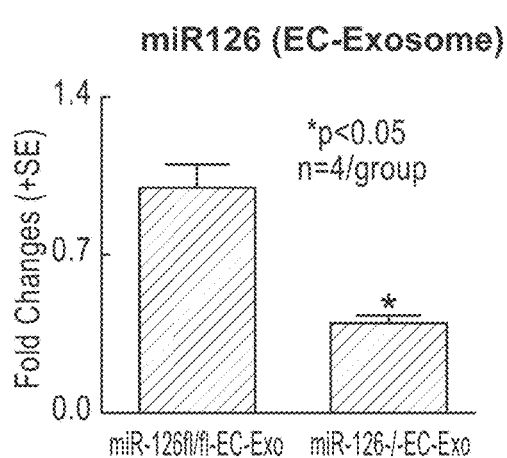
Figure 6F:
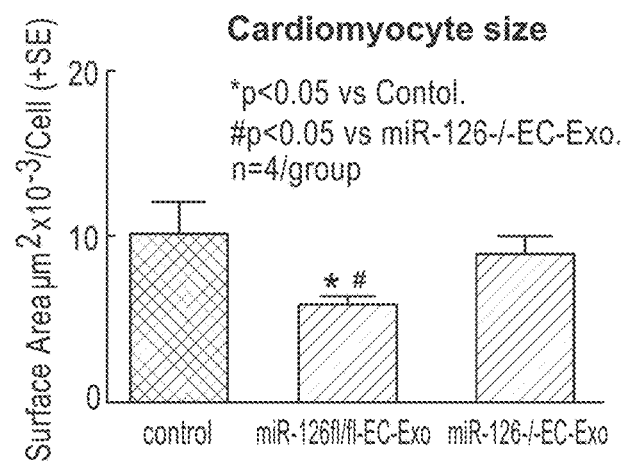
Figure 6G:
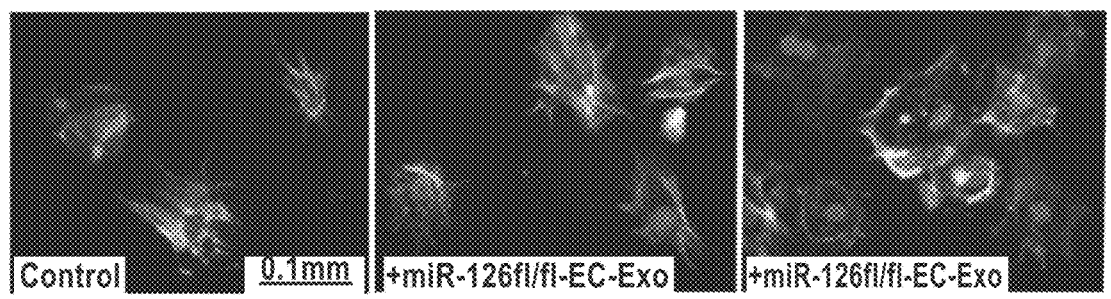

MiR-126 regulates cardiomyocyte hypertrophy in vitro. To confirm whether miR-126 directly regulates cardiomyocyte hypertrophy, cell size was measured by surface area calculation using fluorescence microscopy after anti-F-actinin staining in cultured cardiomyocytes. Using sarcomeric a-actinin staining, we found that 95% of cultured cells are cardiomyocytes (FIGS. 6A-G). In addition, knockdown of miR-126 in cardiomyocytes significantly decreased cardiomyocyte miR-126 expression and increased MCP-1 and VCAM-1 expression compared to scrambled control (FIGS. 6A-G). MiR-126 knockdown in cardiomyocytes also significantly increased cardiomyocyte size compared to scrambled knockdown control (FIGS. 6A-G). However, knockdown of miR-126 in cardiomyocytes did not affect cardiomyocyte cell death compared to scrambled cardiomyocyte knockdown control. The data indicate that miR-126 regulates cardio-myocyte hypertrophy. MiR-126 is a secreted miR and is primarily expressed in endothelial cells. We first measured miR-126 expression in exosomes derived from brain endothelial cells of miR-126fl/fl (miR-126fl/fl-EC-Exo) and miR-126EC−/− (miR-126EC−/− EC-Exo) mice. FIG. 6E shows that miR-126EC−/− EC-Exo exhibits significantly decreased miR-126 expression compared to miR-126fl/fl-EC-Exo. Second, we tested whether miR-126 in endothelial cell-derived exosomes affects cardiomyocytes. Exosomes derived from brain endothelial cells of miR-126fl/fl (miR-126fl/fl-EC-Exo) and miR-126EC−/− (miR-126EC−/− EC-Exo) were added to cultured cardiomyocytes subjected to OGD. FIGS. 6A-G shows that the addition of miR-126fl/fl-EC-Exo significantly decreased cardiomyocyte size compared to non-treatment OGD cardio-myocyte control or miR-126EC−/− EC-Exo-treated group, respectively. In addition, miR-126EC−/− EC-Exo treatment failed to decrease OGD cardiomyocyte hypertrophy compared to non-treatment cardiomyocyte control (p>0.05). These data indicate that depletion of EC source miR-126 may fail to protect cardiomyocyte from ischemic hypertrophy.

Here the inventors have demonstrated that stroke induces cardiac dysfunction and increases inflammatory and oxidative stress in the heart compared to non-stroke mice. Stroke decreases serum and heart miR-126 and increases miR-126 target gene and protein expression. Using specific conditional miR-126EC−/− mice, the inventors are the first to demonstrate that miR-126EC−/− stroke mice have more severe cardiac dysfunction and hypertrophy compared to miR-126fl/fl stroke mice, suggesting the importance of miR-126 as a mediator of brain and heart interaction after stroke.

Brain and heart interaction after stroke acute cerebrovascular disease, acute brain injury, intracranial inflammation and intracranial hypertension can all cause cardiac injury. During the first 3 months following acute ischemic stroke, 19.0% of patients encounter at least one major adverse cardiac episode; approximately 28.5% of stroke patients have an LVEF less than 50%; 13-29% of stroke patients have systolic dysfunction; and 35-74% have ischemic changes on electrocardiography. Therefore, there may be a causal relationship between brain damage and heart dysfunction. Here, the inventors have demonstrated that stroke leads to heart dysfunction at 28 days after stroke, as shown by decreased LVEF, as well as increased cardiac interstitial fibrosis and hypertrophy compared to non-stroke mice. Thus, the present invention may help to reduce neurological deficits and also to prevent or reduce cardiovascular disease or disorders subsequent to stroke.

MiR-126 may contribute to brain-heart interaction after stroke Select miRs are altered by stroke and cardiovascular dysfunction. Circulating miRs mediate intercellular communication, and some circulating miRs are correlated with brain miR changes after stroke. Furthermore, a knockout of miR-126 induces cardiac dysfunction. MiR-126 expression level in circulation is an indicator of systemic inflammatory and angiogenic status. MiR-126 concentration in the circulation is significantly decreased in ischemic stroke and acute myocardial infarction patients. In the plasma, miR-126 expression level correlates inversely with cardiac troponin-I concentration, which is a biomarker of myocardial damage. Administration of miR-126 increases EC proliferation and angiogenesis and improves cardiac neovascularization and cardiac function. MiR-126 upregulation by intravenous injection of a miR-126 mimic increases vascular density in the heart and improves cardiac function in an animal model of pulmonary arterial hypertension. The present disclosure demonstrates that stroke significantly decreases circulating and heart miR-126 expression compared to non-stroke mice. Knockdown of miR-126 in miR-126EC−/− mice subjected to stroke exhibit significantly increased cardiac dysfunction compared to miR-126fl/fl with stroke mice. MiR-126EC−/− stroke mice exhibit significantly increased cardiac fibrosis and hypertrophy compared to miR-126fl/fl stroke mice. In vitro, ECs secrete miR-126. MiR-126fl/fl-EC-Exo treatment of cardiomyocytes subjected to OGD exhibits significantly reduced hypertrophy than OGD cardiomyocytes treated with miR-126EC−/− EC-Exo, suggesting that miR-126 ameliorates OGD-induced cardiomyocyte damage.

Many other factors may also regulate brain-heart interaction. Brain control of the heart is mediated through the sympathetic and parasympathetic branches of the autonomic nervous system. Cardiovascular regions of the brain also regulate brain-heart interaction after stroke; for example, the right insular cortex has been implicated in cardiovascular sympathetic control. Here, in order to avoid the effects of direct brain lesion location of cardiac damage, the inventors used a dMCAo model that induces ischemic lesions in the frontal and parietal cortex, while the cardiovascular regions of the brain and hypothalamus are not affected. In addition, there was no significant difference in brain ischemic lesion volume between miR-126fl/fl and miR-126EC−/− stroke mice. Thus, miR-126 may facilitate brain and heart interaction, and decreasing miR-126 after stroke may contribute to induction of cardiac dysfunction.

MiR-126 may have inhibitory effects on heart inflammation and oxidative stress after stroke. The present disclosure demonstrates that miR-126EC−/− stroke mice exhibit significantly increased cardiac dysfunction compared to miR-126fl/fl stroke mice. Following acute brain injury or ischemia, neuroinflammatory response that impacts recovery includes microglial activation, leukocytes infiltration into the brain, stimulation and secretion of pro-inflammatory factors, and lymphocytes. MiRs control cellular expression machinery acting through "single miR/multiple targets" or "multiple miRNAs/single targets" mechanisms. Here, miR-126EC−/− mice have significantly increased inflammatory factors expression in the heart tissue. MCP1, VCAM-1, and Spred-1 are targets of miR-126; therefore, stroke-induced decrease of miR-126 subsequently increased miR-126's target gene expression. Reduced miR-126 expression may induce vascular inflammation by increasing the levels of VCAM-1, fibrinogen, and leukocyte counts. MiR-126 binds directly to the 3′-untranslated region of MCP-1 mRNA and controls MCP-1 production in a human monocyte/macrophage cell line. Increased expression of MCP-1 in ischemic brain tissue after stroke worsens injury and is associated with the recruitment of inflammatory cells. Monocytes are a major source of pro-inflammatory cytokines following myocardial tissue injury and are key inflammatory mediators of fibrosis in several pathological processes. Here, stroke significantly increases MCP-1 and VCAM-1 expression as well as increases ED1 positive inflammatory cell numbers in the heart compared to non-stroke mice. Stroke in miR-126EC−/− mice increased inflammatory factors and inflammatory cell numbers compared to stroke in miR-126fl/fl mice. Therefore, decreasing miR-126 and consequently increasing MCP-1 and VCAM-1 expression in the heart may promote infiltration of inflammatory cells into the heart after stroke.

Chronic inflammation has been implicated to play a critical role in the development and progression of ischemic heart failure and drives persistent myofibroblast activity and cardiac fibrosis. Monocyte-released TGF-β increases cardiac hypertrophy and fibrosis. TGF-β is a potent stimulator of cardiac myofibroblast activation and contributes to extracellular matrix deposition in the infarct by upregulating collagen and fibronectin synthesis as well as by decreasing matrix degradation. NOX2, a potent source of reactive oxygen species, promotes the transition of fibroblasts to myofibroblasts and mediates cardiac inflammation and fibrosis. TGF-β stimulation also increases the expression level of NOX2. Thus, NOX2 oxidative stress mediates cardiac fibrosis through TGF-β-dependent manner. We found that stroke increases heart TGF-β and NOX2 expression in the heart. Stroke in miR-126EC−/− mice enhances TGF-β and NOX2 expression compared to stroke in miR-126fl/fl mice. The inventors have shown that miR-126 regulates inflammatory effects and monocyte infiltration as well as regulates TGF-β and NOX2 expression. Therefore, miR-126/inflammation/oxidative stress may be involved in stroke-induced cardiac fibrosis and cardiac dysfunction.

Accordingly, the inventors have demonstrated that the miR-126 signaling pathway may be involved in stroke-induced cardiovascular disorder or disease. The experiments performed and described herein provide ample and statistically significant findings that lead one to conclude that a miR-126 containing agent can mitigate and/or ameliorate cardiovascular disease or disorder after a stroke.

Example 2

Figure 4A:
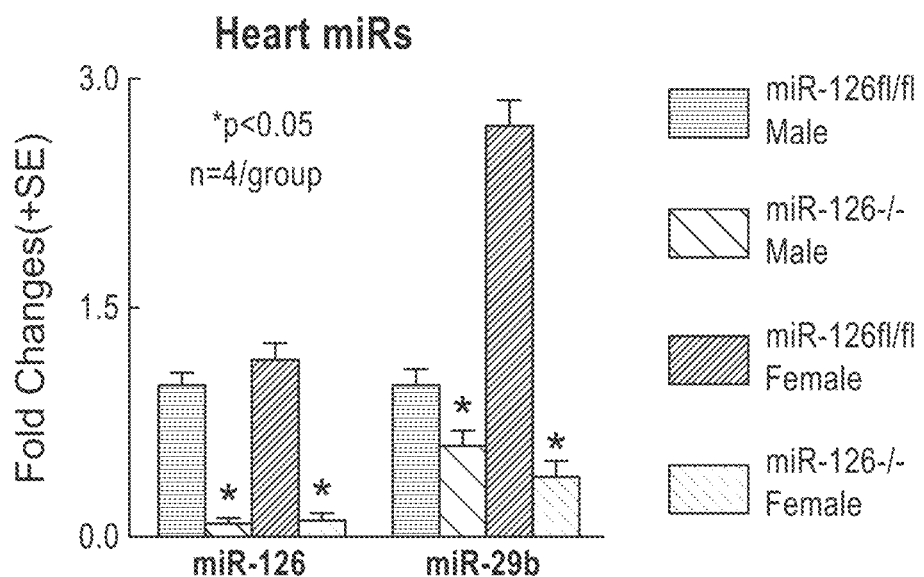
FIG. 4A, FIG. 4B, FIG. 4C and FIG. 4D depict decreased cardiac function, increased hypertrophy, and interstitial fibrosis in miR-126 knockout mice after ischemic stroke.
Figure 4B:
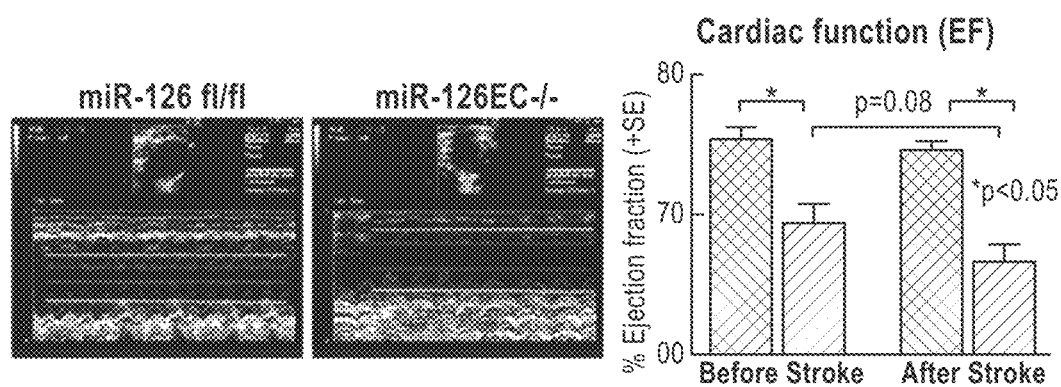
Figure 4C:
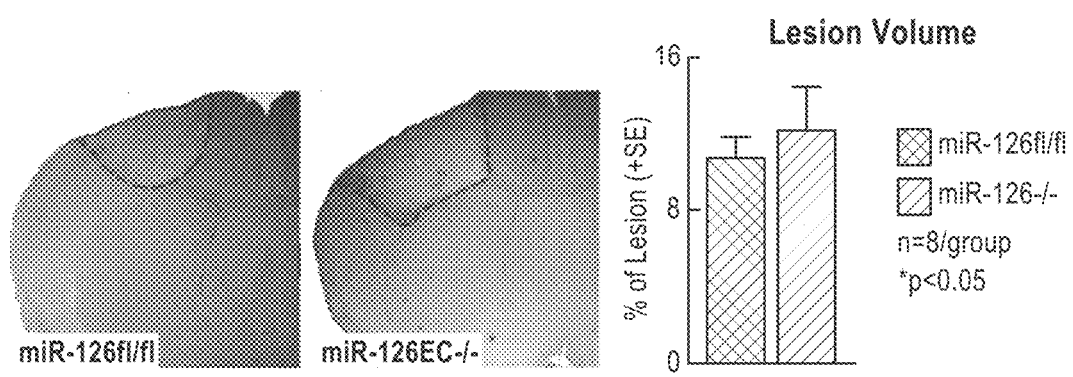
Figure 4D:
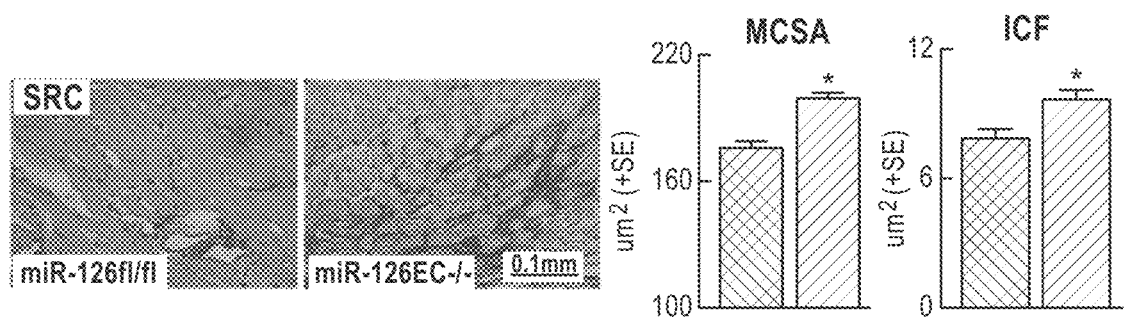
Figure 5A:
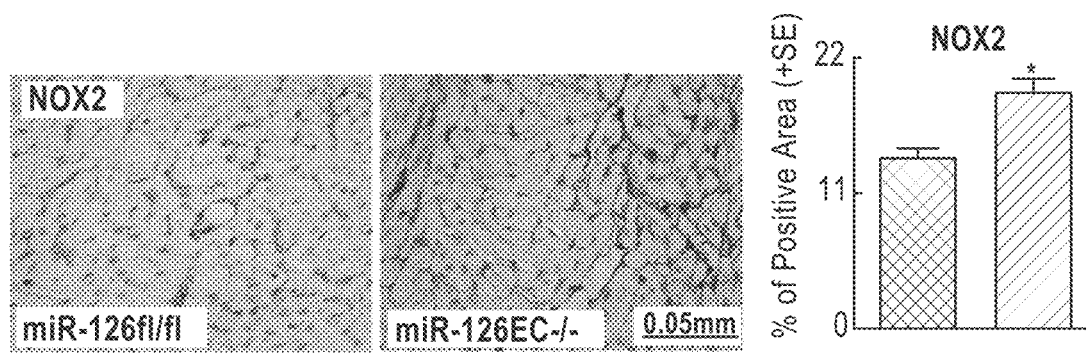
FIG. 5A, FIG. 5B, FIG. 5C and FIG. 5D depict increased inflammation and oxidative stress in miR-126 knockout mice after stroke compared to WT-stroke mice.
Figure 5B:
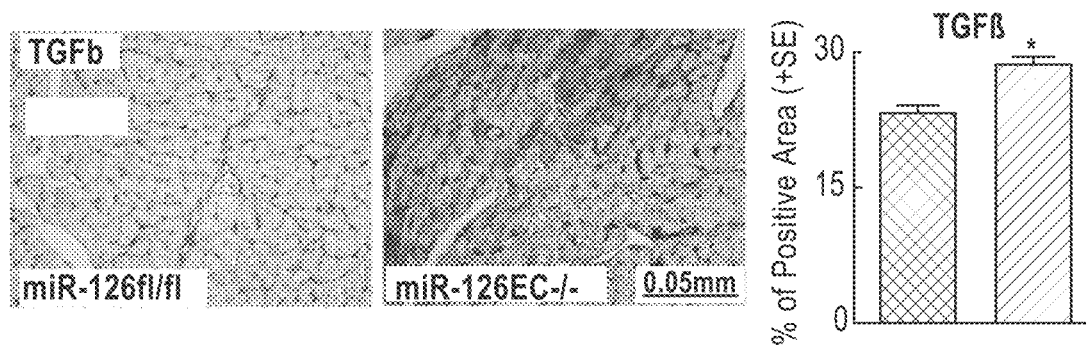
Figure 5C:
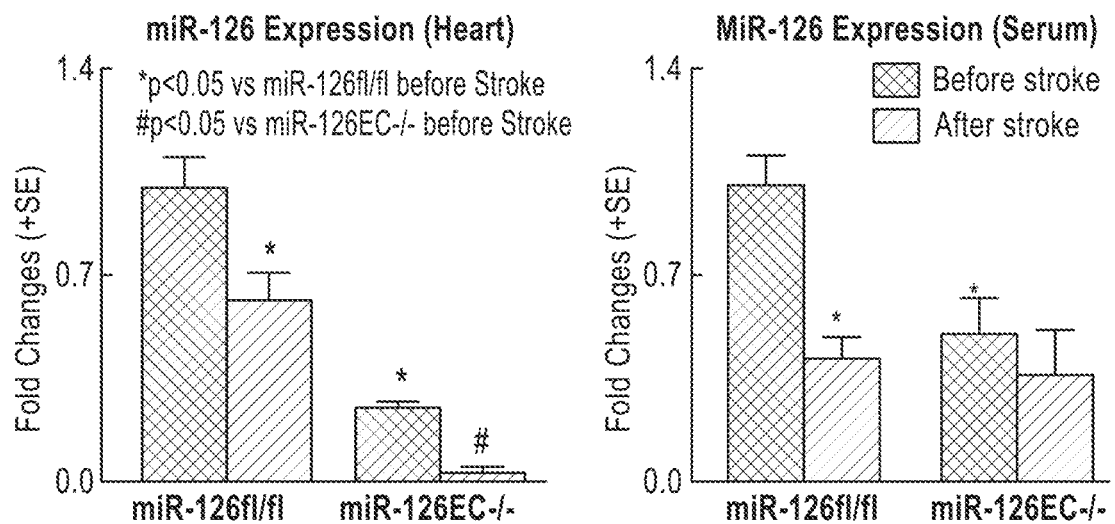
Figure 5D:
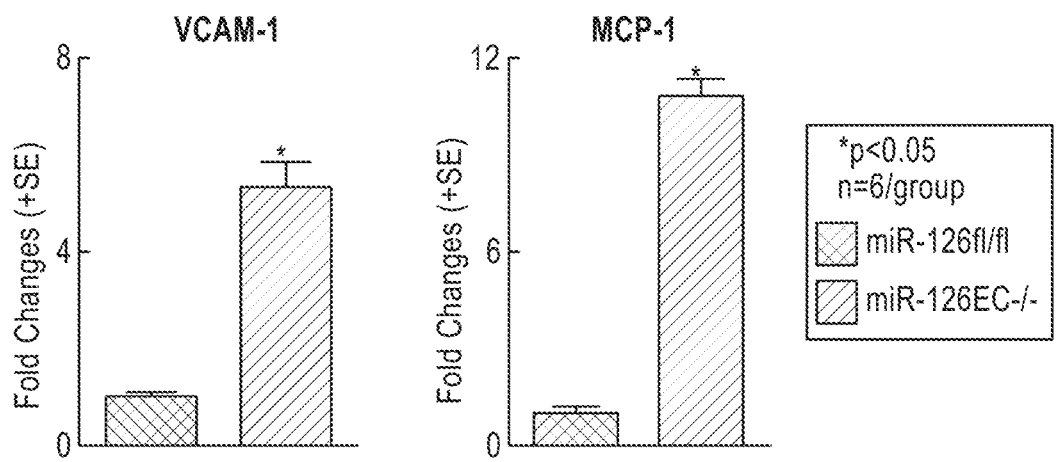

Example 2 shows the effect of a miR-126 containing agent on cardiovascular disease or disorder after a stroke, and in a subject with a glucose metabolism disorder. Here, the inventors demonstrate that specific conditional knockdown of endothelial cell miR-126 (miR-126EC−/−) mice exhibit significantly decreased miR-126 expression and decreased miR29b expression in heart. And, cerebral ischemic stroke in miR-126EC−/− mice increases cardiac dysfunction and cardiac fibrosis compared to miR-126fl/fl mice. To test miR-126 effect on the regulation of cardiac function, PDG-FiCreER:miR-126fl/fl were crossbred with miR-126fl/fl mice. Genotyping was employed at 8 weeks after birth, then both the PDGFBiCreER:miR-126fl/fl and miR-126fl/fl mice were treated with tamoxifen (1 mg/10 g body weight of tamoxifen dissolved in corn oil); 4 doses were administered every other day i.p. The tamoxifen treated PDGFiCreER:miR-126fl/fl mice are a specific EC-miR-126 deleted population (miR-126EC−/−); miR-126fl/fl was employed as knockdown control. MiR-126EC−/− and miR-126fl/fl mice were subjected to dMCAo. FIG. 4A, shows that miR-126EC−/− mice exhibit significantly decreased heart miR-126 expression compared to miR-126fl/fl control in male and female mice, respectively. Reducing miR-126 decreases heart miR-29b expression in male and female mice. FIGS. 4A-D shows that cardiac function was significantly decreased in miR-126EC−/− mice after stroke compared to miR-126fl/fl stroke mice, measured by LVEF. FIGS. 4A-D also shows that miR-126EC−/− stroke mice exhibit significantly increased cardiomyocyte hypertrophy (MCSA) and increased cardiac fibrosis (ICF) compared to miR-126fl/fl stroke mice. These data clearly demonstrate the pivotal role that miR-126 and miR-29b play in ameliorating cardiac dysfunction post stroke.

Figure 7:
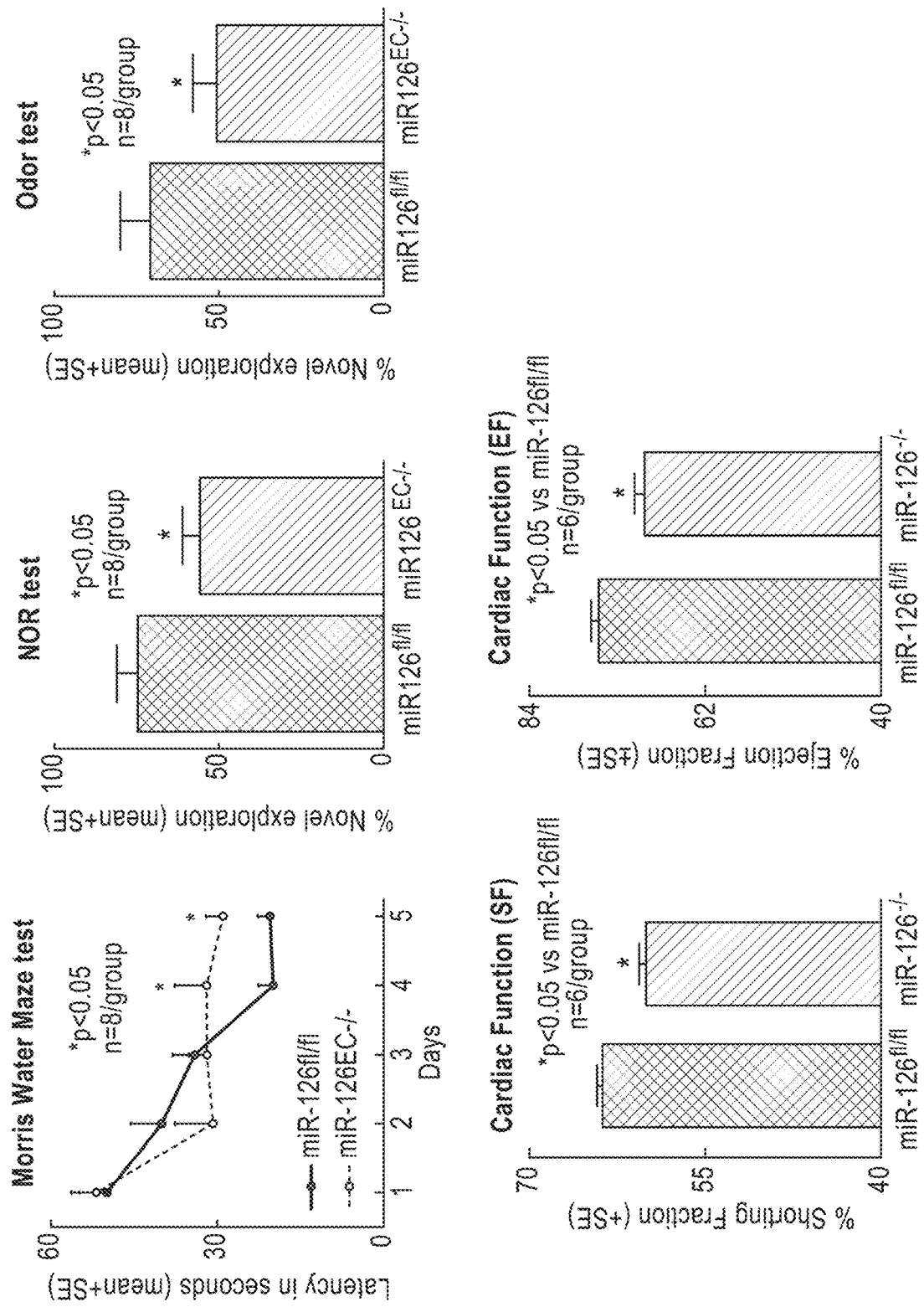
FIG. 7 depicts decreased cognitive function in middle age (6-8 months) miR-126 knockout mice. As shown in the top row of panels, knockout mice perform worse at cognitive tests. As shown in the lower set of panels, cardiac function measured by "shortening fraction (SF)" and "ejection fraction (EF)" is decreased in middle age miR-126 knockout mice.

Specific conditional knockdown of endothelial cell miR-126 (miR-126EC−/−) mice exhibit significantly decreased cognitive functional outcome and heart function compared to miR-126fl/fl control mice. To test whether miR-126 regulates cognitive and cardiac function, miR-126EC–/– and miR-126fl/fl mice were employed to evaluate cognitive and heart function in non-stroke mice. FIG. 7 shows that miR-126EC–/– mice exhibit significantly decreased cognitive function measured by Morris Water Maze (MWM) test, Novel Object Recognition (NOV) and Odor tests compared to non-miR-126 knockout control (miR-126fl/fl) mice. MiR-126EC–/– mice also exhibit significantly decreased cardiac function, measure by decreased LVEF and left ventricular shortening fraction (LVSF), compared to miR-126fl/fl control mice. These data indicate that miR-126 regulates cognitive and heart function.

Figure 8:
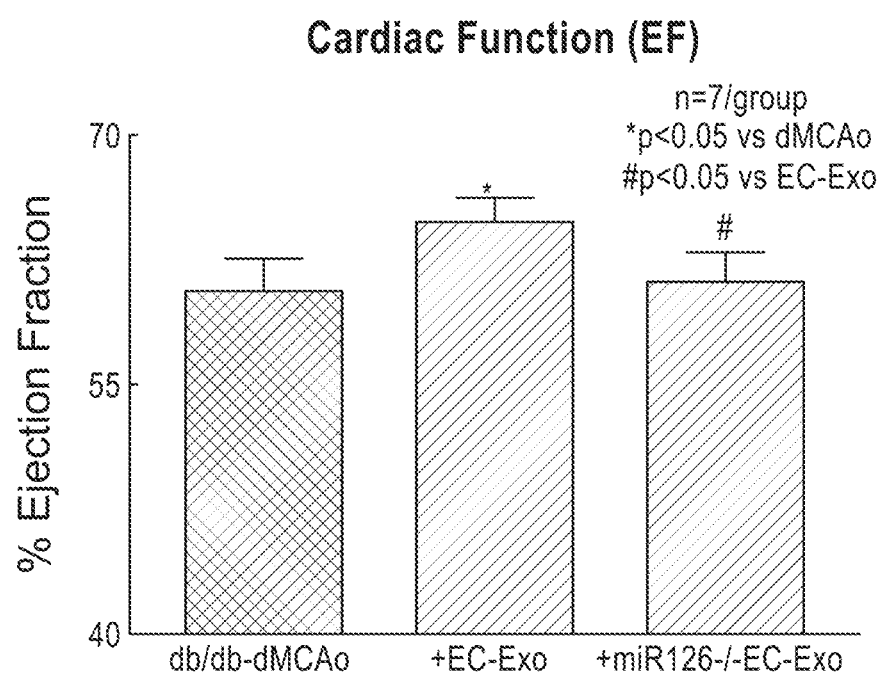
FIG. 8 depicts the improvement in cardiac function in type 2 diabetes mice (T2DM) with stroke, after the addition of exosomes harvested from endothelial cells (EC-Exo), and the attenuation of cardiac improvement after the addition of exosomes treated with a miR-126 inhibitor.

EC-Exo significantly improves cardiac function after stroke in T2DM mice. While knockdown of miR-126 in EC-Exo (miR-126–/–EC-Exo) significantly attenuates EC-Exo-induced cardiac protective effects. To test if EC-Exo treatment regulates cardiac function after stroke in T2DM mice, mouse brain endothelial cells (BEND3) were cultured with exosome-depleted FBS, then the cultured media were collected to isolate exosomes by ExoQuick TC (System Biosciences). To test if miR-126 regulates the EC-Exo-induced beneficial effects, knockdown of miR-126 in EC-Exo (mouse mmu-miR-126-3p inhibitor, Cell Biolabs) was performed using electroporation transfection. Then, BKS.Cg-m+/+Leprdb/J (db/db)-T2DM mice (3 months) were subjected to distal occlusion of the middle cerebral artery (dMCAo) and were randomized to intravenous injection via tail-vein with: Group-1) phosphate-buffered saline (PBS) as control; Group-2) EC-Exo)($3 \times 10^{10}$ treatment; 3) miR-126–/–EC-Exo)($3 \times 10^{10}$) initiated at 3 days after dMCAo. Echocardiography was employed to measure cardiac function in awake mice at 28 days after dMCAo. Transthoracic Doppler echocardiography was performed on conscious mice using a Doppler echocardiograph (Acuson C516) equipped with a 15-MHz linear transducer (15L-8). All measurements were digitized by goal-directed, diagnostically driven software and 3 beats were averaged for each measurement. LVEF reflects LV contractile function; LVDD (LV diastolic dimension) indicates LV chamber dimension. FIG. 8 shows that EC-Exo treatment significantly improves cardiac function after stroke in T2DM mice compared to T2DM-dMCAo control. While knockdown of miR-126 in EC-Exo (miR-126–/–EC-Exo) significantly attenuates EC-Exo-induced cardiac protective effects. The data indicate that increasing of miR-126 contributes to EC-Exo-induced cardioprotective effects, and that exosomes containing miR-126 or agents which induce miR-126 reduce cardiac dysfunction post stroke.

Figure 9C:
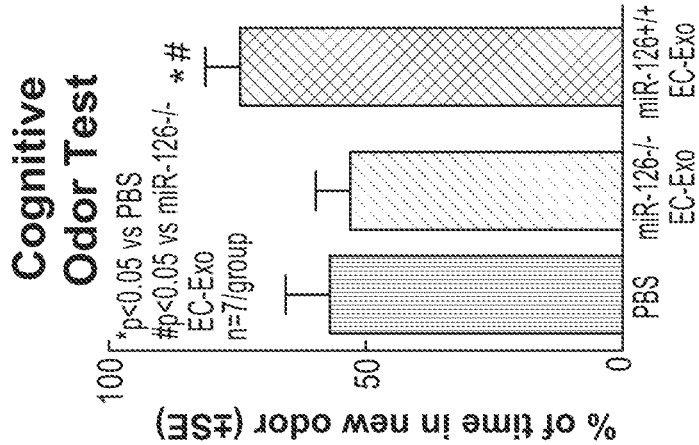
FIG. 9A, FIG. 9B and FIG. 9C depict the effect of miR-126 inhibition and overexpression on cognitive function after stroke in T2DM mice.
Figure 9B:
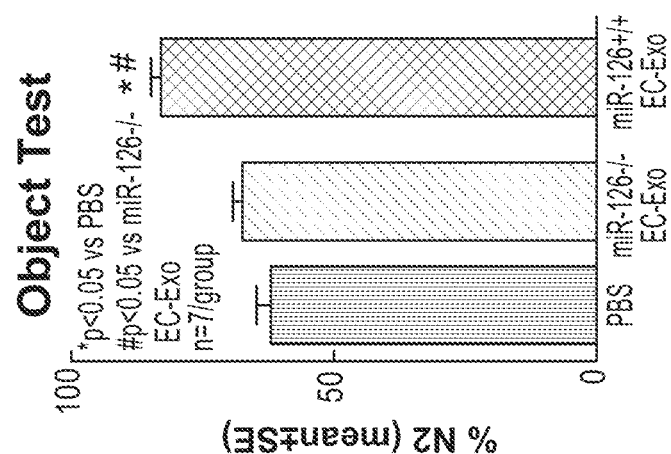
Figure 9A:
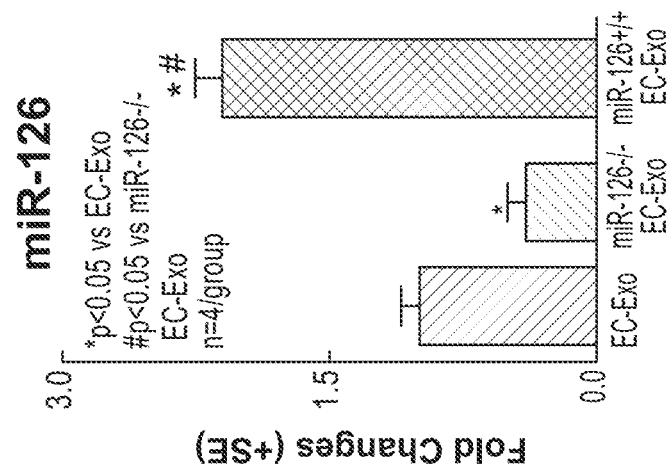

Modulation of miR-126 in EC-Exo influences EC-Exo treatment induced cognitive functional outcome after stroke in T2DM mice. To test if miR-126 regulates EC-Exo-induced neurorestorative effects, knockdown of miR-126 in EC-Exo (mouse mmu-miR-126-3p inhibitor) or overexpression of miR-126 in EC-Exo (pEGP-MMU-miR-126 Expression vector, MMU-miR-126 for miR-126 knock-in, Cell Biolabs) was performed using electroporation transfection. FIGS. 9A-C shows that knockdown of miR-126 in EC-Exo (miR-126–/–EC-Exo) significantly decreases miR-126 expression, but knock-in miR-126 in EC-Exo (miR-126+/+ EC-Exo) significantly increases miR-126 expression compared to EC-Exo control in vitro. T2DM-dMCAo mice were treated via intravenous injection with: 1) PBS (2 ml) control; 2) miR-126–/–EC-Exo ($3 \times 10^{10}$); 3) miR-126+/+EC-Exo) ($3 \times 10^{10}$ initiated at 3 days after dMCAo. FIGS. 9A-C also shows that miR-126+/+EC-Exo significantly improves cognitive outcomes after stroke, measured by Novel Object and Odor cognitive functional tests, when compared to miR-126–/–EC-Exo, or PBS control. These data indicate that miR-126 in exosomes regulates cognitive functional outcome after stroke in T2DM mice, with treatment with exosomes enriched in miR-126 inducing significantly improved cognitive function than treatment with control exosomes and miR-126 deficient exosome treatments, respectively, and control exosome treatment inducing significantly improved cognitive function after stroke than miR-126 knockdown exosomes.

Figure 10:
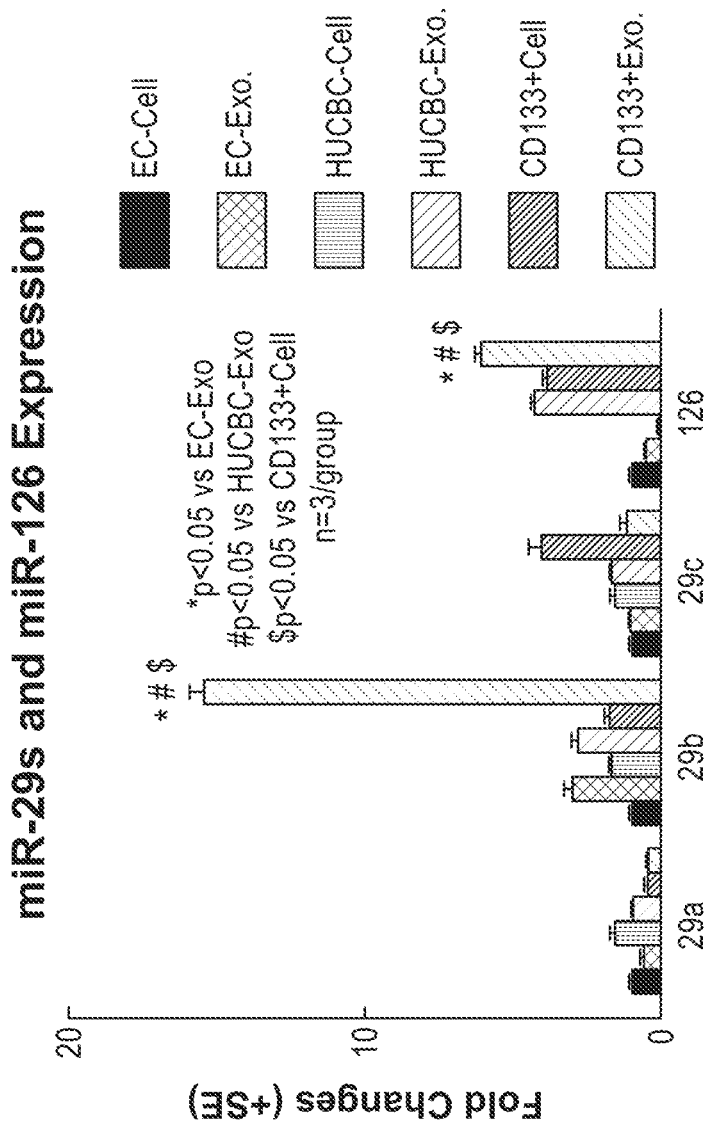
FIG. 10 depicts the increased content of miR-126 in exosomes harvested from CD133+ cells, and additional miRNA levels. Here, different cell types and their corresponding miR-126 exosome content were quantified. Brain endothelial cells (ECs), human umbilical cord blood cells (HUCBCs), and CD133+/KDR+ cells derived from HUCBCs were analyzed. As shown here, exosomes harvested from CD133+ cells (CD133+Exo) contained high levels of miR-126.
Figure 11A:
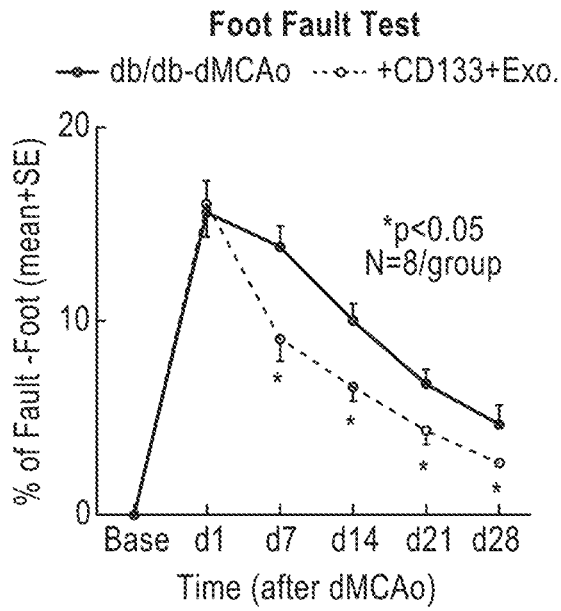
FIG. 11A, FIG. 11B, FIG. 11C, FIG. 11D, FIG. 11E, FIG. 11F, FIG. 11G, FIG. 11H, FIG. 11I and FIG. 11J depict the significant improvement in cognitive and cardiac function in stroke/T2DM mice treated with exosomes harvested from CD133+ cells.
Figure 11B:
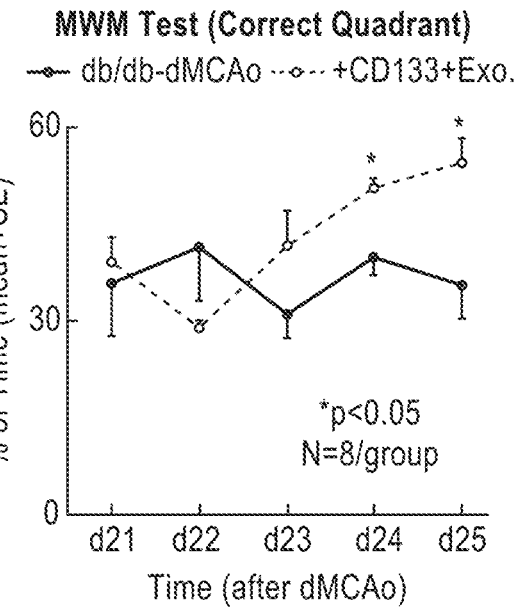
Figure 11C:
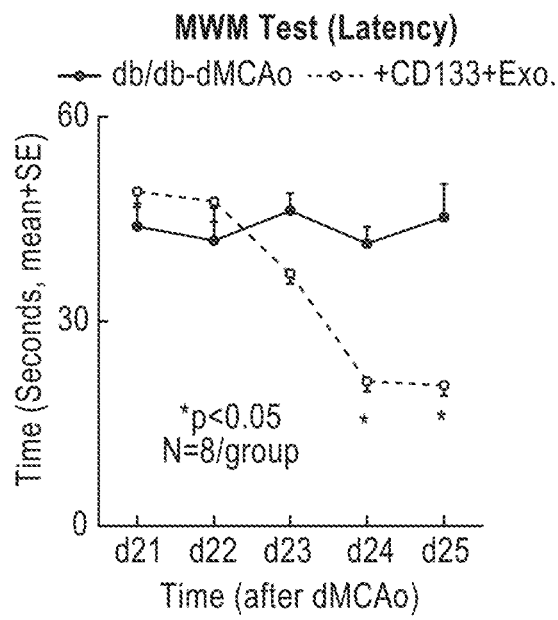
Figure 11D:
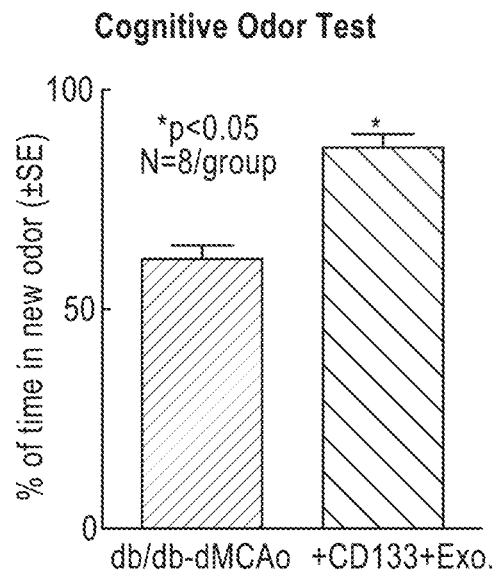
Figure 11E:
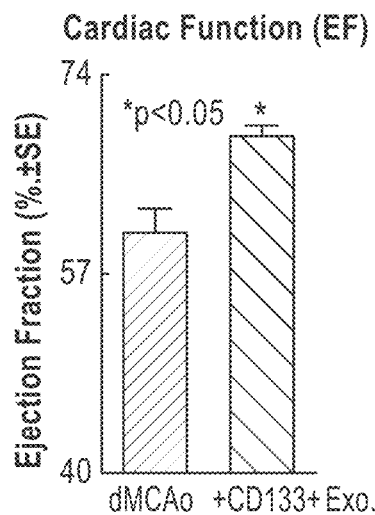
Figure 11F:
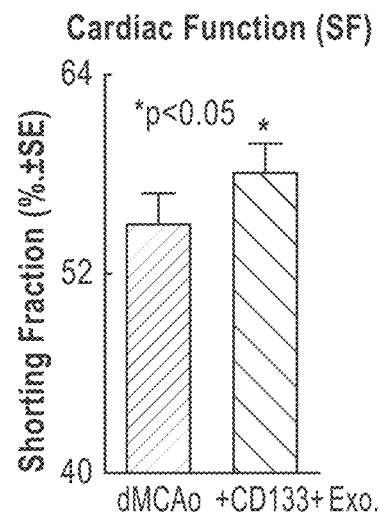
Figure 11G:
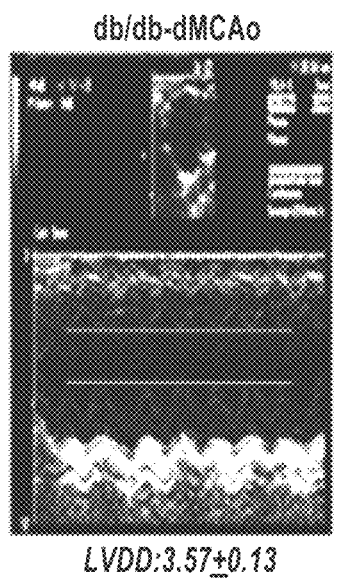
Figure 11H:
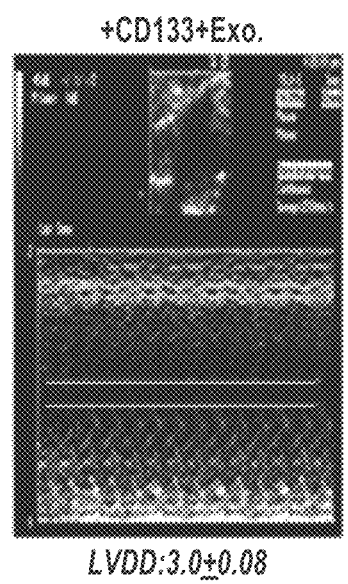
Figure 11I:
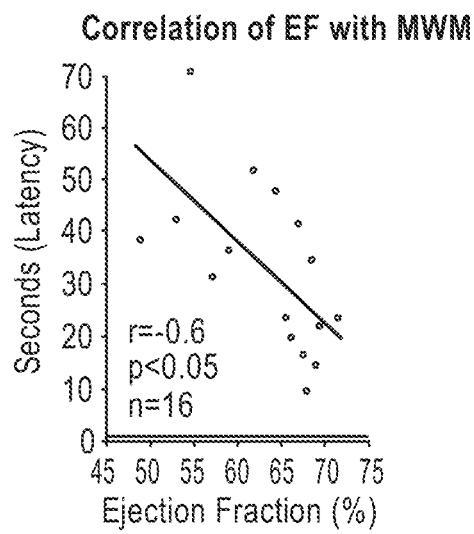
Figure 11J:
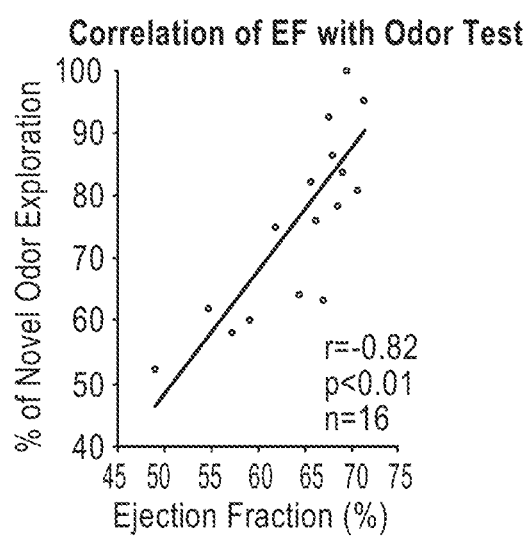

CD133+-Exo contains increased levels of miR-126 and miR-29b compared to EC-Exo and HUCBC-Exo. To compare different cell types and their exosome miR-126 and miR-29b content, brain endothelial cells (ECs), human umbilical cord blood cells (HUCBCs), and CD133+/KDR+ cells derived from HUCBCs were cultured in vitro. CD133+/KDR+ cells were isolated from HUCBC by immunomagnetic positive selection using the MidiMACS system (Miltenyi Biotec, Auburn Calif.). ECs, HUCBC and CD133+/KDR+ cells were cultured with exosome-depleted FBS, then the cultured media were collected to isolate exosome by ExoQuick TC (System Biosciences). Exosome concentration was determined using a qNano (Izon) machine. Exosomes harvested from HUCBC derived CD133+/KDR+ cells (called CD133+Exo). FIG. 10 shows that CD133+Exo contain high levels of miR-126 and miR-29b compared to EC-Exo and HUCBC-Exo. CD133+Exo also have higher levels of miR-126 and miR-29b than CD133+/KDR+ cells.

Treatment of stroke in T2DM mice with CD133+Exo significantly improves cardiac and cognitive function compared to PBS treated T2DM-stroke mice. To test if CD133+ Exo treatment regulates neurological, cognitive and cardiac functional outcome; adult (3-4 m) db/db-T2DM mice were subjected to dMCAo and treated 3 days after dMCAo with: 1) PBS as control; 2) CD133+Exo)($3 \times 10^{10}$) via tail vein injection. A battery of motor and cognitive functional outcomes (Foot fault, Morris water maze (MWM) and Odor test) were measured after stroke. Cardiac function was measured at 28 days after dMCAo by echocardiography. Here, CD133+Exo treatment at 3 days post stroke did not significantly decrease brain infarct volume (db/db-dMCAo: 11.1±0.8% vs CD133+Exo: 10.2±0.3%), but significantly decreases blood glucose (db/db-dMCAo:503.6±49.4 mg/dl vs CD133+Exo treatment: 354.5±30.6 mg/dl, p<0.05). FIG. 11A-E and FIG. 11G show that CD133+Exo treatment of stroke significantly decreases foot-fault (FIG. 11A) and cognitive deficits identified by MWM and Odor tests (FIGS. 11B-D), and also improves cardiac function identified by increased LVEF (FIG. 11E) and shorting fraction and decreased LVDD (FIG. 11G and FIG. 11D) compared to PBS treated T2DM mice. Furthermore, MWM-latency and Odor test are significantly correlated with cardiac function of LVEF (r=–0.6 for MWM-latency, r=0.82 for Odor test) and LVSF (r=–0.40 for MWM; r=0.64 for Odor test) after stroke in T2DM mice (p<0.05). Accordingly, the inventors demonstrate, for the first time, that CD133+Exo treatment improves neurological and cognitive function and also provides significant cardio protection after stroke in T2DM mice.

Figure 12A:
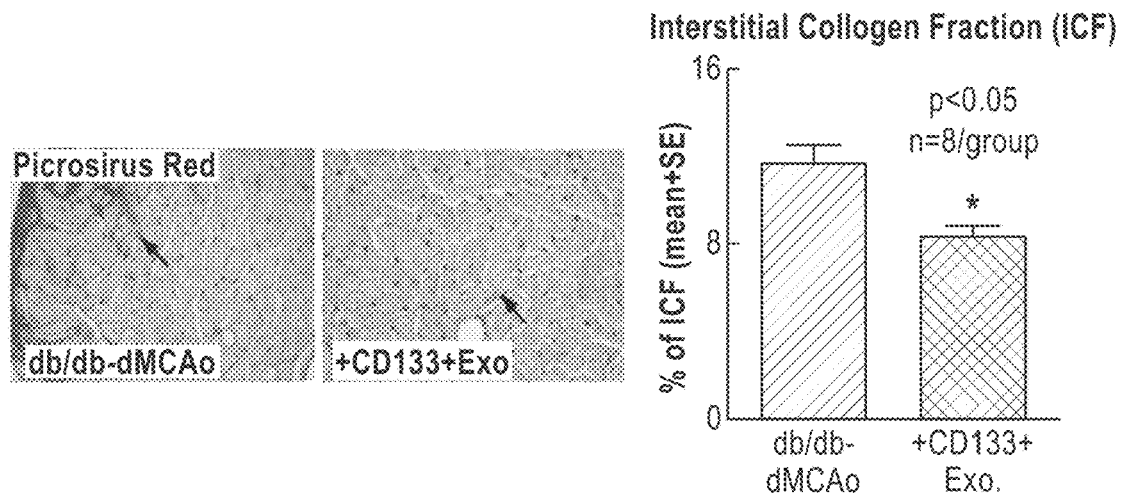
FIG. 12A, FIG. 12B and FIG. 12C depict a decrease in myocardial fibrosis, and TGF-β and NOX2 expression, following treatment with CD133+ exosomes in stroke/T2DM mice.
Figure 12B:
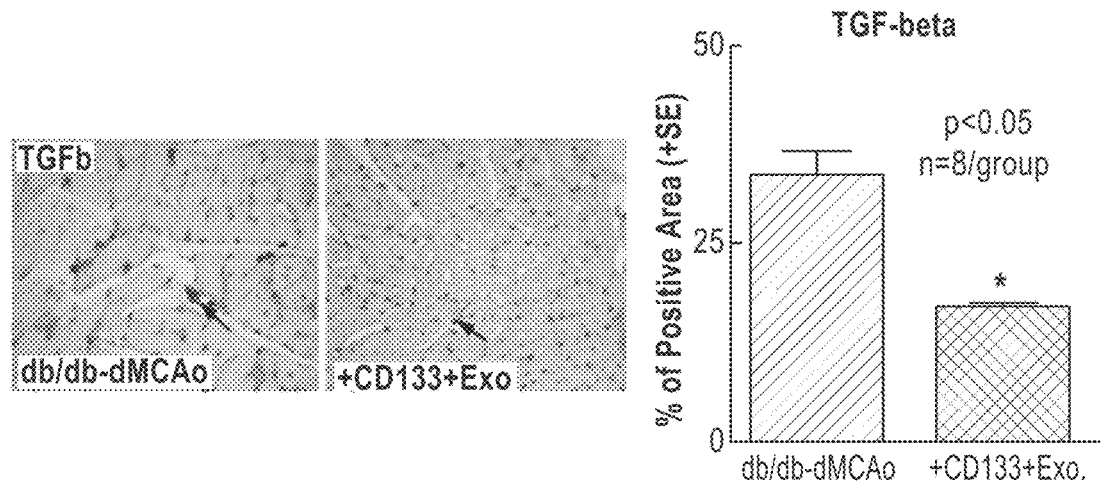
Figure 12C:
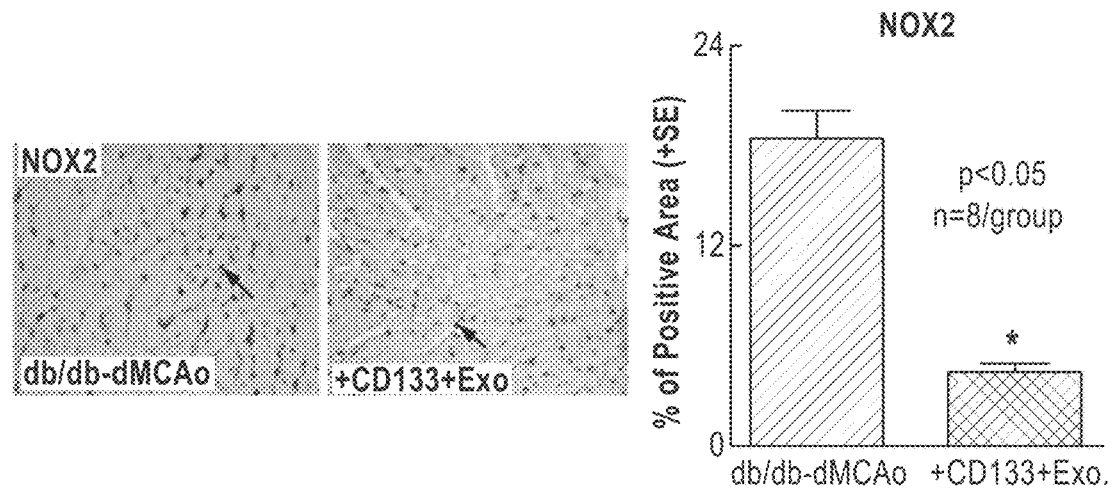

CD133+Exo treatment of stroke in T2DM mice significantly decreases myocardial fibrosis, TGF-β and NOX2 expression in heart. Mice were sacrificed at 28 days after dMCAo, and myocardial capillaries were stained by rhodamine-labeled *Griffonia simplicifolia* lectin, which identifies the microcirculation environment in the heart. Interstitial collagen fraction deposition (ICF) was measured by staining with fluorescein-labeled peanut agglutinin to delineated myocyte cross-sectional area (MCSA). ICF is a measurement of cardiac interstitial and perivascular fibrosis. MCSA identifies CM size. Using immunostaining, FIGS. 12A-B shows that stroke significantly decreases cardiac capillary density (FIG. 12A) and increases CM hypertrophy measured by MCSA, and increases collagen deposition identified by ICF (FIG. 12B) compared to non-stroke mice in non-DM and T2DM mice, respectively. T2DM-dMCAo mice exhibit decreased capillary density, increased cardiomyocyte hypertrophy and collagen deposition compared to non-DM-dM-CAo mice (FIGS. 12A-B). Thus, exosomes harvested from CD133+ cells significantly decrease cardiac dysfunction and factors that mediate this cardiac dysfunction.

Figures 13A, 13B:
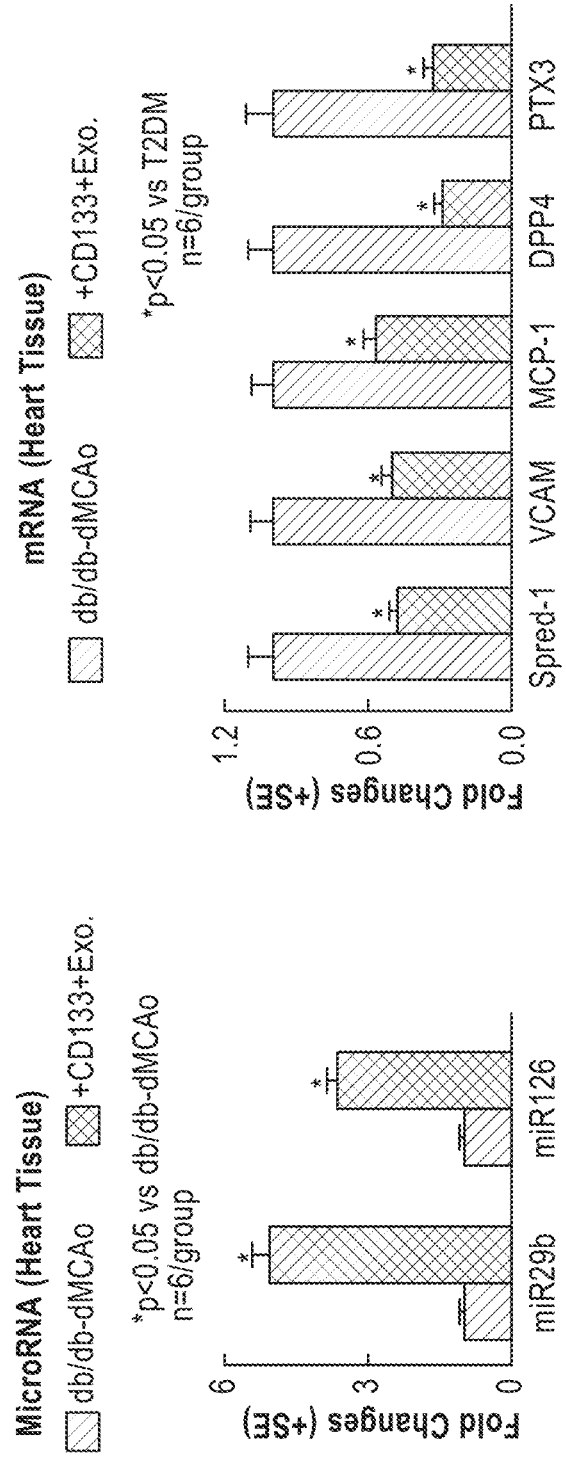
Figure 13E:
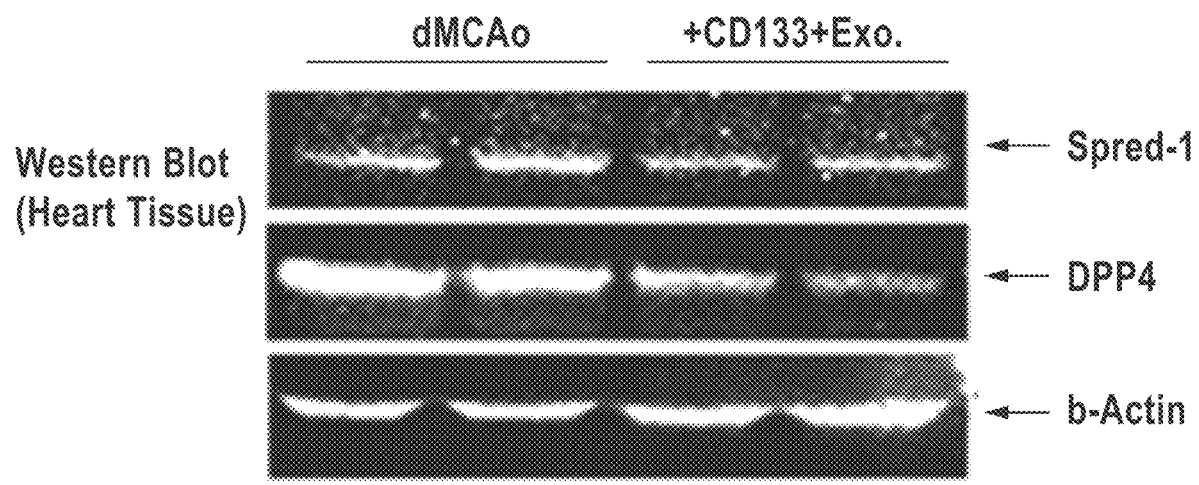

CD133+Exo treatment of stroke in T2DM mice significantly increases heart miR-126 and miR-29b expression, and decreases Spred-1 and DPP4 gene and protein expression. Spred-1, vascular cell adhesion molecule 1 (VCAM-1), and monocyte chemotactic protein-1 (MCP-1) are miR-126 target genes. DPP4 and long constituent pentraxin-3 (PTX3) are miR-29b target genes. FIGS. 13A-B show that CD133+ Exo treatment of stroke in T2DM mice significantly increases heart miR-126 and miR-29b expression (FIG. 13A), but decreases heart miR-126 target gene (Spred-1, VCAM-1 and MCP-1) and miR-29 target gene (DPP4 and PTX3) expression (FIG. 13B) compared to PBS treated T2DM-stroke mice. Using Western blot and immunostaining, FIGS. 13C-E show that CD133+Exo treatment significantly decreases heart Spred-1 and DPP4 protein expression compared to PBS-T2DM stroke mice. Based on the target genes affected by the miR-126 treatment, these data confirm that it is the miR-126 contained within the exosome that is responsible for the cardiac, neurological and cognitive therapeutic benefit of the exosome treatment.

The experiments performed and described herein provide ample and statistically significant findings that lead one to conclude that an miR-126 containing agent (e.g., exosomes and/or microvesicles derived from cerebral endothelial cells, Human umbilical cord blood cells (HUCBCs) and/or CD133+/KDR+ cells) mitigate and/or ameliorate cardiovascular disorders or diseases after a stroke in a patient with/without a glucose metabolism disorder.

Example 3

Intra-cerebral hemorrhage (ICH) induces chronic cardiac dysfunction compared to non-stroke mice.

To test whether ICH induces cardiac dysfunction, young adult (3 month old) C57BJ/6 mice were subjected to intra-cerebral hemorrhage (ICH). Briefly, 30 µl autologous blood withdrawn from the angular vein of a mouse was slowly injected (1 µl/min) into the mouse brain (2.3 mm lateral to midline, 0.5 mm anterior to bregma, 3.5 mm depth below the surface of the skull). Exosomes were isolated using the following procedures.

Centrifugation: collect cell culture media after cells have grown in it for a minimum of 48 hrs. Then filter media to remove any particulate matter and then centrifuge the media at 100,000 g for 2 hrs. After centrifugation remove the supernatant and add 100-300 µl PBS, then storing the final volume of exosomes at 4° C. for 1 week, or at −80° C. for prolonged storage, but do not expose exosomes to repeated freeze/thaw cycles. The exosomes can be quantized based on protein concentration using BCA assay (Pierce), or by a specific exosome counting system.

ExoQuick: Alternatively, instead of centrifugation, for smaller volumes of media or serum, we use Exoquick TC (System Biosciences). Add 2 ml Exoquick/10 ml medial (or 200 ul for every 1 ml media/serum). Incubate solution overnight at 4° C. and then centrifuge at 1500 g-2000 g for 30 minutes. Remove the supernatant and resuspend the pellet in PBS. As above, quantize using the BCA Protein Assay Kit (Pierce) following standard protocol. Store exosomes at 4° C. for 1 week, or at −80° C. for prolonged storage, but do not expose exosomes to repeated freeze/thaw cycles.

Figure 14:
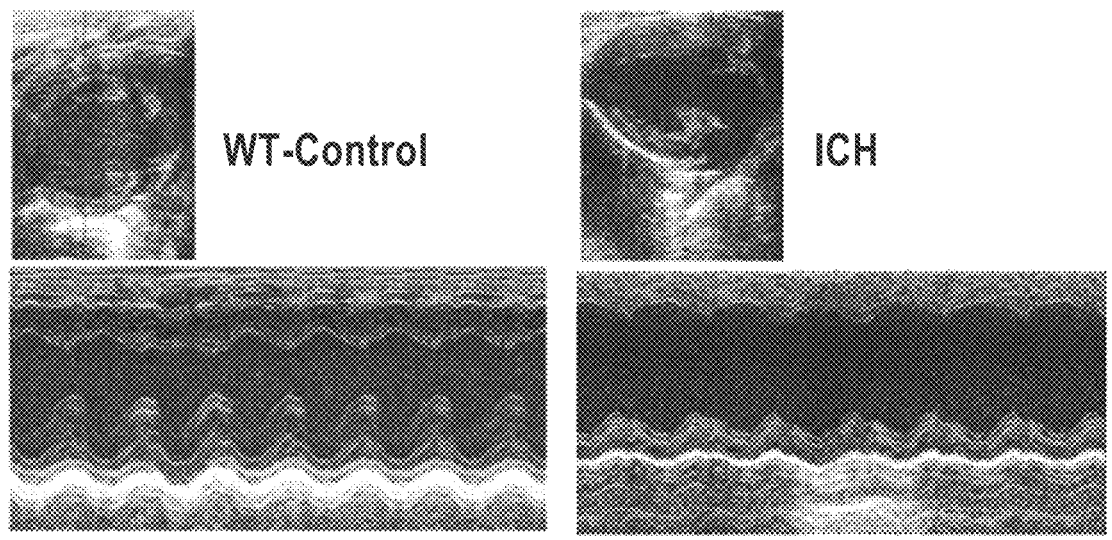
FIG. 14 shows that intracerebral hemorrhage (ICH) induces significant cardiac dysfunction identified by decreased LVEF and LVSF, and increased LVDD at 28 days after ICH compared to wild-type normal control mice.
Figure 14:
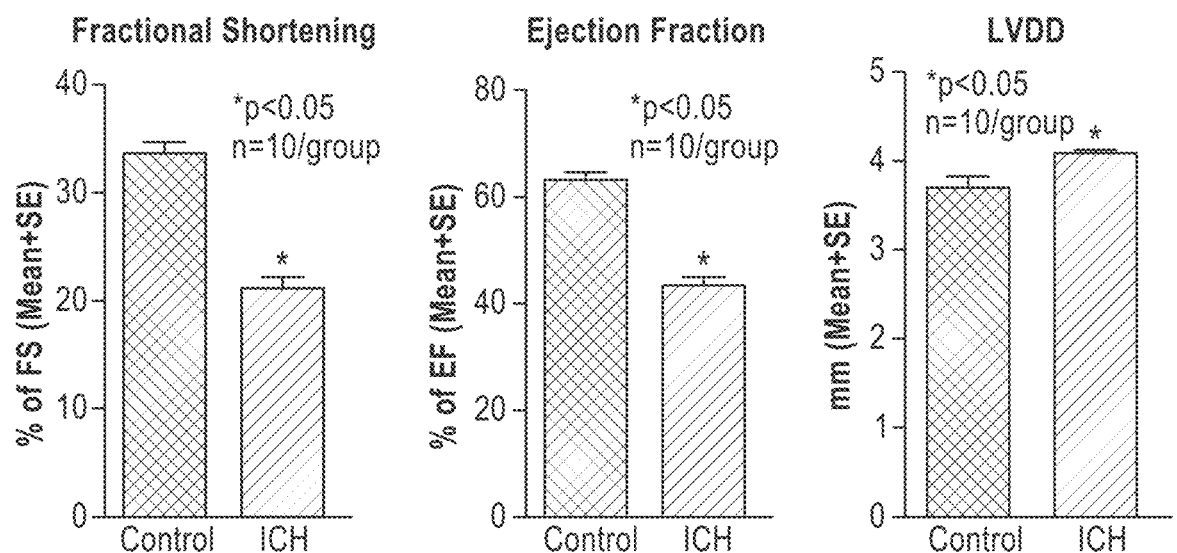

Echocardiography was employed to measure cardiac function at 28 days after ICH, including: 1) Left Ventricular diastolic dimension (LVDD); 2) LV shortening fraction (LVSF); 3) LV ejection fraction (LVEF); 4) LV diastolic volume/body surface area (BSA) (LVVol; d, ml/m2); 5) LV diastolic volume/BSA (LVVol; d, ml/m2). FIG. 14 shows that ICH induces significant cardiac dysfunction identified by decreased LVEF and LVSF, and increased LVDD at 28 days after ICH compared to wild-type normal control mice.

Subarachnoid hemorrhage (SAH) induces acute cardiac dysfunction compared to sham-control mice.

Figure 15:
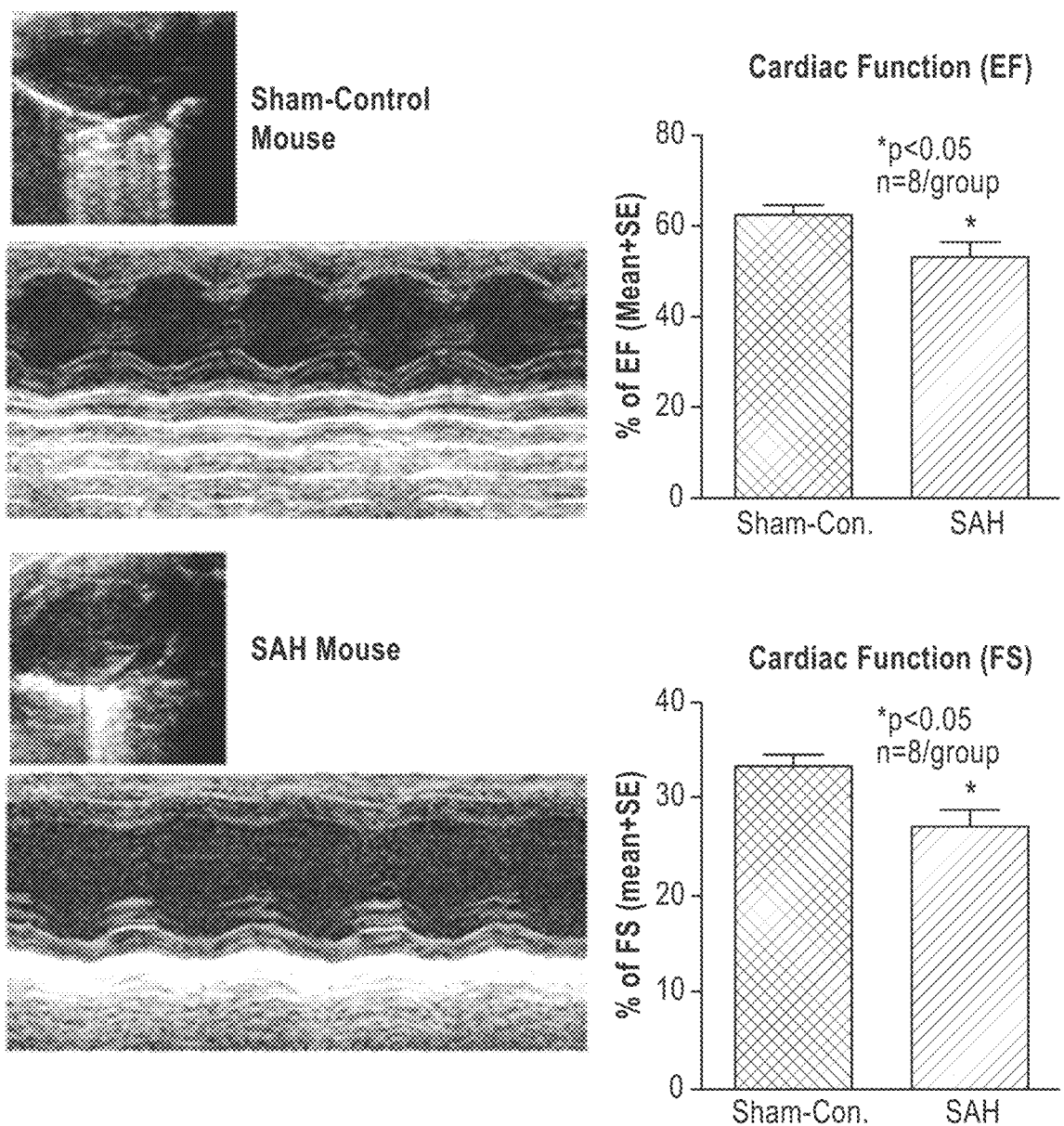
FIG. 15 shows that subarachnoid hemorrhage (SAH) induces significant cardiac dysfunction identified by decreasing LVEF and LVFS at 3 days after SAH compared to wild-type sham control.

To test whether SAH induces cardiac dysfunction, young adult (3 month old) C57BJ/6 mice were subjected to SAH by endovascular perforation model. Echocardiography was employed to measure cardiac function at 3 days after SAH, including: 1) LV mass; 2) LV shortening fraction (LVSF); 3) LVEF; 4) LV diastolic volume/BSA (LVVol; d, ml/m$^2$); 5) LV diastolic volume/BSA (LVVol; d, ml/m$^2$). FIG. 15 shows that SAH induces significant cardiac dysfunction identified by decreasing LVEF and LVFS at 3 days after SAH compared to wild-type sham control.

Example 4

The following experiments shows that human umbilical cord blood cell (HUCBC) or HUCBC-serum treatment of intracerebral hemorrhage (ICH) significantly improves cardiac functional outcome in ICH mice.

To test whether HUCBC cell or HUCBC-serum treatment improves cardiac function in ICH mice, young adult (3 months), male C57BJ/6 mice were subjected to ICH by autologous blood injection into mouse brain. ICH mice were randomized into three groups: 1) ICH control; 2) ICH+HUCBC; and 3) ICH+HUCBC-Serum.

For Group 2 ICH+HUCBC, ICH mice were treated with HUCBC (3×10$^6$ cells) via tail vein (i.v.) injection at 12 hours after ICH. For Group 3 ICH+HUCBC-serum, ICH mice were treated with 100 µl of HUCBC-serum via i.v. injection at 12 hours, 7 days and 14 days after ICH.

Figure 16:
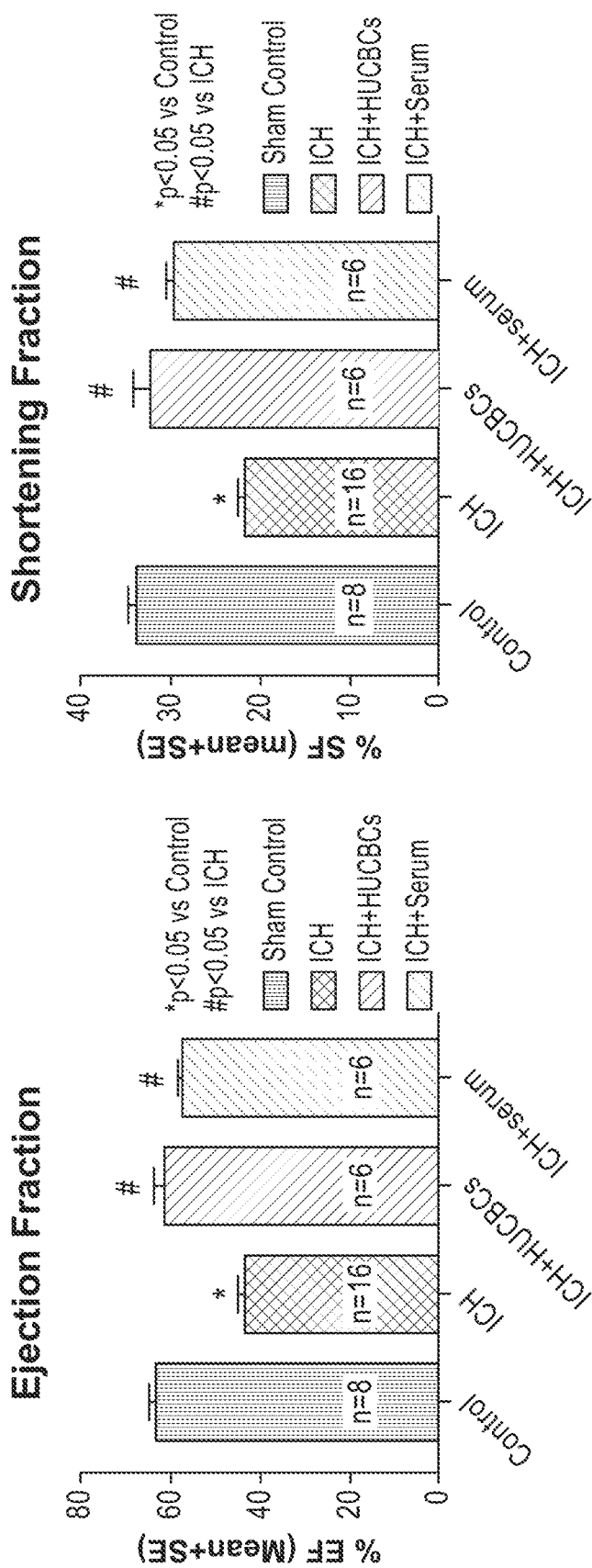
FIG. 16 is a series of graphs showing the LVEF and LV shortening fraction in ICH mice treated using methods of the present disclosure as measured by echocardiography.

Echocardiography was used in unconscious mice to evaluate cardiac function at 30 days after ICH. Left ventricular ejection fraction (LVEF) reflects LV contractile function. FIG. 16 shows that HUCBC and HUCBC-Serum treatment of ICH significantly improves cardiac function by increasing LVEF (left panel) and LV shortening fraction (LVFS; right panel) at 30 days after ICH compared to non-treated ICH control mice. The data indicate that treatment of ICH in mice with HUCBC and HUCBC-Serum significantly improves cardiac function.

Example 5

The following experiment shows that the treatment of ICH with HUCBC derived CD133+ cell or CD133+ exosomes significantly improves cardiac functional outcome compared to non-treated ICH control mice.

To test whether CD133+ cell or CD133+ exosome treatment improves cardiac function in ICH mice, young adult (3 months), male, C57BJ/6 mice were subjected to ICH by injecting collagenase (0.075 UI in 0.5 ul) into mouse brain. ICH mice were randomized into three groups: 1) ICH-Collagenase control; 2) ICH-Collagenase-CD133+ cells; and 3) ICH-Collagenase-CD133+ exosome.

For Group 2, ICH-Collagenase-CD133+ cells, ICH mice were treated with CD133+ cells ($1 \times 10^6$ cells, 25 µl) via intranasal administration 24 hours after ICH. For Group 3, ICH-Collagenase-CD133+ exosome, ICH mice were treated with CD133+ exosomes (10 µg/25 µl/mouse) at 24 hours, 3 days, 7 days and 10 days after ICH via intranasal administration.

Figure 17:
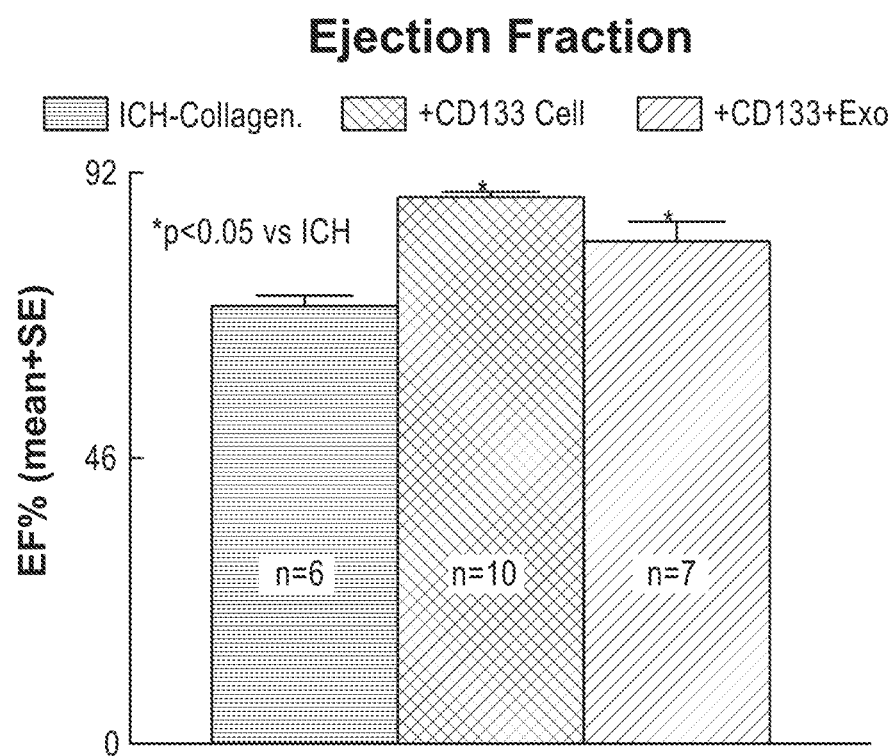
FIG. 17 is a graph showing LVEF in ICH mice treated using methods of the present invention as measured by echocardiography.

Echocardiography was used in awake mice to evaluate cardiac function at 14 days after ICH. FIG. 17 shows that CD133+ cell or CD133+ exosome treatment of ICH significantly improves cardiac function indicated by increased LVEF at 14 days after ICH compared to non-treated ICH control mice. In addition, increase in LVEF was significantly higher in ICH mice treated with CD133+ cells compared to ICH mice treated with CD133+ exosomes (p=0.05).

While some embodiments have been particularly shown and described with reference to the foregoing preferred and alternative embodiments, it should be understood by those skilled in the art that various alternatives to the embodiments described herein may be employed in practicing the invention without departing from the spirit and scope of the invention as defined in the following claims. This description of some embodiments should be understood to include all novel and non-obvious combinations of elements described herein, and embodiments may be presented in this or a later application to any novel and non-obvious combination of these elements. The foregoing embodiments are illustrative, and no single feature or element is essential to all possible combinations that may be claimed in this or a later application.

---

What is claimed is:

1. A composition comprising an isolated plurality of exosomes comprising miR-126, wherein the exosomes are derived from CD133+cells.

2. The composition of claim 1, wherein the exosomes further comprise miR-29b.

3. The composition of claim 1, wherein the plurality of exosomes are isolated from CD133+/KDR+Human Umbilical Cord Blood Cells.

4. The composition of claim 1, wherein the composition provides a dose of about $1\times10^{10}$ to about $1\times10^{19}$ exosomes per mL.

5. The composition of claim 1, wherein the exosomes contain a higher amount of at least one of miR-126 and miR-29b, relative to the amount of at least one of miR-126 and miR-29b in brain endothelial cells and human umbilical cord blood cells.

6. The composition of claim 1, wherein the composition decreases cardiomyocyte size in subjects with cardiac hypertrophy.

7. The composition of claim 6, wherein the cardiac hypertrophy is associated with a cerebral stroke.

8. The composition of claim 1, wherein the composition induces a reduction of cardiac fibrosis.

9. The composition of claim 1, wherein the composition comprises at least $3\times10^{10}$ exosomes.

10. The composition of claim 1, wherein the composition improves LVEF 14 days after treatment in subjects having experienced a cerebral stroke.

* * * * *

SEQUENCE LISTING

```
<160> NUMBER OF SEQ ID NOS: 16

<210> SEQ ID NO 1
<211> LENGTH: 22
<212> TYPE: RNA
<213> ORGANISM: Homo sapiens

<400> SEQUENCE: 1
ucguaccgug aguaauaaug cg                                          22

<210> SEQ ID NO 2
<211> LENGTH: 85
<212> TYPE: DNA
<213> ORGANISM: Homo sapiens

<400> SEQUENCE: 2
cgctggcgac gggacattat tacttttggt acgcgctgtg acacttcaaa ctcgtaccgt    60
gagtaataat gcgccgtcca cggca                                          85

<210> SEQ ID NO 3
<211> LENGTH: 85
<212> TYPE: RNA
<213> ORGANISM: Homo sapiens

<400> SEQUENCE: 3
cgcuggcgac gggacauuau uacuuuuggu acgcgcugug acacuucaaa cucguaccgu    60
gaguaauaau gcgccgucca cggca                                          85

<210> SEQ ID NO 4
<211> LENGTH: 22
<212> TYPE: DNA
<213> ORGANISM: Homo sapiens

<400> SEQUENCE: 4
tcgtaccgtg agtaataatg cg                                          22

<210> SEQ ID NO 5
<211> LENGTH: 21
<212> TYPE: RNA
<213> ORGANISM: Homo sapiens

<400> SEQUENCE: 5
cauuauuacu uuugguacgc g                                           21
```

-continued

<210> SEQ ID NO 6
<211> LENGTH: 21
<212> TYPE: DNA
<213> ORGANISM: Homo sapiens

<400> SEQUENCE: 6
cattattact tttggtacgc g                                              21

<210> SEQ ID NO 7
<211> LENGTH: 22
<212> TYPE: DNA
<213> ORGANISM: Mus musculus

<400> SEQUENCE: 7
gaaggaaaga gctgaagagc ag                                             22

<210> SEQ ID NO 8
<211> LENGTH: 22
<212> TYPE: DNA
<213> ORGANISM: Mus musculus

<400> SEQUENCE: 8
aggtttagga gagggtttcc ac                                             22

<210> SEQ ID NO 9
<211> LENGTH: 22
<212> TYPE: DNA
<213> ORGANISM: Mus musculus

<400> SEQUENCE: 9
ctgctactca ttcaccagca ag                                             22

<210> SEQ ID NO 10
<211> LENGTH: 22
<212> TYPE: DNA
<213> ORGANISM: Mus musculus

<400> SEQUENCE: 10
ctctctcttg agcttggtga ca                                             22

<210> SEQ ID NO 11
<211> LENGTH: 22
<212> TYPE: DNA
<213> ORGANISM: Mus musculus

<400> SEQUENCE: 11
gaattgtacg tggacagact gc                                             22

<210> SEQ ID NO 12
<211> LENGTH: 22
<212> TYPE: DNA
<213> ORGANISM: Mus musculus

<400> SEQUENCE: 12
caagtcatag gagggtttcc ag                                             22

<210> SEQ ID NO 13
<211> LENGTH: 22
<212> TYPE: DNA
<213> ORGANISM: Mus musculus

<400> SEQUENCE: 13

```
gcaacatgtg gaactctacc ag                                               22

<210> SEQ ID NO 14
<211> LENGTH: 22
<212> TYPE: DNA
<213> ORGANISM: Mus musculus

<400> SEQUENCE: 14
gtattccgtc tccttggttc ag                                               22

<210> SEQ ID NO 15
<211> LENGTH: 22
<212> TYPE: DNA
<213> ORGANISM: Mus musculus

<400> SEQUENCE: 15
caggtggagg tctactcatt cc                                               22

<210> SEQ ID NO 16
<211> LENGTH: 22
<212> TYPE: DNA
<213> ORGANISM: Mus musculus

<400> SEQUENCE: 16
ctccagatgg tcaaagggat ac                                               22
```